US012258477B2

(12) United States Patent
Yang et al.

(10) Patent No.: US 12,258,477 B2
(45) Date of Patent: Mar. 25, 2025

(54) SILICON-SUBSTITUTED RHODAMINE DYES AND DYE CONJUGATES

(71) Applicant: Life Technologies Corporation, Carlsbad, CA (US)

(72) Inventors: Jongtae Yang, Eugene, OR (US); Xin Wang, Eugene, OR (US); Yi-Zhen Hu, Eugene, OR (US); Kyle Gee, Springfield, OR (US); Aimei Chen, Eugene, OR (US); Aleksey Rukavishnikov, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 1054 days.

(21) Appl. No.: 17/150,247

(22) PCT Filed: Aug. 8, 2019

(86) PCT No.: PCT/US2019/045697
§ 371 (c)(1),
(2) Date: Jan. 15, 2021

(87) PCT Pub. No.: WO2020/033681
PCT Pub. Date: Feb. 13, 2020

(65) Prior Publication Data
US 2021/0324198 A1    Oct. 21, 2021

Related U.S. Application Data

(60) Provisional application No. 62/717,398, filed on Aug. 10, 2018.

(51) Int. Cl.
*C09B 11/28*    (2006.01)
*C07F 7/08*    (2006.01)
*C07F 9/6561*    (2006.01)
*C12Q 1/6816*    (2018.01)
*C12Q 1/6869*    (2018.01)
*G01N 33/58*    (2006.01)

(52) U.S. Cl.
CPC ............ *C09B 11/28* (2013.01); *C07F 7/0816* (2013.01); *C07F 9/6561* (2013.01); *C12Q 1/6816* (2013.01); *C12Q 1/6869* (2013.01); *G01N 33/582* (2013.01)

(58) Field of Classification Search
CPC ...... C09B 11/28; C07F 7/0816; C07F 9/6561; G01N 33/582; C12Q 1/6869
See application file for complete search history.

(56) References Cited

U.S. PATENT DOCUMENTS

| 9,139,868 | B2 | 9/2015 | Zhou et al. |
| 9,329,184 | B2 | 5/2016 | Nagano et al. |
| 9,429,568 | B2 | 8/2016 | Dyer et al. |
| 9,649,389 | B2 | 5/2017 | Groves et al. |
| 9,714,260 | B2 | 7/2017 | Nagano et al. |
| 2014/0272990 | A1 | 9/2014 | Zhou et al. |
| 2014/0342384 | A1 | 11/2014 | Nagano et al. |
| 2014/0349282 | A1 | 11/2014 | Umezawa et al. |
| 2023/0295437 | A1* | 9/2023 | Graham ................ C07F 7/0825 536/28.5 |

FOREIGN PATENT DOCUMENTS

| EP | 2748173 B1 | 11/2016 |
| JP | 2018025399 A | 2/2018 |
| WO | WO-2012083064 A1 | 6/2012 |
| WO | WO-2012111818 A1 | 8/2012 |
| WO | WO-2013029650 A1 | 3/2013 |
| WO | WO-2014144793 A1 | 9/2014 |
| WO | WO-2016029671 A1 | 3/2016 |
| WO | WO-2017201531 A1 | 11/2017 |
| WO | WO-2017222006 A1 | 12/2017 |

OTHER PUBLICATIONS

Lukinavičius, G., Blaukopf, C., Pershagen, E. et al. SiR-Hoechst is a far-red DNA stain for live-cell nanoscopy. Nat Commun 6, 8497 (2015). (Year: 2015).*
Bucevičius, et al., "The Use of Hoechst Dyes for DNA Staining and Beyond," Chemosensors, Mar. 20, 2018. (Year: 2018).*
Fu et al., "A design concept of long-wavelength fluorescent analogs of rhodamine dyes: replacement of oxygen with silicon atom", Chem. Commun., 2008, pp. 1780-1782.
Hirabayashi et al., "Analysis of chemical equilibrium of silicon-substituted fluorescein and its application to develop a scaffold for red fluorescent probes," Anal. Chem., 2015, vol. 87, pp. 9061-9069.
Koide et al., "Development of an Si-Rhodamine-based far-red to near-infrared fluorescence probe selective for hypochlorous acid and its applications for biological imaging," JACS, 2011, vol. 133, pp. 5680-5682.
Kushida et al., "Silicon-substituted xanthene dyes and their applications in bioimaging," Analyst, 2015, vol. 140, pp. 685-695.
Kushida et al., "Red fluorescent scaffold for highly sensitive protease activity probes," Bioorg. Med. Chem. Lett., 2012, vol. 22, pp. 3908-3911.
Lukinavicius et al., "A near-infrared fluorophore for live-cell super-resolution microscopy of cellular proteins," Nat. Chem., 2013, vol. 5, pp. 132-139.
Lukinavicius et al., "Fluorogenic probes for multicolor imaging in living cells," JACS, 2016, vol. 138, pp. 9365-9368.

(Continued)

*Primary Examiner* — Jared Barsky
(74) *Attorney, Agent, or Firm* — Klarquist Sparkman, LLP

(57) ABSTRACT

Silicon-substituted rhodamine compounds are disclosed herein. Also described herein are SiR dyes comprising at least one vinyl group attached to the Si atom (10 position) of the SiR dye. Derivatives, functionalized versions, conjugates, kits, related synthetic methods and uses of SiR compounds also are provided. Silicon-rhodamine (SiR) dyes can provide bright fluorescence at far red wavelengths and exhibit good photostability. The compounds described herein can be useful for fluorescent labeling and detection of biological samples.

7 Claims, 40 Drawing Sheets

(56) References Cited

OTHER PUBLICATIONS

Lukinavicius et al., "SiR-Hoechst is a far-red DNA stain for live-cell nanoscopy," Nat. Commun. 6:8497 (2015) & Supplementary Info, 16 pages.
Nakamura et al., "Hoechst tagging: a modular strategy to design synthetic fluorescent probes for live-cell nucleus imaging," 2014, Chem. Commun., vol. 50, pp. 6149-6152.
PCT/U2019/045697, Partial Search Report, Dec. 6, 2019.
PCT/U2019/045697, Search Report and Written Opinion, Mar. 11, 2020.
Umezawa et al., "Rational Design of Reversible Fluorescent Probes for Live-Cell Imaging and Quantification of Fast Glutathione Dynamics", Nature Chemistry, vol. 9, No. 3, Nov. 7, 2016, pp. 279-286, XP055643105.
Uno et al., "A spontaneous blinking fluorophore based on intramolecular spirocyclization for live-cell super-resolution imaging," 2014, Nat. Chem., vol. 6, pp. 681-689.
Wang et al., "A General Approach to Spirolactonized Si-rhodamines", Chemical Communications, vol. 50, No. 92, Jan. 1, 2014, pp. 14374-14377, XP055451714.
Koide Y., et al., "Development of NIR Fluorescent Dyes Based on Si-rhodamine for in Vivo Imaging," Journal of American Chemical Society, 2012, vol. 134, pp. 5029-5031.
Umezawa K., et al., "A Reversible Fluorescent Probe for Real-Time Live-Cell Imaging and Quantification of Endogenous Hydropolysulfides," Angewandte Chemie International Edition, 2018, vol. 57, pp. 9346-9350.

* cited by examiner

Compound 1

Compound 1A

Compound 1B

Compound 1C

Compound 2

Compound 2A

Compound 3

Compound 4A

Compound 4

Compound 5

Compound 6

Compound 7

Compound 7A

Compound 7B

Compound 8

Compound 9

Compound 10A

Compound 16

Compound 17

Compound 18

Compound 19

Compound 20

Compound 21

Compound 22

Compound 23

Compound 24

Compound 25

Compound 26

Compound 27

Compound 28

Compound 29

Compound 30

Compound 31

Compound 32

Compound 33

Compound 34

Compound 35

Compound 36

Compound 37

Cyclotetramethylenedichlorosilane

Compound 38

Compound 39

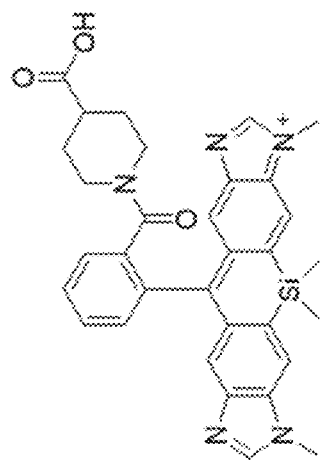
Compound 46
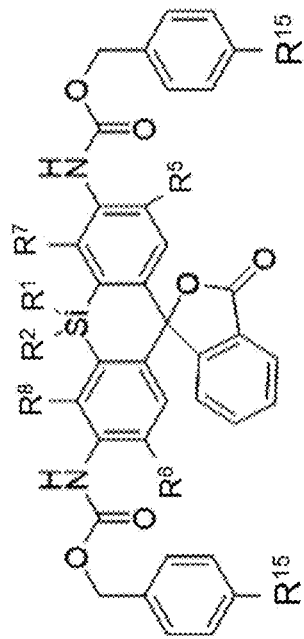
Compound 43
*Fig. 1L*
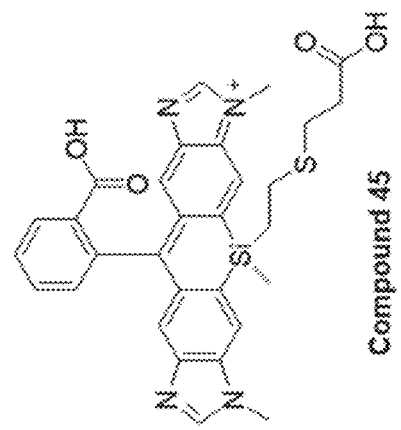
Compound 45
*Fig. 1M*
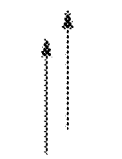
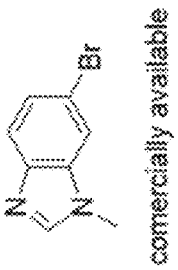
commercially available Compound 47

Compound 48

Compound 49

Compound 50

Chem Comm 2013, 10974

Fig. 4A
Field 1
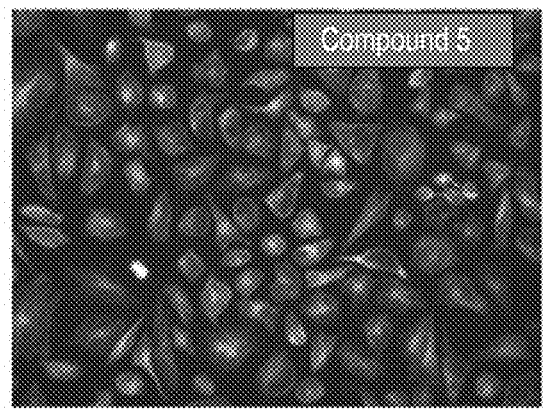
Fig. 4B
Field 2
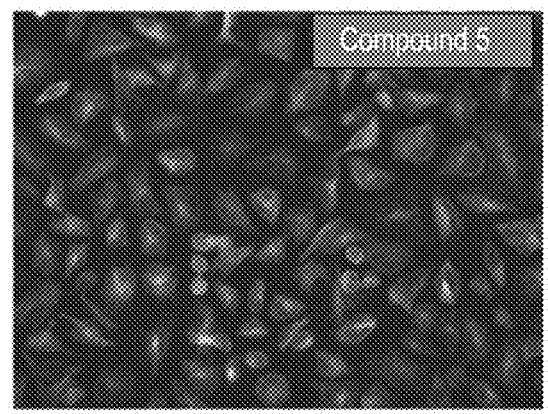
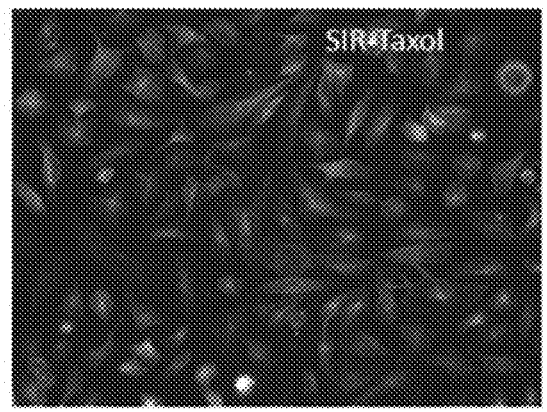
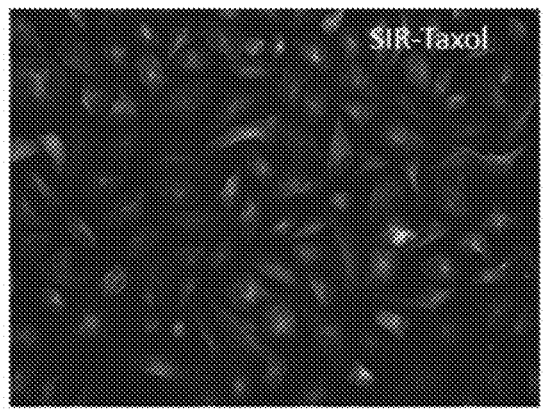
Fig. 4C
Fig. 4D

*Fig. 5A*
Brightness
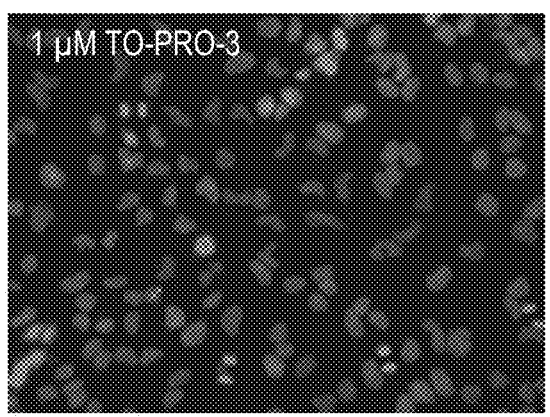
*Fig. 5B*
Photostability
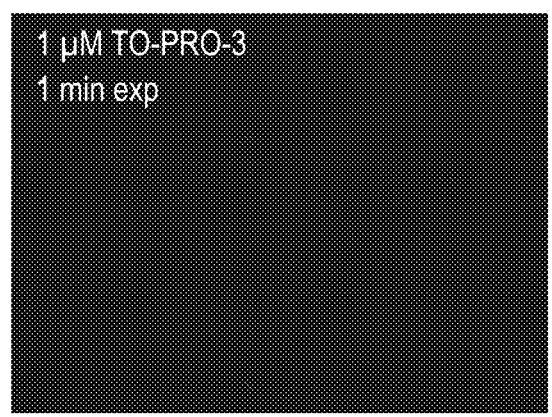
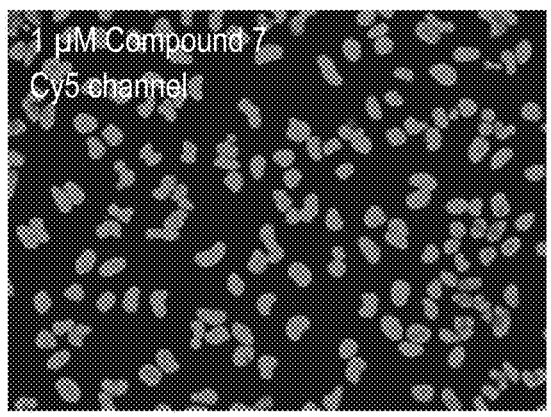
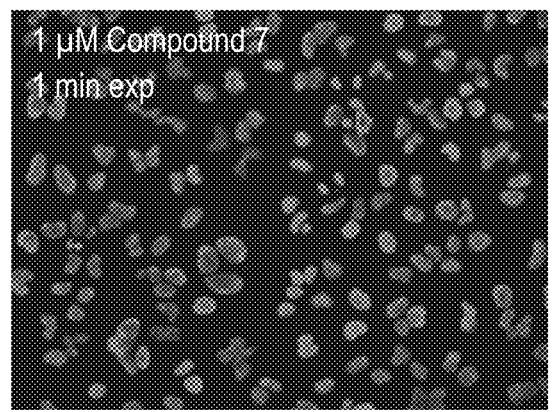
*Fig. 5C*
*Fig. 5D*

Fig. 6A
Fig. 6B
Cy5 channel
DAPI channel
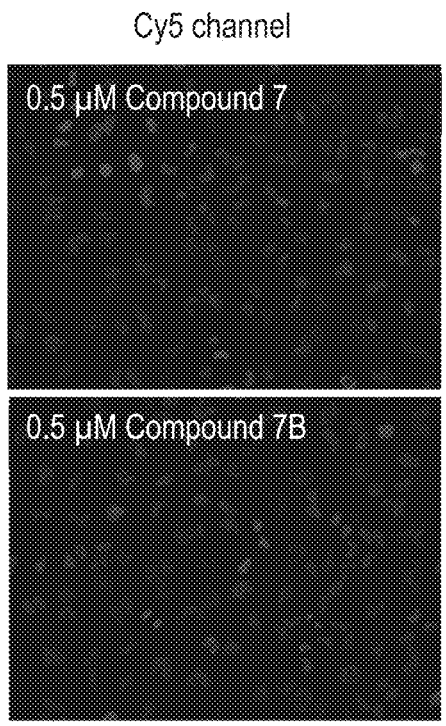
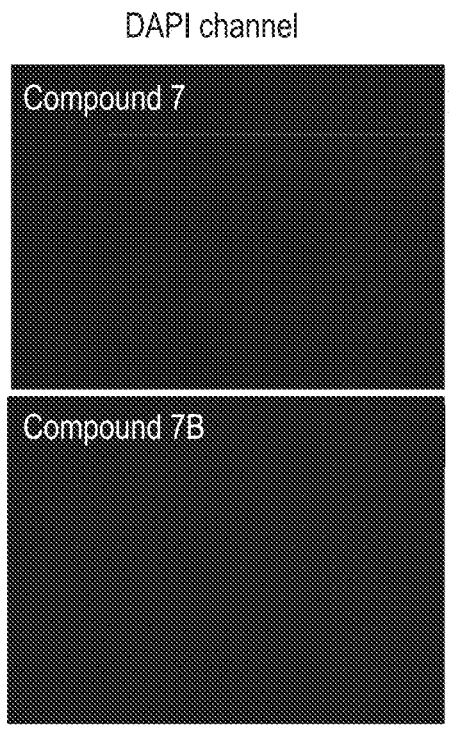
Fig. 6C
Fig. 6D
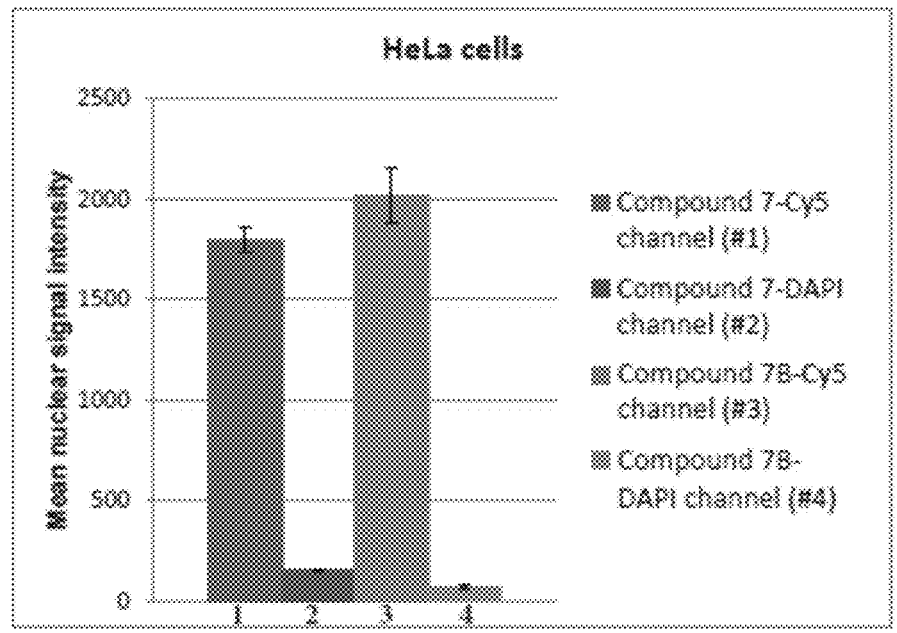
Fig. 6E

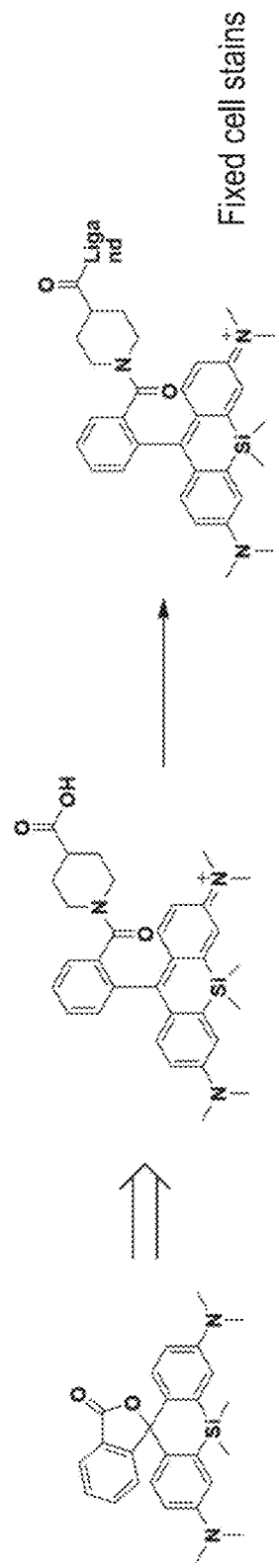
Fig. 10A Fixed cell stains
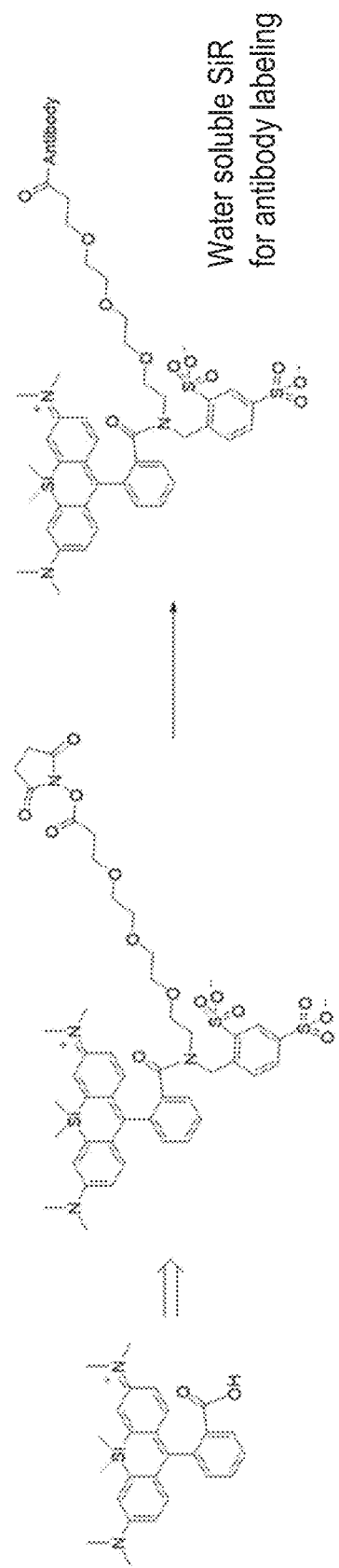
Fig. 10B Water soluble SiR for antibody labeling Alexa Fluor 647

Compound 10A

SILICON-SUBSTITUTED RHODAMINE DYES AND DYE CONJUGATES

CROSS-REFERENCE TO RELATED APPLICATIONS

This application is a 371 National Stage filing of PCT/US2019/045697 filed Aug. 8, 2019, which claims benefit of 62/717,398, filed Aug. 10, 2018 which disclosures are herein incorporated by reference in their entirety.

This disclosure relates to the field of fluorescent dyes and conjugates thereof.

INTRODUCTION AND SUMMARY

In many fields it is useful or necessary to detect or quantify biological material using fluorescent dyes. Biological materials such as nucleic acids, polypeptides, cells, and membranes can be detected in various sample types, e.g., in biomedical, genetic, fermentation, aquaculture, agricultural, forensic and environmental applications. To provide a dye with the desired properties for a particular application, it is often useful or necessary to functionalize or conjugate the dye to a moiety that targets the dye to particular components, such as a given intracellular location, intracellular component (e.g., cytoskeletal component or nucleic acid), or epitope.

Silicon-rhodamine (SiR) dyes can provide bright fluorescence at far red wavelengths and exhibit good photostability, and thus attempts to functionalize or conjugate such dyes have been made for various applications. Such attempts have generally focused on modifying the xanthene moiety of the dye, but such modifications have resulted in significant changes in the photophysical properties of the dye, such as absorption and emission wavelengths, quantum yield and photostability. Accordingly, there is a need for SiR dyes that are or can be modified to improve one or more photophysical properties of the dye, such as absorption and emission wavelengths, quantum yield and photostability.

Described herein are SiR dyes comprising at least one vinyl group attached to the Si atom (10 position) of the SiR dye and derivatives, functionalized versions, conjugates, and uses thereof. Related synthetic methods are also provided. The vinyl group can be derivatized, e.g., using a thiol-ene reaction, to provide functionalized or conjugated SiR dyes. The vinyl-containing and derivatized dyes can have similar photophysical properties to free SiR, and/or have improved properties or characteristics (e.g., specific binding affinity) for biologically relevant targets such as those noted above, provide other benefits, or at least provide the public with a useful choice.

Accordingly, the following are among the embodiments provided herein. Embodiment 1 is a compound of Formula (I):

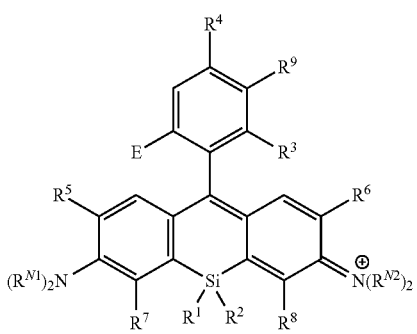

wherein:
$R^1$ is methyl, $C_{2-6}$ alkyl, vinyl, substituted vinyl, $-L^1-R^A$, or $-L^1-R^{B1}$;
$R^2$ is methyl, $C_{2-6}$ alkyl, vinyl, substituted vinyl, $-L^1-R^A$, or $-L^1-R^{B1}$;
or $R^1$ and $R^2$ form a ring together with the silicon to which they are attached;
each $L^1$ is independently a linker;
each $R^A$ is independently a reactive ligand, a solubilizing functionality, a target-binding moiety or a nucleoside/tide moiety;
each $R^{B1}$ is independently a reactive ligand, a solubilizing functionality, a target-binding moiety or nucleoside/tide moiety;
$R^3$ is —COOH, $SO_3^-$, H, $R^{3a}$, $-L^1-R^A$, or $-L^1-R^{B1}$;
$R^{3a}$ is

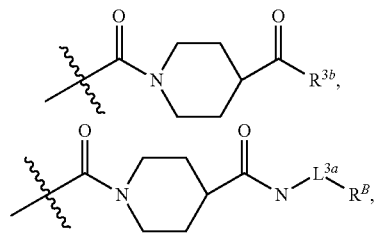

or —C(O)N($R^{N3}$)($R^{N4}$);
$R^{N3}$ is H, methyl, $C_{2-6}$ alkyl, or —$CH_2$-A where A is an aryl or heteroaryl substituted with at least one polar or charged group;
$R^{N4}$ is $-L^1-R^A$, or $-L^1-R^{B1}$, or —$(CH_2CH_2O)_q$—C(O)O—$R^B$ where q is 2, 3, 4, 5, or 6;
$R^{3b}$ is —OH or —N($R^{N5}$)-$L^{3a}$-$R^B$;
each $L^{3a}$ is independently a linker;
$R^B$ is a reactive ligand or a target-binding moiety;
$R^{N5}$ is H, methyl, or $C_{2-6}$ alkyl;
$R^4$ is $SO_3^-$, methyl, chloro, $C_{2-6}$ alkyl, or H;
E is $SO_3^-$, methyl, chloro, $C_{2-6}$ alkyl, or H;
$R^5$ is H, methyl, or $C_{2-6}$ alkyl, or forms a ring with an $R^{N1}$;
$R^6$ is H, methyl, or $C_{2-6}$ alkyl, or forms a ring with an $R^{N2}$;
$R^7$ is H, methyl, or $C_{2-6}$ alkyl, or forms a ring with an $R^{N1}$;
$R^8$ is H, methyl, or $C_{2-6}$ alkyl, or forms a ring with an $R^{N2}$;
$R^9$ is $SO_3^-$, methyl, chloro, $C_{2-6}$ alkyl, or H;
each $R^{N1}$ is independently H, methyl, $C_{2-4}$ alkyl, —C(O)$R^{10}$, —C(O)$R^{13}$, or forms a ring with $R^5$ and/or $R^7$;
each $R^{N2}$ is independently H, methyl, $C_{2-4}$ alkyl, —C(O)$R^{10}$, —C(O)$R^{13}$, or forms a ring with $R^6$ and/or $R^B$;
$R^{10}$ is —C(O)—$CF_3$ or —O—$CH_2$-$A^1$ where $A^1$ is an aryl or heteroaryl optionally substituted with at least one $R^{11}$;
$R^{11}$ is methyl, $C_{2-6}$ alkyl, or —$OR^{12}$; and
$R^{12}$ is H, methyl, acetyl (Ac), acetoxymethyl (AM), —$PO_3^{2-}$, —$PO_3(AM)_2$, or a glycoside;
$R^{13}$ is

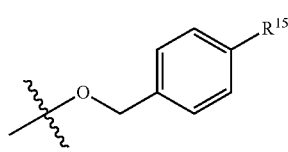

where $R^{15}$ is an oligopeptide or —OR' where R' is acetyl (Ac), AM, $PO_3^{2-}$, $PO_3(AM)_2$, or a glycoside and AM is acetoxymethyl;

further wherein (i) $R^2$ is not methyl or $C_{2-6}$ alkyl if $R^1$ is methyl or $C_{2-6}$ alkyl, OR (ii) $R^3$ is $R^{3a}$ or -$L^1$-$R^{B1}$; or a spirolactone form and/or salt thereof.

Embodiment 2 is a method of preparing a compound of Formula (P2):

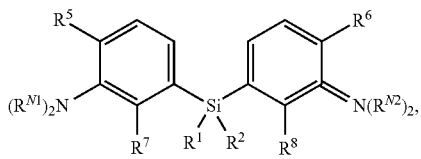

the method comprising reacting compounds of Formula (P1a)

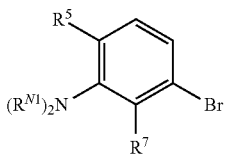

and Formula (P1b)

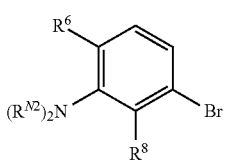

with an organolithium base and then with $SiCl_2R^1R^2$, wherein:

$R^1$ is methyl, $C_{2-6}$ alkyl, vinyl, substituted vinyl, -$L^1$-$R^4$, or -$L^1$-$R^{B1}$;

$R^2$ is methyl, $C_{2-6}$ alkyl, vinyl, substituted vinyl, -$L^1$-$R^4$, or -$L^1$-$R^{B1}$;

or $R^1$ and $R^2$ form a ring together with the silicon to which they are attached; each $L^1$ is independently a linker;

each $R^4$ is independently a reactive ligand, a solubilizing functionality, a target-binding moiety or a nucleoside/tide moiety;

each $R^{B1}$ is independently a reactive ligand, a solubilizing functionality, a target-binding moiety or a nucleoside/tide moiety;

$R^5$ is H, methyl, or $C_{2-6}$ alkyl, or forms a ring with an $R^{N1}$;

$R^6$ is H, methyl, or $C_{2-6}$ alkyl, or forms a ring with an $R^{N2}$;

$R^7$ is H, methyl, or $C_{2-6}$ alkyl, or forms a ring with an $R^{N1}$;

$R^8$ is H, methyl, or $C_{2-6}$ alkyl, or forms a ring with an $R^{N2}$;

each $R^{N1}$ is independently H, methyl, $C_{2-4}$ alkyl, —C(O)$R^{10}$, —C(O)$R^{13}$, or forms a ring with $R^5$ and/or $R^7$;

each $R^{N2}$ is independently H, methyl, $C_{2-4}$ alkyl, —C(O)$R^{10}$, —C(O)$R^{13}$, or forms a ring with $R^6$ and/or $R^B$;

$R^{10}$ is —C(O)—$CF_3$ or —O—$CF_2$-$A^1$ where $A^2$ is an aryl or heteroaryl optionally substituted with at least one $R^{11}$;

$R^{11}$ is methyl, $C_{2-6}$ alkyl, or —$OR^{12}$; and $R^{12}$ is H, methyl, acetyl (Ac), acetoxymethyl (AM), —$PO_3^{2-}$, —$PO_3(AM)_2$, or a glycoside;

$R^{13}$ is

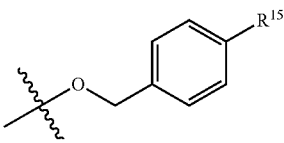

where $R^{15}$ is an oligopeptide or —OR' where R' is acetyl (Ac), AM, $PO_3^{2-}$, $PO_3(AM)_2$, or a glycoside and AM is acetoxymethyl;

thereby producing the compound of Formula (P2).

Embodiment 3 is a method of preparing a compound of Formula (I):

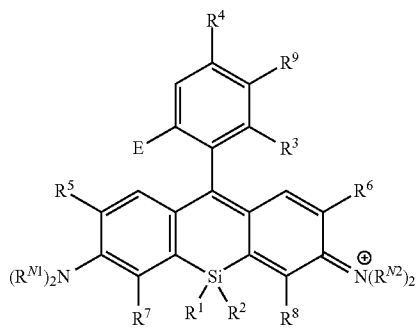

comprising reacting a compound of Formula (P2)

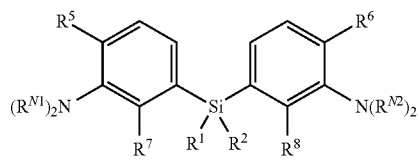

with a compound of Formula (P2a)

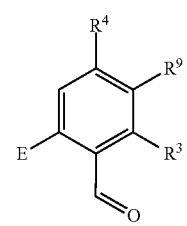

in the presence of $CuBr_2$ at a temperature above 100° C., wherein:

$R^1$ is methyl, $C_{2-6}$ alkyl, vinyl, substituted vinyl, -$L^1$-$R^4$, or -$L^1$-$R^{B1}$;

$R^2$ is methyl, $C_{2-6}$ alkyl, vinyl, substituted vinyl, -$L^1$-$R^4$, or -$L^1$-$R^{B1}$;

or $R^1$ and $R^2$ form a ring together with the silicon to which they are attached;

each $L^1$ is independently a linker;
each $R^A$ is independently a reactive ligand, a solubilizing functionality, a target-binding moiety or a nucleoside/tide moiety;
each $R^{B1}$ is independently a reactive ligand, a solubilizing functionality, a target-binding moiety or a nucleoside/tide moiety;
$R^3$ is —COOH, $SO_3^-$, H, $R^{3a}$, -$L^1$-$R^A$, or -$L^1$-$R^{B1}$;
$R^{3a}$ is

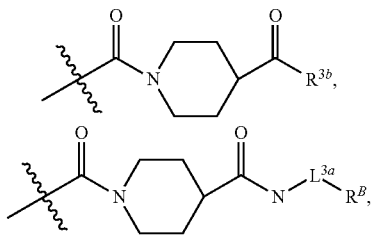

or —C(O)N($R^{N3}$)($R^{N4}$);
$R^{N3}$ is H, methyl, $C_{2-6}$ alkyl, or —CH$_2$-A where A is an aryl or heteroaryl substituted with at least one polar or charged group;
$R^{N4}$ is -$L^1$-$R^A$, or -$L^1$-$R^{B1}$, or —(CH$_2$CH$_2$O)$_q$—C(O)O—$R^B$ where q is 2, 3, 4, 5, or 6;
$R^{3b}$ is —OH or —N($R^{N5}$)-$L^{3a}$-$R^B$;
each $L^{3a}$ is independently a linker;
$R^B$ is a reactive ligand or a target-binding moiety;
$R^{N5}$ is H, methyl, or $C_{2-6}$ alkyl;
$R^4$ is $SO_3^-$, methyl, chloro, $C_{2-6}$ alkyl, or H;
E is $SO_3^-$, methyl, chloro, $C_{2-6}$ alkyl, or H;
$R^5$ is H, methyl, or $C_{2-6}$ alkyl, or forms a ring with an $R^{N1}$;
$R^6$ is H, methyl, or $C_{2-6}$ alkyl, or forms a ring with an $R^{N2}$;
$R^7$ is H, methyl, or $C_{2-6}$ alkyl, or forms a ring with an $R^{N1}$;
$R^8$ is H, methyl, or $C_{2-6}$ alkyl, or forms a ring with an $R^{N2}$;
$R^9$ is $SO_3^-$, methyl, chloro, $C_{2-6}$ alkyl, or H;
each $R^{N1}$ is independently H, methyl, $C_{2-4}$ alkyl, C(O)$R^{10}$, —C(O)$R^{13}$, or forms a ring with $R^5$ and/or $R^7$;
each $R^{N2}$ is independently H, methyl, $C_{2-4}$ alkyl, C(O)$R^{10}$, —C(O)$R^{13}$, or forms a ring with $R^6$ and/or $R^8$;
$R^{10}$ is —C(O)—CF$_3$ or —O—CH$_2$-$A^1$ where $A^1$ is an aryl or heteroaryl optionally substituted with at least one $R^{11}$;
$R^{11}$ is methyl, $C_{2-6}$ alkyl, or —O$R^{12}$; and
$R^{12}$ is H, methyl, acetyl (Ac), acetoxymethyl (AM), —PO$_3^{2-}$, —PO$_3$(AM)$_2$, or a glycoside;
$R^{13}$ is

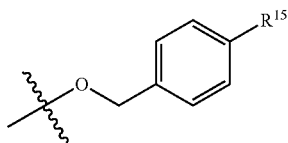

where $R^{15}$ is an oligopeptide or —OR' where R' is acetyl, AM, PO$_3^{2-}$, PO$_3$(AM)$_2$, or a glycoside and AM is acetoxymethyl;
further wherein (i) $R^2$ is not methyl or $C_{2-6}$ alkyl if $R^1$ is methyl or $C_{2-6}$ alkyl, OR (ii) $R^3$ is $R^{3a}$ or -$L^1$-$R^{B1}$;
thereby producing the compound of Formula (I).

Embodiment 4 is the compound or method of any one of the preceding embodiments, wherein $R^1$ or $R^2$ is vinyl or substituted vinyl.

Embodiment 5 is the compound or method of any one of the preceding embodiments, wherein $R^1$ or $R^2$ is vinyl.

Embodiment 6 is the compound or method of any one of the preceding embodiments, wherein $R^1$ or $R^2$ is vinyl substituted with methyl or $C_{2-6}$ alkyl.

Embodiment 7 is the compound or method of any one of embodiments 1-3, wherein $R^1$ and $R^2$ form a ring together with the silicon to which they are attached.

Embodiment 8 is the compound or method of embodiment 7, wherein the ring is a saturated ring.

Embodiment 9 is the compound or method of embodiment 7 or 8, wherein the ring is a 5-, 6-, or 7-membered ring.

Embodiment 10 is the compound or method of any one of embodiments 7-9, wherein the ring is unsubstituted.

Embodiment 11 is the compound or method of any one of embodiments 1-6, wherein $R^1$ or $R^2$ is -$L^1$-$R^A$.

Embodiment 12 is the compound or method of embodiment 11, wherein $R^A$ is —COOH.

Embodiment 13 is the compound or method of embodiment 11, wherein $R^A$ is

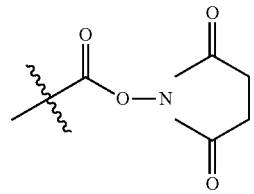

(e.g., NHS ester or succinimidyl ester (SE)), carboxyl, carboxylester, maleimide, amide, sulfodichlorophenyl (SDP) ester, sulfotetrafluorophenyl (STP) ester, tetrafluorophenyl (TFP) ester, pentafluorophenyl (PFP) ester, acetoxymethyl (AM) ester, nitrilotriacetic acid (NTA), aminodextran and cyclooctyne-amine.

Embodiment 14 is the compound or method of embodiment 11, wherein $R^A$ is a solubilizing functionality.

Embodiment 15 is the compound or method of embodiment 14, wherein the solubilizing functionality comprises at least 1, 2, 3, 4, 5, 6, 7, 8, 9 or 10 ethylene oxide units.

Embodiment 16 is the compound or method of embodiment 11, wherein $R^A$ comprises a phosphoramidite.

Embodiment 17 is the compound or method of any one of embodiments 1-6 or 11-16, wherein $R^1$ or $R^2$ is -$L^1$-$R^{B1}$.

Embodiment 18 is the compound or method of embodiment 17, wherein $R^{B1}$ comprises a nucleic acid binding moiety.

Embodiment 19 is the compound or method of embodiment 17, wherein $R^{B1}$ comprises a cytoskeleton-binding moiety.

Embodiment 20 is the compound or method of embodiment 17, wherein $R^{B1}$ comprises

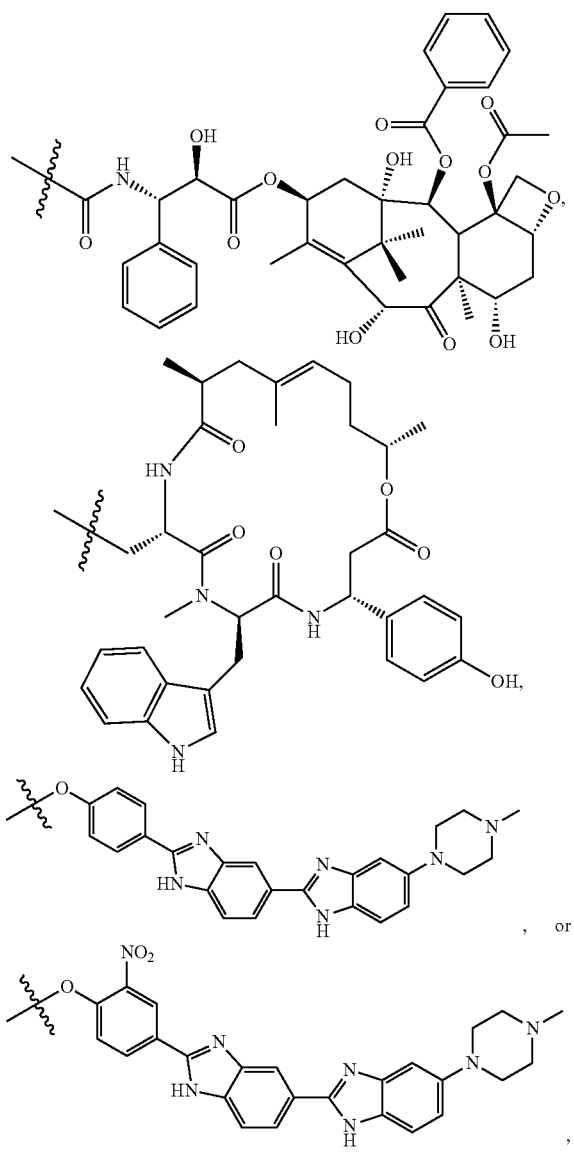

, or where the wavy line indicates the connection to the SiR moiety, optionally through a linker.

Embodiment 21 is the compound or method of embodiment 17, wherein $R^{B1}$ comprises an antibody.

Embodiment 22 is the compound or method of any one of the preceding embodiments, wherein each $L^1$ is independently —$(CH_2)_s$—X-$L^{3a}$-, where s is independently 2, 3, 4, 5, or 6; each X is independently $CH_2$, S, S(O), or $S(O)_2$; and each $L^{3a}$ is independently —$(CH_2)_p$— where p is 0, 1, 2, 3, 4, 5, or 6.

Embodiment 23 is the compound or method of embodiment 22, wherein s is 2.

Embodiment 24 is the compound or method of embodiment 22 or 23, wherein X is S.

Embodiment 25 is the compound or method of embodiment 22 or 23, wherein X is S(O).

Embodiment 26 is the compound or method of any one of embodiments 22-25, wherein each $L^{3a}$ is —$(CH_2)_p$— where p is 2.

Embodiment 27 is the compound or method of any one of embodiments 22-25, wherein each $L^{3a}$ is —$(CH_2)_p$- where p is 3.

Embodiment 28 is the compound or method of any one of embodiments 22-25, wherein each $L^{3a}$ is —$(CH_2)_p$— where p is 4, 5, or 6.

Embodiment 29 is the compound or method of any one of the preceding embodiments, wherein $R^3$ is —COOH.

Embodiment 30 is the compound or method of any one of embodiments 1-28, wherein $R^3$ is $SO_3^-$.

Embodiment 31 is the compound or method of any one of embodiments 1-28, wherein $R^3$ is H.

Embodiment 32 is the compound or method of any one of embodiments 1-28, wherein $R^3$ is $R^{3a}$.

Embodiment 33 is the compound or method of embodiment 32, wherein $R^{3a}$ is —$C(O)N(R^{N3})(R^{N4})$.

Embodiment 34 is the compound or method of embodiment 33, wherein $R^{N3}$ is methyl.

Embodiment 35 is the compound or method of embodiment 33, wherein $R^{N3}$ is —$CH_2$-A where A is an aryl or heteroaryl substituted with at least two polar or charged groups.

Embodiment 36 is the compound or method of embodiment 33 or 35, wherein $R^{N3}$ is —$CH_2$-A where A is an aryl or heteroaryl substituted with at least one —OH, —$NH_2$, —COOH, —$NO_2$, or —$SO_3^-$.

Embodiment 37 is the compound or method of embodiment 33, 35 or 36, wherein $R^{N3}$ is —$CH_2$-A where A is an aryl or heteroaryl substituted with at least two groups which are independently —OH, —$NH_2$, —COOH, —$NO_2$, or —$SO_3^-$.

Embodiment 38 is the compound or method of any one of embodiments 35-37, wherein $R^{N3}$ is —$CH_2$-A where A is an aryl or heteroaryl substituted with at least two —$SO_3^-$ groups.

Embodiment 39 is the compound or method of any one of embodiments 33 or 35-38, where A is a substituted aryl.

Embodiment 40 is the compound or method of any one of embodiments 33-39, wherein $R^{N4}$ is —$(CH_2)_3$—$R^B$, optionally wherein the $R^B$ of $R^{N4}$ is —COOH.

Embodiment 41 is the compound or method of any one of embodiments 33-39, wherein $R^{N4}$ is —$(CH_2CH_2O)_q$—$C(O)O$—$R^B$ where q is 2.

Embodiment 42 is the compound or method of any one of embodiments 33-39, wherein $R^{N4}$ is —$(CH_2CH_2O)_q$—$C(O)O$—$R^B$ where q is 3.

Embodiment 43 is the compound or method of any one of embodiments 33-39, wherein $R^{N4}$ is —$(CH_2CH_2O)_q$—$C(O)O$—$R^B$ where q is 4, 5, or 6.

Embodiment 44 is the compound or method of embodiment 32, wherein $R^{3a}$ is

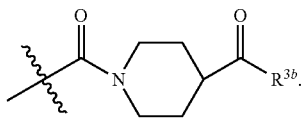

Embodiment 45 is the compound or method of embodiment 44, wherein $R^{3b}$ is $N(R^{N5})$-$L^{3a}$-$R^B$.

Embodiment 46 is the compound or method of embodiment 45, wherein $R^{N5}$ is H.

Embodiment 47 is the compound or method of embodiment 45, wherein $R^{N5}$ is methyl.

Embodiment 48 is the compound or method of any one of embodiments 44-47, wherein $R^{3b}$ is —OH.

Embodiment 49 is the compound or method of embodiment 32, wherein $R^{3a}$ is

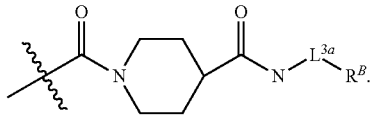

Embodiment 50 is the compound or method of any one of embodiments 45-49, wherein each $L^{3a}$ is —$(CH_2)_p$— where p is 2.

Embodiment 51 is the compound or method of any one of embodiments 45-49, wherein each $L^{3a}$ is —$(CH_2)_p$- where p is 3.

Embodiment 52 is the compound or method of any one of embodiments 45-49, wherein each $L^{3a}$ is independently —$(CH_2)_p$— where p is 4, 5, or 6.

Embodiment 53 is the compound or method of any one of the preceding embodiments, wherein $R^B$ comprises a reactive ligand, optionally wherein the reactive ligand is a carboxyl, amine, maleimide, or active ester, further optionally wherein the active ester is an NHS ester or succinimidyl ester (SE), sulfodichlorophenyl (SDP) ester, sulfotetrafluorophenyl (STP) ester, tetrafluorophenyl (TFP) ester or pentafluorophenyl (PFP) ester.

Embodiment 56 is the compound or method of any one of embodiments 1-52, wherein $R^B$ comprises a phosphoramidite.

Embodiment 55 is the compound or method of any one of embodiments 1-52, wherein $R^B$ comprises a nucleic acid-binding moiety.

Embodiment 56 is the compound or method of any one of embodiments 1-52, wherein $R^B$ comprises a cytoskeleton-binding moiety.

Embodiment 57 is the compound or method of any one of embodiments 1-52, wherein $R^B$ comprises

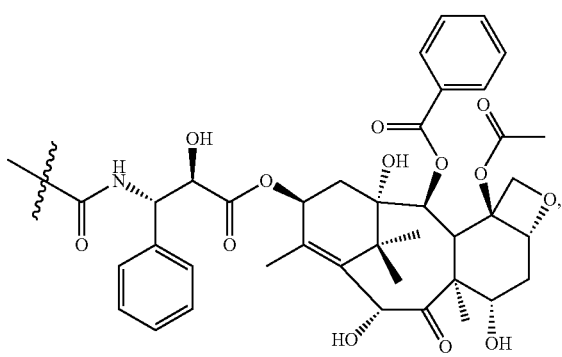

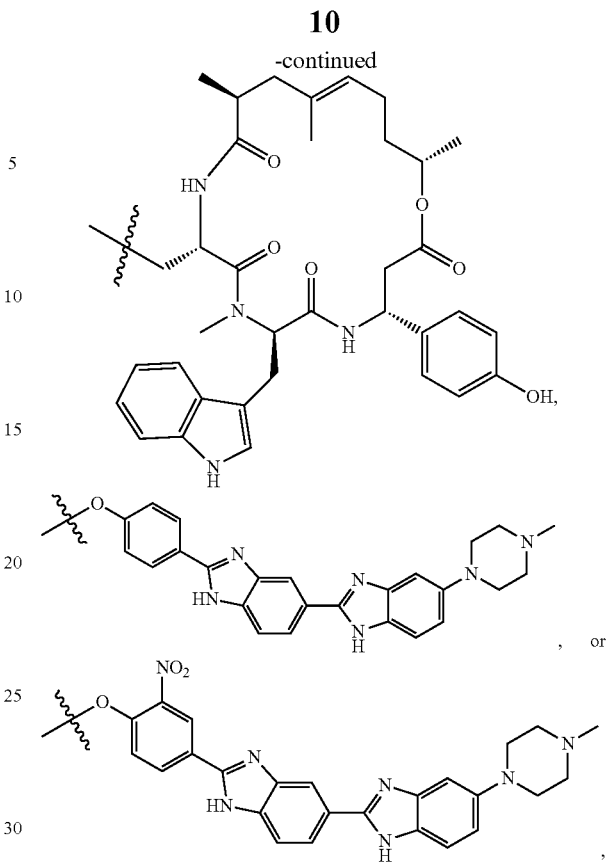

where the wavy line indicates the connection to the SiR moiety, optionally through a linker.

Embodiment 58 is the compound or method of any one of embodiments 1-52, wherein $R^B$ comprises an antibody.

Embodiment 59 is the compound or method of any one of the preceding embodiments, wherein $R^4$ is $SO_3^-$.

Embodiment 60 is the compound or method of any one of embodiments 1-58, wherein $R^4$ is H.

Embodiment 61 is the compound or method of any one of the preceding embodiments, wherein E and $R^9$ are each chloro.

Embodiment 62 is the compound or method of any one of embodiments 1-60, wherein E and $R^9$ are each H.

Embodiment 63 is the compound or method of any one of the preceding embodiments, wherein $R^5$ is H.

Embodiment 64 is the compound or method of any one of embodiments 1-62, wherein $R^5$ is methyl.

Embodiment 65 is the compound or method of any one of embodiments 1-62, wherein $R^5$ forms a 5- or 6-membered ring with an $R^{N1}$.

Embodiment 66 is the compound or method of any one of the preceding embodiments, wherein $R^6$ is H.

Embodiment 67 is the compound or method of any one of embodiments 1-65, wherein $R^6$ is methyl.

Embodiment 68 is the compound or method of any one of embodiments 1-65, wherein $R^6$ forms a 5- or 6-membered ring with an $R^{N2}$.

Embodiment 69 is the compound or method of any one of the preceding embodiments, wherein $R^7$ is H.

Embodiment 70 is the compound or method of any one of embodiments 1-68, wherein $R^7$ is methyl.

Embodiment 71 is the compound or method of any one of embodiments 1-68, wherein $R^7$ forms a 5- or 6-membered ring with an $R^{N1}$.

Embodiment 72 is the compound or method of any one of the preceding embodiments, wherein $R^8$ is H.

Embodiment 73 is the compound or method of any one of embodiments 1-71, wherein $R^B$ is methyl.

Embodiment 74 is the compound or method of any one of embodiments 1-71, wherein $R^B$ forms a 5- or 6-membered ring with an $R^{N2}$.

Embodiment 75 is the compound or method of any one of the preceding embodiments, wherein one or each $R^{N1}$ is H.

Embodiment 76 is the compound or method of any one of the preceding embodiments, wherein one or each $R^{N1}$ is methyl or $C_{2-4}$ alkyl.

Embodiment 77 is the compound or method of any one of the preceding embodiments, wherein one or each $R^{N1}$ is —C(O)OR$^{10}$.

Embodiment 78 is the compound or method of any one of embodiments 1-62 or 65-67, wherein an $R^{N1}$ forms a 5- or 6-membered ring with $R^5$.

Embodiment 79 is the compound or method of any one of embodiments 1-68 or 71-78, wherein an $R^{N1}$ forms a 5- or 6-membered ring with $R^7$.

Embodiment 80 is the compound or method of any one of the preceding embodiments, wherein one or each $R^{N2}$ is H.

Embodiment 81 is the compound or method of any one of the preceding embodiments, wherein one or each $R^{N2}$ is methyl.

Embodiment 82 is the compound or method of any one of the preceding embodiments, wherein one or each $R^{N2}$ is $C_{2-4}$ alkyl.

Embodiment 83 is the compound or method of any one of the preceding embodiments, wherein one or each $R^{N2}$ is —C(O)OR$^{10}$.

Embodiment 84 is the compound or method of any one of the preceding embodiments, wherein an $R^{N2}$ forms a 5- or 6-membered ring with $R^6$.

Embodiment 85 is the compound or method of any one of embodiments 1-65 or 68-84, wherein an $R^{N2}$ forms a 5- or 6-membered ring with $R^B$.

Embodiment 86 is the compound or method of any one of embodiments 1-72 or 75-85, wherein $R^{10}$ is —CH$_2$-A$^1$ where A$^1$ is an aryl optionally substituted with at least one $R^{11}$.

Embodiment 87 is the compound or method of any one of the preceding embodiments, wherein $R^{11}$ is methyl.

Embodiment 88 is the compound or method of any one of embodiments 1-86, wherein $R^{11}$ is —OR$^{12}$.

Embodiment 89 is the compound or method of any one of embodiments 1-86 or 88, wherein $R^{12}$ is H.

Embodiment 90 is the compound or method of any one of embodiments 1-88, wherein $R^{12}$ is methyl.

Embodiment 91 is the compound or method of any one of embodiments 1-88, wherein $R^{12}$ is acetyl (Ac).

Embodiment 92 is the compound or method of any one of embodiments 1-88, wherein $R^{12}$ is acetoxymethyl (AM).

Embodiment 93 is the compound or method of any one of embodiments 1-88, wherein $R^{12}$ is —PO$_3^{2-}$.

Embodiment 94 is the compound or method of any one of embodiments 1-88, wherein $R^{12}$ is —PO$_3$(AM)$_2$.

Embodiment 95 is the compound or method of any one of embodiments 1-88, wherein $R^{12}$ is a glycoside.

Embodiment 96 is the compound or method of any one of the preceding embodiments, wherein an $R^{N1}$ or $R^{N2}$ is —C(O)R$^{13}$, optionally wherein only one of $R^{N1}$ or $R^{N2}$ is —C(O)R$^{13}$.

Embodiment 97 is the compound or method of any one of the preceding embodiments, wherein $R^{15}$ is an oligopeptide recognized by a protease, optionally wherein the protease is a caspase.

Embodiment 98 is the compound or method of any one of the preceding embodiments, wherein $R^{15}$ is a tetrapeptide, pentapeptide, hexapeptide, heptapeptide, octopeptide, or nonapeptide.

Embodiment 99 is the compound or method of any one of the preceding embodiments, wherein $R^{15}$ comprises the amino acid sequence DVED.

Embodiment 100 is the compound or method of any one of the preceding embodiments, wherein $R^{15}$ comprises the amino acid sequence DVEDHN.

Embodiment 101 is the compound or method of any one of the preceding embodiments, wherein $R^{15}$ is an oligopeptide linked through its C-terminus to the ring of $R^{13}$.

Embodiment 102 is the compound or method of any one of the preceding embodiments, wherein $R^1$ or $R^2$ is methyl or $C_{2-6}$ alkyl.

Embodiment 103 is the compound or method of any one of the preceding embodiments, wherein one, two, or three of the following are true:
embodiment 104 is $R^5$ and $R^6$ are identical;
embodiment 105 is an $R^{N1}$ is identical to an $R^{N2}$; or
embodiment 106 is $R^7$ and $R^8$ are identical.

Embodiment 107 is the compound or method of any one of the preceding embodiments, each $R^{N1}$ is identical to an $R^{N2}$.

Embodiment 108 is the compound or method of any one of the preceding embodiments, wherein the compound has a plane of mirror symmetry passing through the silicon and $R^4$, optionally with the exception that $R^1$ and $R^2$ are not necessarily identical.

Embodiment 109 is the compound or method of any one of the preceding embodiments, having the structure:

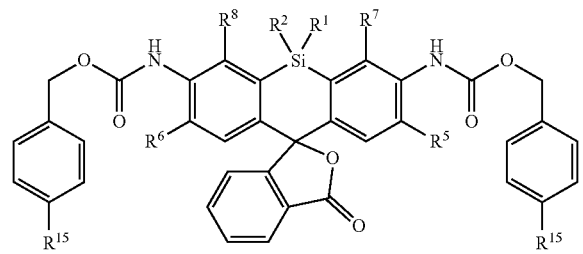

or an open form, salt, or free acid thereof.

Embodiment 110 is the compound or method of any one of the preceding embodiments, wherein the compound is a labeled nucleoside/tide having the formula:

NUC-DYE wherein
NUC is a nucleoside/tide moiety;
DYE is the SiR moiety of the compound, NUC and DYE being connected by a linker;
wherein the linker is attached to DYE at one of positions $R^1$ or $R^2$ of Formula (I); optionally wherein if NUC comprises a purine base, the linker is attached to the 8-position of the purine, if NUC comprises a 7-deazapurine base, the linker is attached to the 7-position of the 7-deazapurine, and if NUC comprises a pyrimidine base, the linker is attached to the 5-position of the pyrimidine.

Embodiment 111 is the compound or method of embodiment 110, wherein NUC comprises a nucleotide triphosphate, primer, primer extension product, or probe.

Embodiment 112 is the compound or method of embodiment 110 or 111, further comprising a quencher or fluorophore in an energy-transfer relationship with the SiR moiety of the compound.

Embodiment 113 is the compound or method of any one of embodiments 110-112, wherein NUC comprises a base selected from the group consisting of uracil, cytosine, deazaadenine, and deazaguanosine.

Embodiment 114 is the compound or method of any one of embodiments 1-108, wherein the compound is a phosphoramidite compound of Formula (L1):

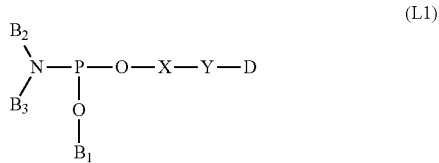

wherein:
X and Y together form a linker;
$B_1$ is a phosphite ester protecting group;
$B_2$ and $B_3$ taken separately are lower alkyl, lower alkene, aryl, and cycloalkyl containing up to 10 carbon atoms; and
D is the SiR moiety of the compound;
wherein Y is attached to D at one of positions $R^1$ or $R^2$ of Formula (I).

Embodiment 115 is the compound or method of any one of embodiments 1-108, wherein the compound is a phosphoramidite compound of Formula (L2):

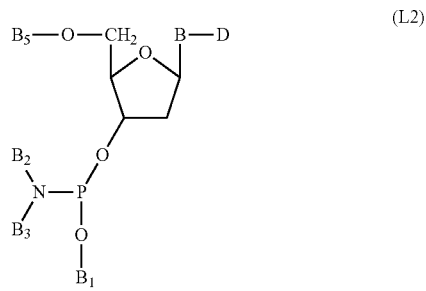

wherein:
$B_1$ is a phosphite ester protecting group;
$B_2$ and $B_3$ taken separately are lower alkyl, lower alkene, aryl, or cycloalkyl containing up to 10 carbon atoms;
$B_5$ is hydrogen or an acid-cleavable hydroxyl protecting group;
B is a nucleoside/tide base;
D is the SiR moiety of the compound;
B is attached to D through a linker to one of positions $R^1$ or $R^2$ of Formula (I);
optionally wherein if B is purine or 7-deazapurine, the sugar moiety is attached at the $N^9$-position of the purine or 7-deazapurine, and if B is pyrimidine, the sugar moiety is attached at the $N^1$-position of the pyrimidine;
optionally wherein if B is a purine, the linker is attached to the 8-position of the purine, if B is 7-deazapurine, the linker is attached to the 7-position of the 7-deazapurine, and if B is pyrimidine, the linker is attached to the 5-position of the pyrimidine.

Embodiment 116 is the compound or method of any one of embodiments 1-115, wherein the compound which is any one of compounds 1, 1A, 1B, 1C, 2, 2A, 3, 4A, 5, 6, 7, 7A, 7B, 8, 9, 10A, 10B, 11, 12, 13, 14, 15, 16, 17, 18, 19, 20, 21, 22, 23, 24, 25, 26, 27, 28, 29, 30, 31, 32, 33, 34, 35, 36, 37, 38, 39, 43, 45, 46, 47, 48, 49, 50, 51, 52, 53, 54, 55, 56, 57, 58, and 59, or an open or spirolactone form and/or salt or free acid thereof.

Embodiment 117 is a compound formed by reacting a first compound which is any one of compounds 1, 1A, 1B, 1C, 2, 2A, 3, 4A, 5, 6, 7, 7A, 7B, 8, 9, 10A, 10B, 11, 12, 13, 14, 15, 16, 17, 18, 19, 20, 21, 22, 23, 24, 25, 26, 27, 28, 29, 30, 31, 32, 33, 34, 35, 36, 37, 38, 39, 43, 45, 46, 47, 48, 49, 50, 51, 52, 53, 54, 55, 56, 57, 58, and 59 with a target-binding moiety, nucleoside/tide, or polynucleotide, optionally wherein the first compound is first activated by converting a moiety thereof to a reactive ligand that reacts with the target-binding moiety; or an open or spirolactone form and/or salt or free acid thereof.

Embodiment 118 is the compound of embodiment 117, wherein the target-binding moiety is an antibody, nucleic acid-binding moiety, or cytoskeleton-binding moiety.

Embodiment 119 is a method of detecting a target polynucleotide, comprising contacting a sample comprising or suspected of comprising the target polynucleotide with a compound of any one of embodiments 1 or 4-117 which is capable of specifically binding the target polynucleotide, and determining whether a complex comprising the target polynucleotide and the compound was formed.

Embodiment 120 is the compound or method of embodiment 119, wherein determining whether a complex comprising the target polynucleotide and the compound was formed comprises detecting fluorescence from the complex or detecting a change in fluorescence resulting from complex formation, optionally wherein the change in fluorescence resulting from complex formation is a reduction of quenching by a quencher due to cleavage or a conformational change.

Embodiment 121 is a method of sequencing a polynucleotide, comprising contacting the polynucleotide with the compound of any one of embodiments 1, 4-108 or 110-117 during a sequencing reaction, forming a sequencing product, and detecting fluorescence from the sequencing product, wherein the compound comprises a primer or nucleotide triphosphate.

Embodiment 122 is the compound or method of embodiment 121, wherein the compound is a labeled terminator nucleotide or dinucleotide that terminates synthesis of the sequencing product, optionally wherein the labeled terminator nucleotide is a labeled dideoxynucleotide or a reversible terminator nucleotide or dinucleotide.

Embodiment 123 is the compound or method of embodiment 121, wherein the compound is a primer and the sequencing product is formed by primer extension.

Embodiment 124 is the compound or method of any one of embodiments 121-123, wherein the method comprises separating the sequencing product from other sequencing products before detecting fluorescence, optionally wherein the separating is by electrophoresis, further optionally wherein the electrophoresis is capillary electrophoresis.

Embodiment 125 is the compound or method of any one of embodiments 121-123, wherein the method comprises detecting the sequencing product in situ.

Embodiment 126 is a method of labeling a nucleotide or polynucleotide comprising a first reactive ligand, the method comprising reacting the nucleotide or polynucleotide with a compound of any one of embodiments 1, 4-108 or 110-117 comprising a second reactive ligand capable of forming a bond upon reaction with the first reactive ligand.

Embodiment 127 is the compound or method of embodiment 126, wherein the second reactive ligand is a phosphoramidite.

Embodiment 128 is the compound or method of embodiment 126, wherein the second reactive ligand is an active ester, optionally wherein the active ester is an NHS ester.

Embodiment 129 is a method of staining a polynucleotide comprising contacting the polynucleotide with a compound of any one of embodiments 1, 4-108 or 110-117 that comprises a polynucleotide-binding moiety.

Embodiment 130 is a fluorescent complex comprising a compound of any one of embodiments 1, 4-108 or 110-117 that comprises a polynucleotide-binding moiety non-covalently associated with a polynucleotide.

Embodiment 131 is the method of embodiment 129 or the fluorescent complex of embodiment 130, wherein the polynucleotide has a length of about 8 to about 15 nucleotides, about 15 to about 30 nucleotides, about 30 to about 50 nucleotides, about 50 to about 200 nucleotides, about 200 to about 1000 nucleotides, about 1 kb to about 5 kb, about 5 kb to about 10 kb, about 10 kb to about 50 kb, about 50 kb to about 500 kb, about 500 kb to about 5 Mb, about 5 Mb to about 50 Mb, or about 50 Mb to about 500 Mb.

Embodiment 132 is the method or fluorescent complex of any one of embodiments 119-131, wherein the nucleic acid is a plasmid, cosmid, PCR product, restriction fragment, cDNA, genomic DNA, or a natural or synthetic oligonucleotide.

Embodiment 133 is the method or fluorescent complex of any one of embodiments 119-132, wherein the polynucleotide is in an electrophoresis gel, a cell, an organelle, virus, viroid, or biological fluid, or is in or was obtained from a water sample, soil sample, foodstuff, fermentation process, or surface wash.

Embodiment 134 is a method of determining cell membrane integrity, the method comprising:
 a) incubating a sample containing one or more cells with a compound of any one of embodiments 1, 4-109 or 116-118 for a time sufficient for the compound to enter cells with compromised cell membranes; and
 b) determining cell membrane integrity of the one or more cells based on presence of a detectable fluorescent signal from the one or more cells, where the presence of the detectable fluorescent signal indicates that the cell membrane integrity is compromised and the absence of the detectable fluorescent signal indicates that the cell membrane integrity is intact.

Embodiment 135 is a method of detecting a target, comprising contacting a sample comprising or suspected of comprising the target with a compound of any one of embodiments 1, 4-109 or 116-118 that comprises a target-binding moiety that specifically binds the target and detecting fluorescence from a complex comprising the target and the compound.

Embodiment 136 is the compound or method of embodiment 135, wherein the sample comprises cells.

Embodiment 137 is the compound or method of embodiment 135, wherein the sample comprises a biological extract.

Embodiment 138 is the compound or method of any one of embodiments 134-137, wherein detecting fluorescence is performed using a fluorescence microscope, plate reader, fluorescence scanner, fluorometer, or flow cytometer.

Embodiment 139 is a kit for detecting a target, comprising a compound of any one of embodiments 1 or 4-117 that comprises a target-binding moiety configured to specifically bind the target.

Embodiment 140 is the kit of embodiment 139, wherein the target is actin or microtubules and the target-binding moiety is an actin-binding moiety or a microtubule-binding moiety.

Embodiment 141 is the kit of embodiment 139, wherein the target-binding moiety is an antibody specific for the target.

Embodiment 142 is the kit of embodiment 139, wherein the target is a primary antibody and the target-binding moiety is a secondary antibody specific for the primary antibody.

Embodiment 143 is the kit of any one of embodiments 139-141, wherein the target is a polypeptide, polysaccharide, lipid, or polynucleotide.

Embodiment 144 is a kit for staining a sample, comprising a compound of any one of embodiments 1 or 4-118.

Embodiment 145 is a kit for conjugating a compound of Formula (I) to a target-binding moiety, nucleotide, or polynucleotide, comprising a compound of any one of embodiments 1 or 4-118 that comprises at least one reactive ligand.

BRIEF DESCRIPTION OF THE DRAWINGS

FIG. 1A shows the structures of Compounds 1, 1A, 1B, 1C, 2, and 2A. FIG. 1L shows the structure of Compound 43. FIG. 1M shows the structures of Compounds 45 and 46. FIG. 1O shows the structures of Compounds 51 and 52. FIG. 1R illustrates the fluorescent zwitterionic open form of a generic SiR compound on the left and the non-fluorescent spiro closed form of the same generic SiR compound on the right.

FIG. 2A shows a synthetic route to an SiR compound according to known methods. FIG. 2B shows an exemplary synthetic scheme for compounds 1-3 according to embodiments provided herein, which can be used in conjugation reactions to various ligands according to certain embodiments provided herein (compound 3 can be produced by oxidation of Compound 2 using known methods). FIG. 2C shows an exemplary preparation of Compound 2A from Compound 2, which can be used in conjugation reactions such as those indicated according to certain embodiments provided herein. FIG. 2D shows the structures of a nuclear dye for live cells (Compound 4), a tubulin probe (Compound 5), and an actin probe (Compound 6) that can be prepared from Compound 2 (e.g., via Compound 2A) according to certain embodiments provided herein. FIG. 2E shows an exemplary synthetic scheme for Compound 7B via Compound 7A according to certain embodiments provided herein.

FIG. 3A shows cells stained with 1 μM SiR-Hoechst. FIG. 3B shows cells stained with 2 μM SiR-Hoechst. FIG. 3C shows cells stained with 1 μM Compound 4. FIG. 3D shows cells stained with 2 μM Compound 4. FIG. 3E shows a bar plot comparing the observed nuclear signal intensity of cells stained with SiR-Hoechst and Compound 4. The nuclear signal intensity was determined by averaging the fluorescence intensity in nuclei for each stain and concentration tested.

FIGS. 4A-4D show a comparison of cells stained with tubulin probes using docetaxel (Taxol) as the targeting ligand. Two fields are shown for each dye. The cells were stained with 0.5 μM Compound 5 or SiR-Taxol (Spirochrome, Switzerland) and imaging was performed. FIGS. 4A-B show cells stained with Compound 5. FIGS. 4C-D show cells stained with SiR-Taxol.

FIGS. 5A-5D show a comparison of the fluorescence intensity and photostability of Compound 7 and TO-PRO-3. Fixed A459 cells were stained with 1 μM Compound 7 or TO-PRO-3 and images collected using the Cy5 channel of a fluorescence microscope. Cells staining positive appear as light gray objects on a black background. FIG. 5A shows staining with 1 μM TO-PRO-3. FIG. 5C shows staining with 1 μM Compound 7. FIG. 5B shows TO-PRO-3 fluorescence after a 1 minute exposure to excitation light from the Cy5 channel (little to no fluorescence was observable). FIG. 5D shows Compound 7 fluorescence after a 1 minute exposure to excitation light from the Cy5 channel.

FIGS. 6A-6E show a comparison of the fluorescence intensity and bleed-through from the DAPI channel of Compounds 7 and 7B. FIGS. 6A-6D show that Compound 7B is brighter than Compound 7 when imaged in the Cy5 channel (FIGS. 6A and 6C, respectively), and shows less bleed-through into the DAPI channel (FIGS. 6B and 6D, respectively). FIG. 6E shows a bar plot demonstrating that the Compound 7B signal increased 12% in the Cy5 channel when compared to Compound 7 (see FIG. 6E, #3 and #1, respectively), and a surprising 50% decrease in the DAPI channel when compared with Compound 7 (FIG. 6E, #4 and #2, respectively).

FIG. 7A compares the percentage of fluorescence remaining in specimens stained with AF647 or Compound 10B and mounted with PROLONG™ Diamond (PLD) or VECTASHIELD™. AF647 plus VECTASHIELD was completely photobleached (data not shown). FIG. 7B shows a schematic diagram of how the specimens were imaged with a confocal microscope using the 633 nm laser. Each region of interest within 3 fields of view was scanned 50 times.

FIG. 10A illustrates preparation of a compound useful as a fixed cell stain, herein represented by an SiR dye conjugated to a ligand, according to certain embodiments provided herein. FIG. 10B illustrates preparation of a water-soluble SiR NHS ester followed by conjugation thereof to an antibody, according to certain embodiments provided herein.

FIG. 11A compares the Absorbance spectra of Compounds 8, 10A, and 12 with AF647. FIG. 11B compares the Emission spectra of Compounds 10A and 12 with AF647.

FIG. 12A shows cells stained with AF647. FIG. 12B shows staining of cells with Compound 10A (DOL=15). FIG. 12C compares the fluorescence of AF647, Compound 10A (DOL=10), and Compound 10A (DOL=15) versus the concentration of each labeled secondary reagent used. In the Compound 10A results, although less bright than AF647, no off-target or background fluorescence was noted, and Compound 10A showed better photostability than AF647.

DETAILED DESCRIPTION OF CERTAIN EMBODIMENTS

Figure 1A:
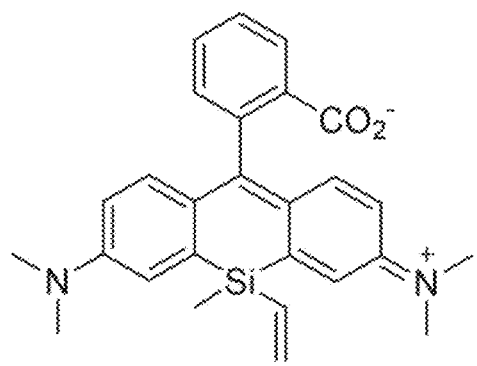
FIGS. 1A-1R show structures of exemplary Si-Rhodamine (SiR) compounds provided herein.
Figure 1A:
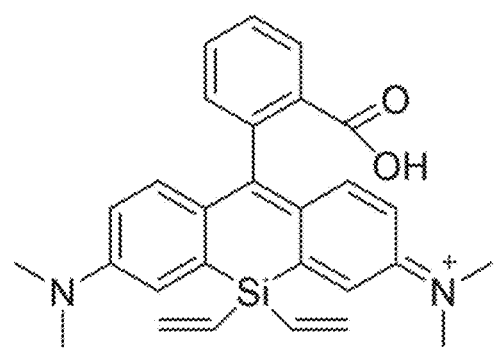
Figure 1A:
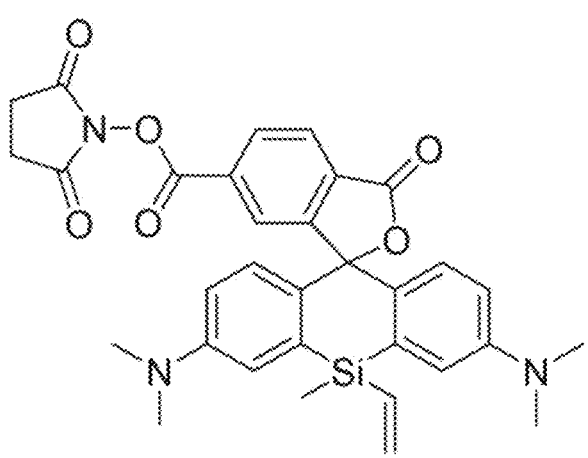
Figure 1A:
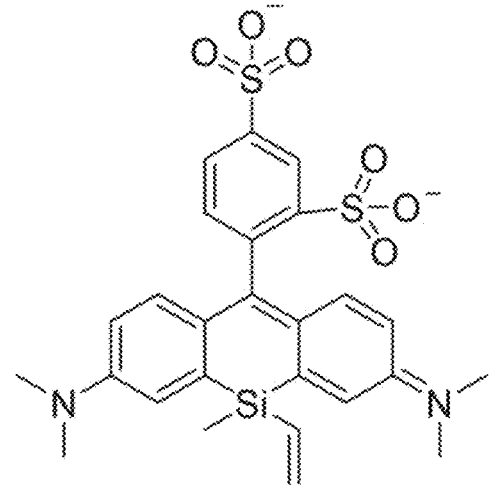
Figure 1A:
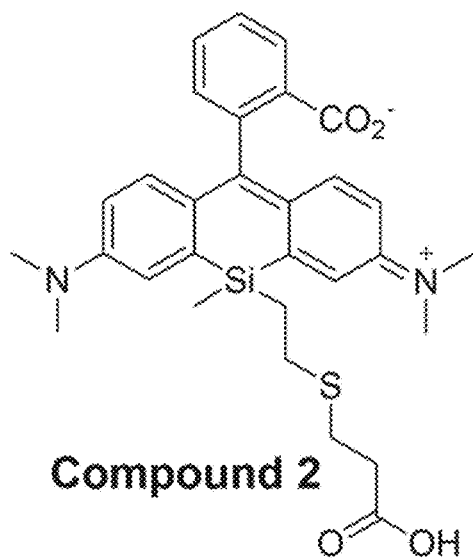
Figure 1A:
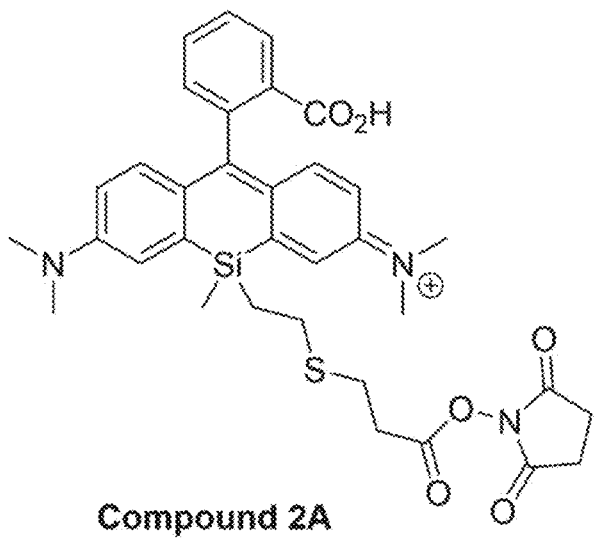
Figure 1B:
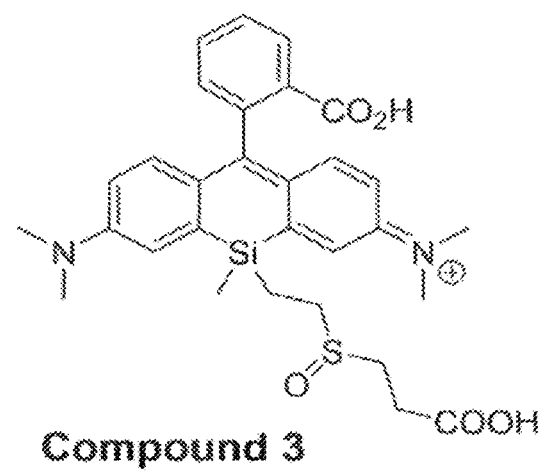
FIG. 1B shows the structures of Compounds 3, 4 and 4A.
Figure 1B:
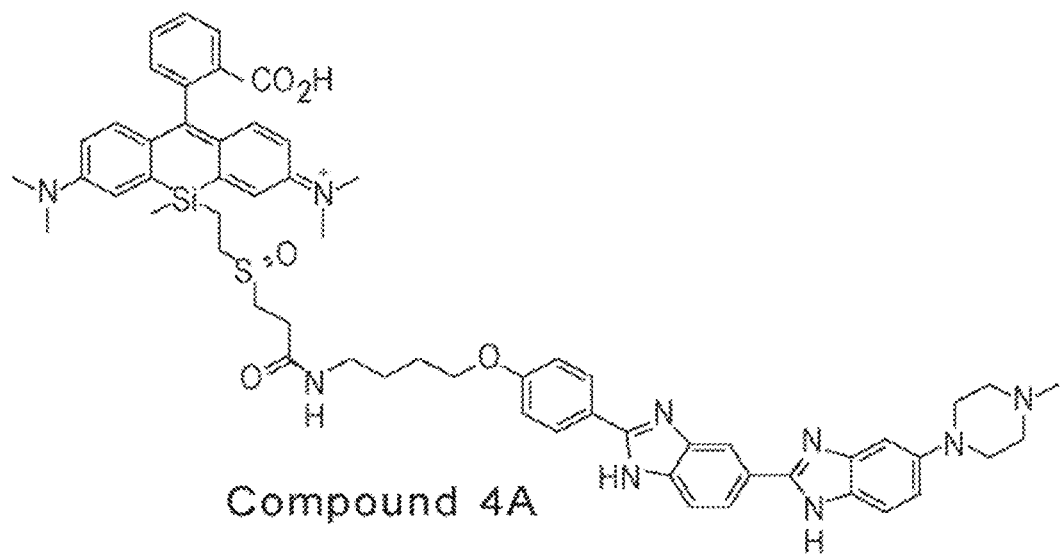
Figure 1B:
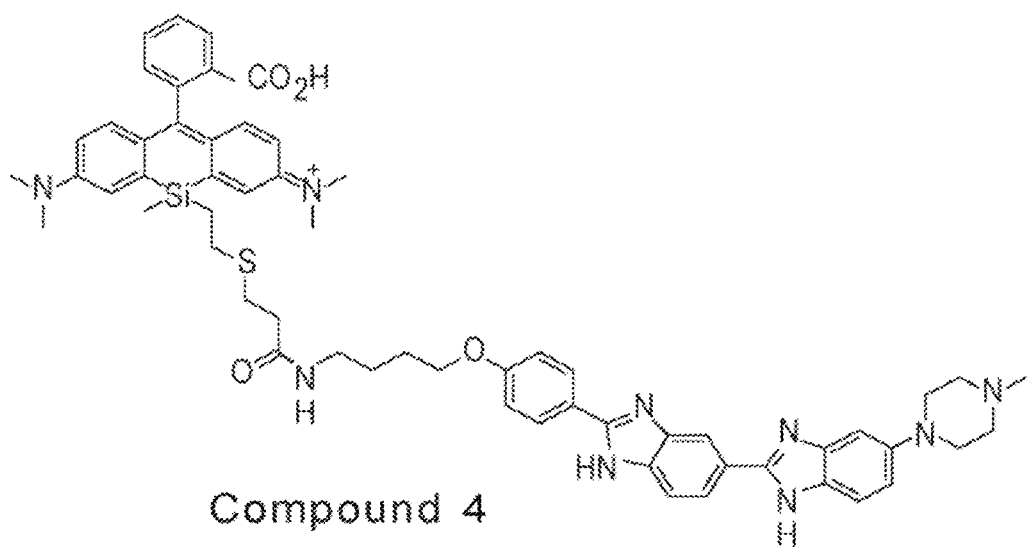
Figure 1C:
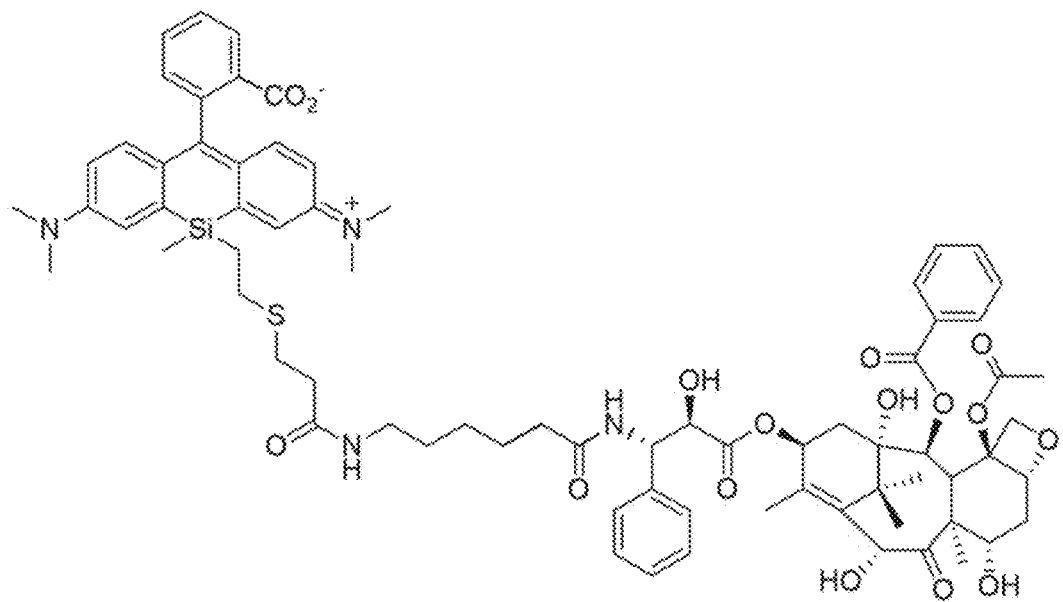
FIG. 1C shows the structures of Compounds 5 and 6.
Figure 1C:
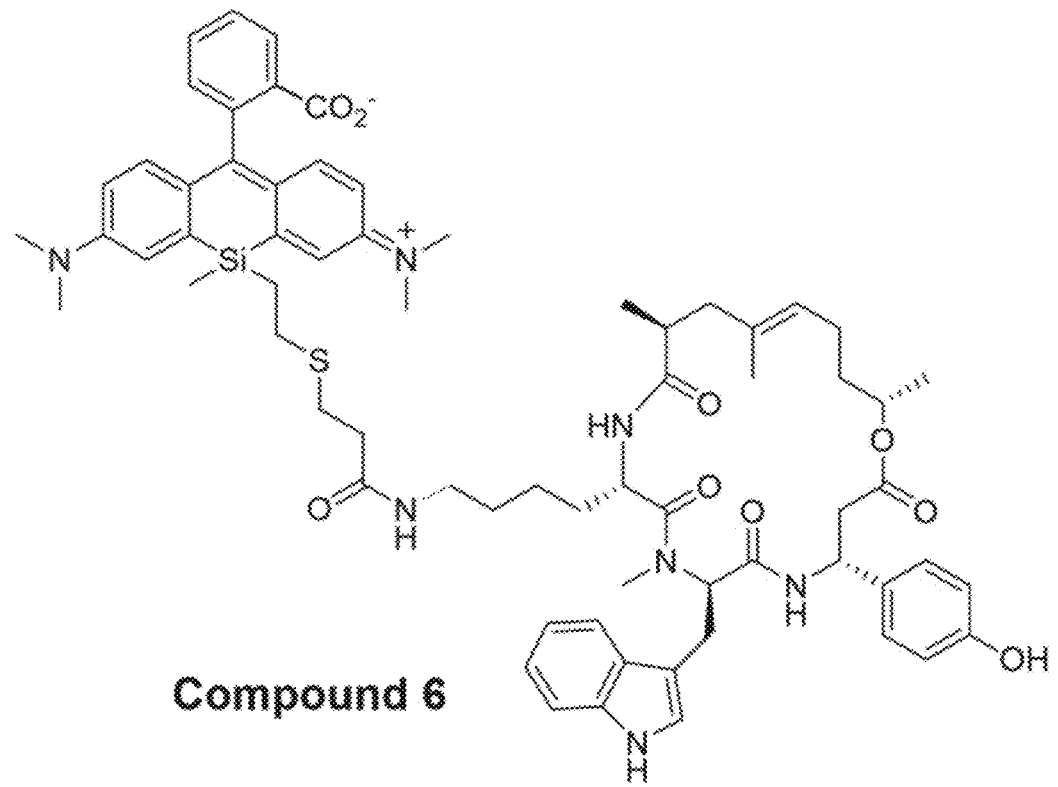
Figure 1D:
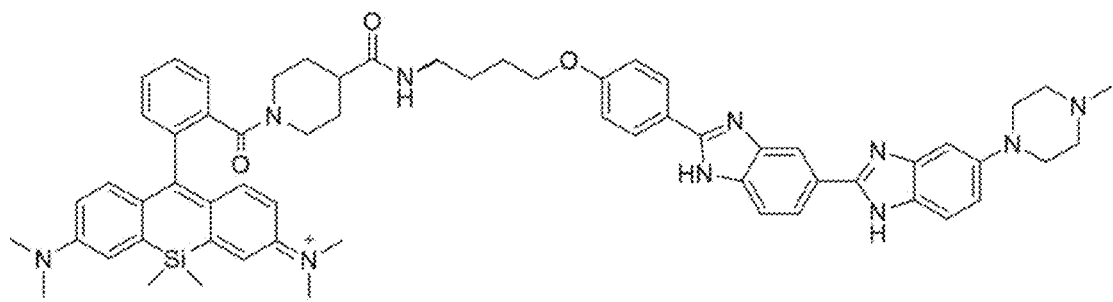
FIG. 1D shows the structures of Compounds 7, 7A, and 7B.
Figure 1D:
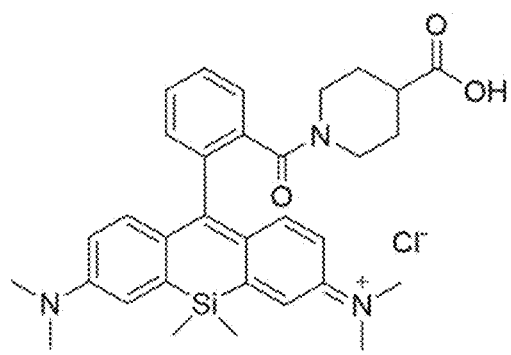
Figure 1D:
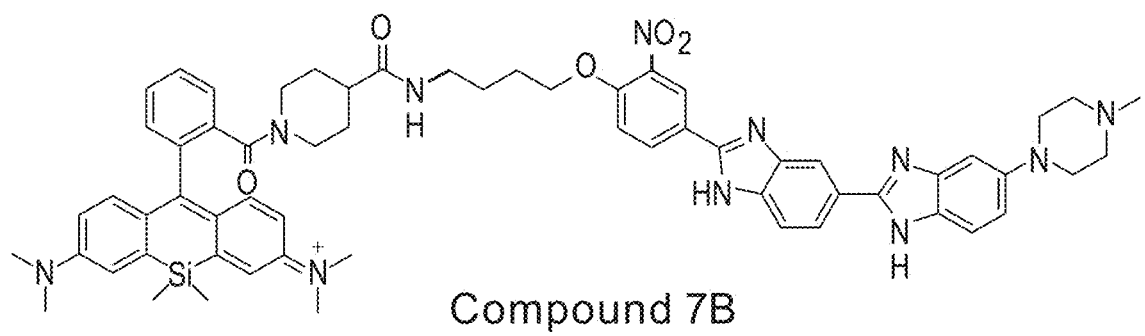
Figure 1E:
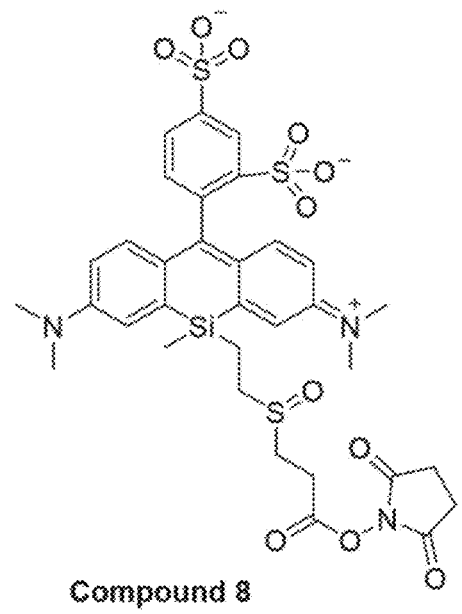
FIG. 1E shows the structures of Compounds 8, 9, and 10A.
Figure 1E:
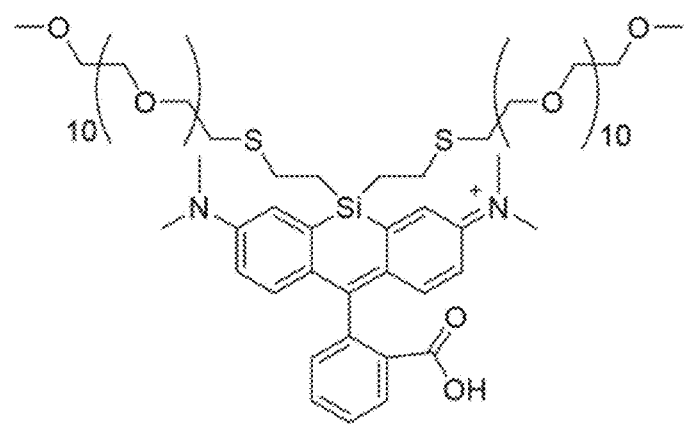
Figure 1E:
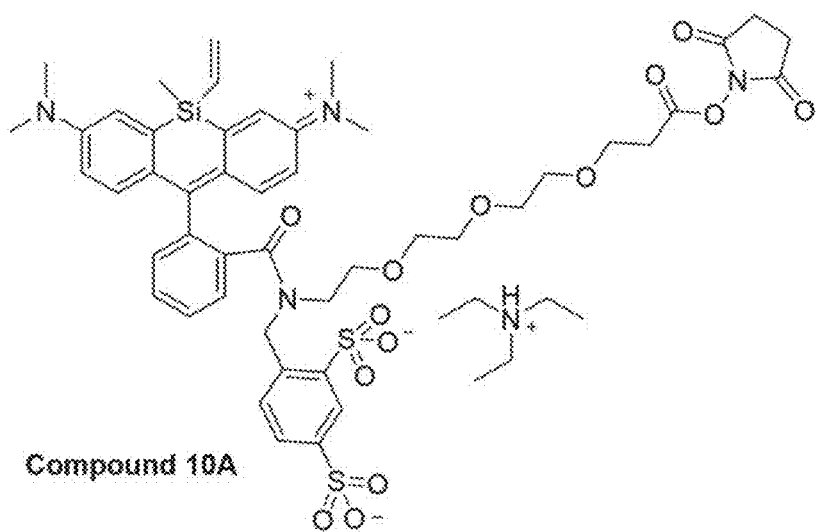
Figure 1F:
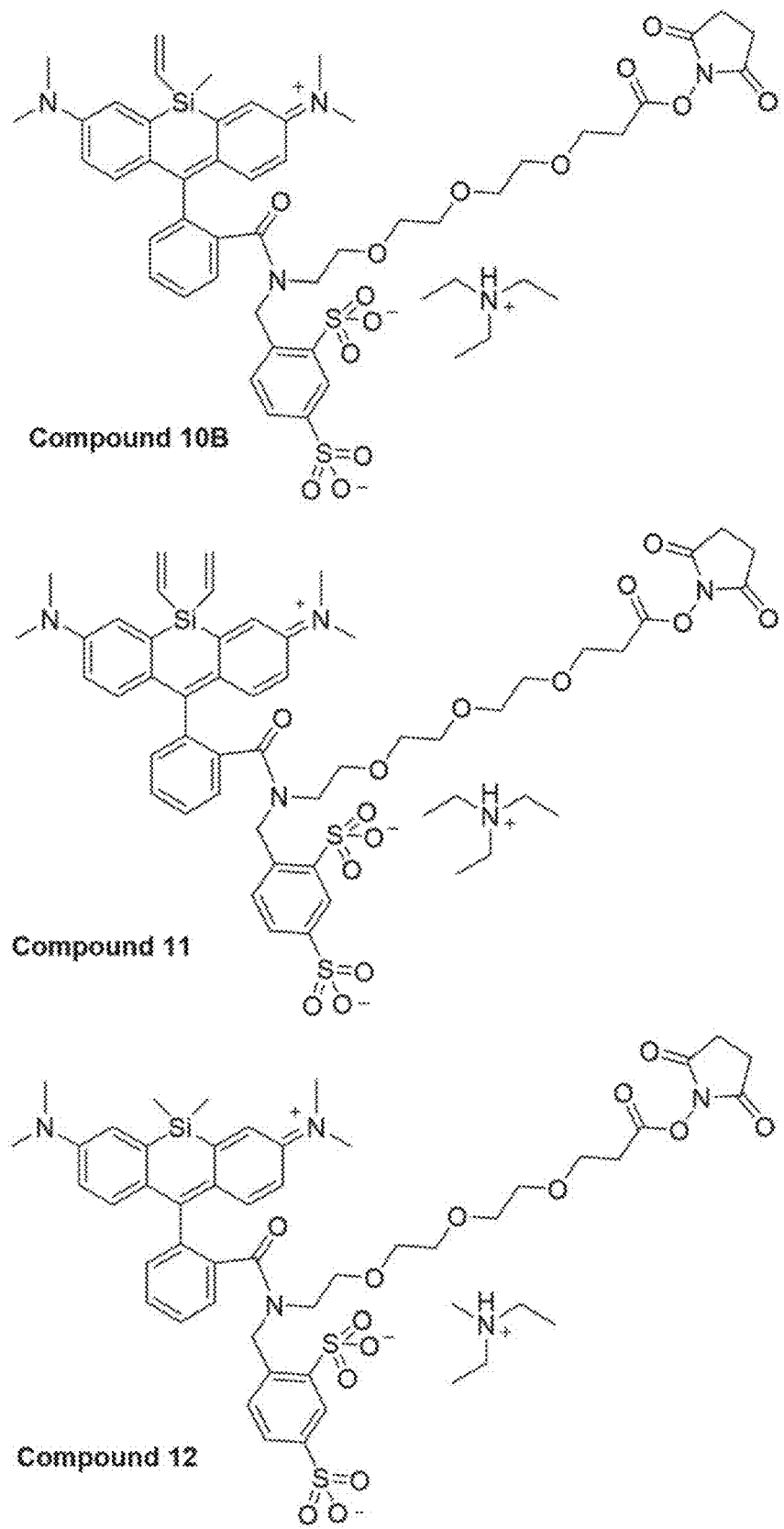
FIG. 1F shows the structures of Compounds 10B, 11, and 12.

Reference will now be made in detail to certain embodiments of the disclosure, examples of which are illustrated in the accompanying drawings. It is to be understood that both the general description and detailed description are exemplary and explanatory only and are not restrictive of the teachings. While the disclosure will be described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a dye" includes a plurality of dyes and reference to "a cell" includes a plurality of cells and the like. The term "or" is used in an inclusive sense, i.e., equivalent to "and/or," unless the context clearly dictates otherwise.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. "About" indicates a degree of variation that does not substantially affect the properties of the described subject matter, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques. Also, the use of "comprise", "comprises", "comprising", "contain", "contains", "containing", "include", "includes", and "including" are not intended to be limiting.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Definitions

Unless stated otherwise, the following terms and phrases as used herein are intended to have the following meanings:

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "kit" refers to a packaged set of related components, such as one or more compounds or compositions and one or more related materials such as solvents, solutions, buffers, instructions, or desiccants.

"Substituted" as used herein refers to a molecule wherein one or more hydrogen atoms are replaced with one or more non-hydrogen atoms, functional groups or moieties. By example, an unsubstituted nitrogen is —$NH_2$, while a substituted nitrogen is —$NHCH_3$. Exemplary substituents include but are not limited to halogen, e.g., fluorine and chlorine, ($C_1$-$C_8$) alkyl, sulfate, sulfonate, sulfone, amino, ammonium, amido, nitrile, nitro, lower alkoxy, phenoxy, aromatic, phenyl, polycyclic aromatic, heterocycle, water-solubilizing group, linkage, and linking moiety. In some embodiments, substituents include, but are not limited to, —X, —R, —OH, —OR, —SR, —SH, —$NH_2$, —NHR, —$NR_2$, —$^+NR_3$, —N=$NR_2$, —$CX_3$, —CN, —OCN, —SCN, —NCO, —NCS, —NO, —$NO_2$, —$N_2^+$, —$N_3$, —NHC(O)R, —C(O)R, —C(O)$NR_2$, —S(O)$_2$O—, —S(O)$_2$R, —OS(O)$_2$OR, —S(O)$_2$NR, —S(O)R, —OP(O)(OR)$_2$, —P(O)(OR)$_2$, —P(O)(O)$_2$, —P(O)(OH)$_2$, —C(O)R, —C(O)X, —C(S)R, —C(O)OR, —$CO_2$, —C(S)OR, —C(O)SR, —C(S)SR, —C(O)$NR_2$, —C(S)$NR_2$, —C(NR)$NR_2$, where each X is independently a halogen and each R is independently —H, $C_1$-$C_6$ alkyl, $C_5$-$C_{14}$ aryl, heterocycle, or linking group.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined herein, polymers arrived at by defining substituents with further substituents to themselves (e.g., substituted aryl having a substituted aryl group as a substituent which is itself substituted with a substituted aryl group, which is further substituted by a substituted aryl group etc) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the definitions provided herein are not intended to include impermissible substitution patterns (e.g., methyl substituted with 5 fluoro groups). Such impermissible substitution patterns are well known to the skilled artisan.

The compounds disclosed herein may exist in unsolvated forms as well as solvated forms, including hydrated forms. These compounds may exist in multiple crystalline or amorphous forms. In general, all physical forms are equivalent for the uses described herein and are intended to be within the scope of the present disclosure. The compounds disclosed herein may possess asymmetric carbon atoms (i.e., chiral centers) or double bonds; the racemates, diastereomers, geometric isomers and individual isomers of the compounds described herein are within the scope of the present disclosure. The compounds described herein may be prepared as a single isomer or as a mixture of isomers.

Where substituent groups are specified by their conventional chemical formulae and are written from left to right, they equally encompass the chemically identical substituents, which would result from writing the structure from right to left, e.g., —CH$_2$O— is intended to also recite —OCH$_2$—.

It will be understood that the chemical structures that are used to define the compounds disclosed herein are each representations of one of the possible resonance structures by which each given structure can be represented. Further, it will be understood that by definition, resonance structures are merely a graphical representation used by those of skill in the art to represent electron delocalization, and that the present disclosure is not limited in any way by showing one particular resonance structure for any given structure.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

"Alkyl" means a saturated or unsaturated, branched, straight-chain, or cyclic hydrocarbon radical derived by the removal of one hydrogen atom from a single carbon atom of a parent alkane, alkene, or alkyne. Typical alkyl groups consist of 1 to 12 saturated and/or unsaturated carbons, including, but not limited to, methyl, ethyl, propyl, butyl, and the like. In some embodiments, an alkyl is a monovalent saturated aliphatic hydrocarbyl group having from 1 to 10 carbon atoms, e.g., 1 to 6 carbon atoms, e.g. 1, 2, 3, 4, 5 or 6 carbon atoms. "Alkyl" includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

"Substituted alkyl" refers to an alkyl group having from 1 to 5, e.g., 1 to 3, or 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxylalkyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, —SO$_3$H, substituted sulfonyl, sulfonyloxy, thioacyl, thiol, alkylthio, and substituted alkylthio, wherein said substituents are defined herein. Particular substituted alkyl groups comprise a reactive group for direct or indirect linking to a carrier molecule or solid support, for example, but not limited to, alkyl substituted by carboxyl or a carboxyl ester (e.g. an activated ester such as an N-hydroxysuccinimide ester) and alkyl substituted by aminocarbonyl —CONHR where R is an organic moiety as defined below with reference to the term "aminocarbonyl", e.g. a C$_1$-C$_{10}$ (e.g. C$_1$-C$_6$) alkyl terminally substituted by a reactive group (R$_x$) including, but not limited to, carboxyl, carboxylester, maleimide, succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

"Alkylsulfonate" is —(CH$_2$)$_n$—SO$_3$H, wherein n is an integer from 1 to 6.

"Alkoxy" refers to the group-O-alkyl wherein alkyl is defined herein. Alkoxy includes, by way of example, methoxy, ethoxy, n-propoxy, isopropoxy, n-butoxy, t-butoxy, sec-butoxy, and n-pentoxy. In some embodiments, an alkoxy is —OR where R is C$_1$-C$_6$ alkyl.

"Substituted alkoxy" refers to the group —O-(substituted alkyl), wherein substituted alkyl is defined herein.

"Alkyldiyl" means a saturated or unsaturated, branched, straight chain or cyclic hydrocarbon radical of 1 to 20 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl, 1,3-propyldiyl, 1,4-butyldiyl, and the like.

"Aryl" or "Ar" means a monovalent aromatic hydrocarbon radical of 6 to 20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. In some embodiments, an aryl is a monovalent aromatic carboxylic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryl groups include phenyl and naphthyl.

"Substituted aryl" refers to aryl groups which are substituted with 1 to 5, e.g., 1 to 3, or 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, —SO$_3$H, substituted sulfonyl, sulfonyloxy, thioacyl, thiol, alkylthio, and substituted alkylthio, wherein said substituents are defined herein.

"Aryleno" means an aromatic ring fused at two contiguous aryl carbons of a compound, i.e. a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system results in a fused aromatic ring system, e.g. naphthalene. Typical aryleno groups include, but are not limited to: [1,2]benzeno, [1,2]naphthaleno and [2,3]naphthaleno.

"Aryldiyl" means an unsaturated cyclic or polycyclic hydrocarbon radical of 6-20 carbon atoms having a conjugated resonance electron system and at least two monovalent radical centers derived by the removal of two hydrogen atoms from two different carbon atoms of a parent aryl compound.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, e.g., 1 to 3, or 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Alkenyl" refers to alkenyl groups having from 2 to 6 carbon atoms, e.g., 2 to 4 carbon atoms, and having at least 1, e.g., from 1 to 2 sites of alkenyl unsaturation. Such groups are exemplified, for example, by vinyl, allyl, but-3-en-1-yl, and propenyl.

"Substituted alkenyl" refers to alkenyl groups having from 1 to 3 substituents, e.g., 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, —SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group CH$_3$C(O)—.

"Acylamino" refers to the groups —NRC(O)alkyl, —NRC(O) substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O) substituted heterocyclic, wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)C)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NRSO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryloxy" refers to the group —O-aryl, where aryl is as defined herein, that includes, by way of example, phenoxy and naphthoxy.

"Substituted aryloxy" refers to the group —O-(substituted aryl), where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkynyl" refers to alkynyl groups having from 2 to 6 carbon atoms and e.g., 2 to 3 carbon atoms and having at least 1, e.g., from 1 to 2 sites of alkynyl unsaturation.

"Substituted alkynyl" refers to alkynyl groups having from 1 to 3 substituents, e.g., 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, —SO$_3$H, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof.

"Carboxyl alkyl" or "carboxyalkyl" refers to the group —(CH$_2$)$_n$COOH, where n is 1-6.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, —NR—C(O)O— substituted alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic, wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O— substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O— cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation, e.g., from 1 to 2 sites of >C=C< ring unsaturation.

"Substituted cycloalkyl" and "substituted cycloalkenyl" refer to a cycloalkyl or cycloalkenyl group having from 1 to 5, e.g., 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, —SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NRC(=NR)N(R)$_2$ where each R is independently selected from the group consisting of hydrogen, alkyl, substituted alkyl, aryl, substituted aryl, heteroaryl, substituted heteroaryl, heterocyclic, and substituted heterocyclic and two R groups attached to a common guanidino nitrogen atom are optionally joined together with the nitrogen bound thereto to form a heterocyclic or substituted heterocyclic group, provided that at least one R is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, e.g., 1 to 3 or 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" means any ring system having at least one non-carbon atom in a ring, e.g. nitrogen, oxygen, and sulfur. In some embodiments, a heterocycle is a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties. Heterocycles include, but are not limited to: pyrrole, indole, furan, benzofuran, thiophene, benzothiophene, 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, phthalazine, quinazoline, quinoxaline, 3-(1,2,4-N)-triazolyl, 5-(1,2,4-N)-triazolyl, 5-tetrazolyl, 4-(1-O,3-N)-oxazole, 5-(1-O,3-N)-oxazole, 4-(1-S,3-N)-thiazole, 5-(1-S,3-N)-thiazole, 2-benzoxazole, 2-benzothiazole, 4-(1,2,3-N)-benzotriazole, and benzimidazole.

"Substituted heterocyclic" or "substituted heterocycloalkyl" or "substituted heterocyclyl" refers to heterocyclyl groups that are substituted with from 1 to 5, e.g., 1 to 3 of the same substituents as defined for substituted cycloalkyl.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Heterocyclyloxy" refers to the group —O-heterocyclyl.

"Substituted heterocyclyloxy" refers to the group —O-(substituted heterocyclyl).

"Heterocyclylthio" refers to the group —S— heterocyclyl.

"Substituted heterocyclylthio" refers to the group —S-(substituted heterocyclyl).

"Hydrazinyl" refers to the group —NHNH$_2$— or =NNH—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$(alkyl)-NH$_2$.

"Nitro" refers to the group —NO$_2$.

"Oxo" refers to the atom (=O) or (—O$^-$).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

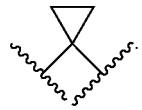

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$— and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl), wherein substituted alkyl is as defined herein.

The term "detectable response" as used herein refers to an occurrence of or a change in, a signal that is directly or indirectly detectable either by observation or by instrumentation. In some embodiments, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

As used herein, the term "fluorogenic" refers to a compound or a composition that demonstrates a change in fluorescence upon binding to a biological compound or analyte of interest and/or upon cleavage by an enzyme.

As used herein, the term "fluorophore" refers to a moiety or compound capable of emitting light upon excitation, and includes fluorogenic fluorophores that exhibit fluorescence upon binding to a biological compound or analyte of interest and/or upon cleavage by an enzyme. Fluorophores of the present disclosure may be substituted to alter the solubility, spectral properties or physical properties of the fluorophore.

As used herein, "a pharmaceutically acceptable salt" or "a biologically compatible salt" is a counterion that is not toxic as used, and does not have a substantially deleterious effect on biomolecules. Examples of such salts include, among others, K$^+$, Na$^+$, Cs$^+$, Li$^+$, Ca$^{2+}$, Mg$^{2+}$, Cl$^-$, AcO$^-$, and alkylammonium or alkoxyammonium salts.

The term "linker" or "L", as used herein, refers to a single covalent bond or a moiety comprising series of stable covalent bonds, the moiety often incorporating 1-40 plural valent atoms selected from the group consisting of C, N, O, S and P that covalently attach the fluorogenic or fluorescent compounds to another moiety such as a chemically reactive group or a biological and non-biological component. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups, or both. Examples of such pendant moieties are hydrophilicity modifiers, for example solubilizing groups like, e.g. sulfo (—SO$_3$H or —SO$_3^-$). In certain embodiments, L is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety that includes —C(O)NH—, —C(O)O—, —NH—, —S—, —O—, and the like. Linkers may, by way of example, consist of a combination of moieties selected from alkyl; —C(O)NH—; —C(O)O—; —NH—; —S—; —O—; —C(O)—; —S(O)$_n$— where n is 0, 1 or 2; —O—; 5- or 6-membered monocyclic rings; and optional pendant functional groups, for example sulfo, hydroxy and carboxy. The moiety formed by a linker bonded to a reactive group or reactive linker (R$_x$) may be designated -L-R$_x$. The reactive group may be reacted with a substance reactive therewith, whereby the linker becomes bonded to a conjugated substance (S$_c$) and may be designated -L-S$_c$, or in some cases, the linker may contain a residue of a reactive group (e.g. the carbonyl group of an ester) and may be designated "-L$_R$". A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

The term "reactive group" also referred to herein as "reactive ligand" (or "R$_x$"), as used herein, refers to a group that is capable of reacting with another chemical group to form a covalent bond, i.e., is covalently reactive under suitable reaction conditions, and generally represents a point of attachment for another substance. The reactive group is a moiety, such as carboxylic acid or succinimidyl ester, on the compounds of the present disclosure that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters (or succinimidyl esters (SE)), maleimides, sulfodichlorophenyl (SDP) esters, sulfotetrafluorophenyl (STP) esters, tetrafluorophenyl (TFP) esters, pentafluorophenyl (PFP) esters, nitrilotriacetic acids (NTA), aminodextrans, cyclooctyne-amines and the like.

Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989). Exemplary reactive groups or reactive ligands include NHS esters, phosphoramidites, and other moieties listed in Table 1 below. Nucleotides, nucleosides, and saccharides (e.g., ribosyls and deoxyribosyls) are also considered reactive ligands due to at least their ability to form phosphodiester bonds through enzymatic catalysis. For the avoidance of doubt, saturated alkyl groups are not considered reactive ligands.

The term "carrier molecule" as used herein, refers to a biological or a non-biological component that is or becomes covalently bonded to a cell-tracker compound disclosed herein. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. Included is one embodiment in which carrier molecules comprise an organic moiety having at least 4 plural valent atoms and often more than 10 plural valent atoms (i.e., atoms other than hydrogen and halo), e.g. at least 15 such atoms, as in the case of moieties having at least 20 such atoms.

The term "conjugated substance" or "$S_c$" refers to a carrier molecule or solid support.

As used herein, a "target-binding moiety" refers to a moiety that is or can be attached to a fluorophore to provide a compound with both specific binding activity and fluorescent or fluorogenic properties. Exemplary target-binding moieties include cytoskeleton-binding moieties such as taxol or actin-binding peptides; DNA-binding moieties such as Hoechst or nitro-Hoechst; polynucleotides (which can hybridize to a complementary sequence); and antibodies and antigen-binding fragments thereof.

The term "solid support," as used herein, refers to a matrix or medium that is substantially insoluble in liquid phases and capable of binding a molecule or particle of interest. Solid supports suitable for use herein include semi-solid supports and are not limited to a specific type of support. Useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as SEPHAROSE® (GE Healthcare), poly(acrylate), polystyrene, poly(acrylamide), polyol, agarose, agar, cellulose, dextran, starch, FICOLL® (GE Healthcare), heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

As used herein, the term "staining" is a technique used in microscopy to enhance contrast in the microscopic image. Stains and dyes are frequently used to highlight structures in biological tissues and cells. Staining also involves adding a dye to a substrate to quantify or qualify the presence of a specific compound, such as a protein, nucleic acid, lipid or carbohydrate. Biological staining is also used to mark cells in flow cytometry and to flag proteins or nucleic acids in gel electrophoresis. Staining is not limited to biological materials and can be used to study the morphology of other materials such as semi-crystalline polymers and block copolymers.

"Lower alkyl" denotes straight-chain and branched hydrocarbon moieties containing from 1 to 8 carbon atoms, e.g., methyl, ethyl, propyl, isopropyl, tert-butyl, isobutyl, sec-butyl, neopentyl, tert-pentyl, and the like. "Lower haloalkyl" denotes a lower substituted alkyl with one or more halogen atom substituents, usually fluorine, chloro, bromo, or iodo.

"Lower alkene" denotes a hydrocarbon containing from 1 to 8 carbon atoms wherein one or more of the carbon-carbon bonds are double bonds.

"Lower alkyne" denotes a hydrocarbon containing from 1 to 8 carbon atoms wherein one or more of the carbons are bonded with a triple bond.

"Nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position. When the nucleoside base is purine or 7-deazapurine, the sugar moiety is attached at the $N^9$-position of the purine or deazapurine, and when the nucleoside base is pyrimidine, the sugar moiety is attached at the $N^1$-position of the pyrimidine, e.g., Kornberg and Baker, DNA Replication, 2nd Ed. (Freeman, San Francisco, 1992).

The term "nucleotide" as used herein refers to a phosphate ester of a nucleoside, e.g., triphosphate esters, wherein the most common site of esterification is the hydroxyl group attached to the C-5 position of the pentose. The term "nucleoside/tide" as used herein refers to a set of compounds including both nucleosides and nucleotides and analogs thereof. "Analogs" in reference to nucleosides/tides include synthetic analogs having modified base moieties, modified sugar moieties and/or modified phosphate moieties, e.g. described generally by Scheit, Nucleotide Analogs (John Wiley, New York, 1980). Phosphate analogs comprise analogs of phosphate wherein the phosphorous atom is in the +5 oxidation state and one or more of the oxygen atoms is replaced with a non-oxygen moiety, exemplary analogs including phosphorothioate, phosphorodithioate, phosphoroselenoate, phosphorodiselenoate, phosphoroanilothioate, phosphoranilidate, phosphoramidate, boronophosphates, and the like, including associated counterions, e.g., $H^+$, $NH_4^+$, $Na^+$, and the like if such counterions are present. Exemplary base analogs include but are not limited to 2,6-diaminopurine, hypoxanthine, pseudouridine, C-5-propyne, isocytosine, isoguanine, 2-thiopyrimidine, and other like analogs. Exemplary sugar analogs include but are not limited to 2'-modifications where the 2'-position is hydrogen, hydroxy, alkoxy, e.g., methoxy, ethoxy, allyloxy, isopropoxy, butoxy, isobutoxy and phenoxy, amino or alkylamino, fluoro, chloro and bromo. The term "labeled nucleoside/tide" refers to nucleosides/tides which are covalently attached to the dye compounds of Formula (I), optionally through a linker.

"Polynucleotide" (which includes "oligonucleotide") means linear polymers of natural nucleotide monomers or analogs thereof, including double and single stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or bonds including phosphate analogs thereof, including associated counterions, e.g., $H^+$, $NH_4^+$, $Na^+$, and the like if such counterions are present. Polynucleotides typically range in size from a few monomeric units, e.g. 8-40, to several thousands of monomeric units. Whenever a polynucleotide is represented by a sequence of letters, it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

"Water-solubilizing group" means a substituent which increases the solubility of the compounds of the invention in aqueous solution. Exemplary water-solubilizing groups include but are not limited to quaternary amine, sulfate, sulfonate, carboxylate, phosphonate, phosphate, polyether, polyhydroxyl, boronate, polyethylene glycol and repeating units of ethylene oxide (—$CH_2CH_2O$—).

Exemplary Compounds, Compositions, Methods, Uses, and Kits

Provided herein are silicon-rhodamine (SiR) dyes and conjugates thereof, kits and compositions including such dyes, as well as methods using such dyes for detecting and quantifying biological materials, methods of making and/or functionalizing or conjugating such dyes.

1. Dyes and Conjugates

Compounds of formula (I) are disclosed, as set forth in embodiment 1 above:

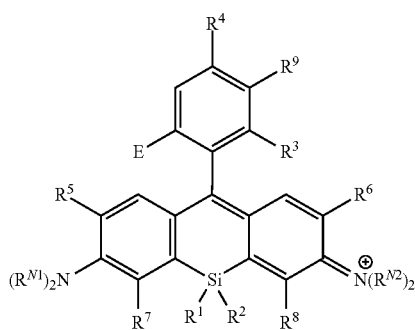

wherein:
$R^1$ is methyl, $C_{2-6}$ alkyl, vinyl, substituted vinyl, -$L^1$-$R^A$, or -$L^1$-$R^{B1}$;
$R^2$ is methyl, $C_{2-6}$ alkyl, vinyl, substituted vinyl, -$L^1$-$R^A$, or -$L^1$-$R^{B1}$;
or $R^1$ and $R^2$ form a ring together with the silicon to which they are attached; each $L^1$ is independently a linker;
each $R^A$ is independently a reactive ligand, a solubilizing functionality, a target-binding moiety or a nucleoside/tide moiety;
each $R^{B1}$ is independently a reactive ligand, a solubilizing functionality, a target-binding moiety or nucleoside/tide moiety;
$R^3$ is —COOH, $SO_3^-$, H, $R^{3a}$, -$L^1$-$R^A$, or -$L^1$-$R^{B1}$;
$R^{3a}$ is

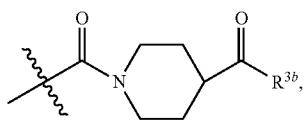

or

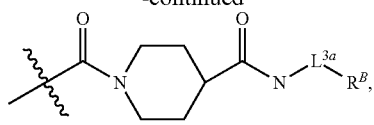

or —$C(O)N(R^{N3})(R^{N4})$;
$R^{N3}$ is H, methyl, $C_{2-6}$ alkyl, or —$CH_2$-A where A is an aryl or heteroaryl substituted with at least one polar or charged group;
$R^{N4}$ is -$L^1$-$R^A$, or -$L^1$-$R^{B1}$, or —$(CH_2CH_2O)_q$—$C(O)O$— $R^B$ where q is 2, 3, 4, 5, or 6;
$R^{3b}$ is —OH or —$N(R^{N5})$-$L^{3a}$-$R^B$;
each $L^{3a}$ is independently a linker;
$R^B$ is a reactive ligand or a target-binding moiety;
$R^{N5}$ is H, methyl, or $C_{2-6}$ alkyl;
$R^4$ is $SO_3^-$, methyl, chloro, $C_{2-6}$ alkyl, or H;
E is $SO_3^-$, methyl, chloro, $C_{2-6}$ alkyl, or H;
$R^5$ is H, methyl, or $C_{2-6}$ alkyl, or forms a ring with an $R^{N1}$;
$R^6$ is H, methyl, or $C_{2-6}$ alkyl, or forms a ring with an $R^{N2}$;
$R^7$ is H, methyl, or $C_{2-6}$ alkyl, or forms a ring with an $R^{N1}$;
$R^8$ is H, methyl, or $C_{2-6}$ alkyl, or forms a ring with an $R^{N2}$;
$R^9$ is $SO_3^-$, methyl, chloro, $C_{2-6}$ alkyl, or H;
each $R^{N1}$ is independently H, methyl, $C_{2-4}$ alkyl, —$C(O)R^{10}$, —$C(O)R^{13}$, or forms a ring with $R^5$ and/or $R^7$;
each $R^{N2}$ is independently H, methyl, $C_{2-4}$ alkyl, —$C(O)R^{10}$, —$C(O)R^{13}$, or forms a ring with $R^6$ and/or $R^8$;
$R^{10}$ is —$C(O)$—$CF_3$ or —O—$CH_2$-$A^1$ where $A^1$ is an aryl or heteroaryl optionally substituted with at least one $R^{11}$;
$R^{11}$ is methyl, $C_{2-6}$ alkyl, or —$OR^{12}$; and
$R^{12}$ is H, methyl, acetyl (Ac), acetoxymethyl (AM), —$PO_3^{2-}$, —$PO_3(AM)_2$, or a glycoside;
$R^{13}$ is

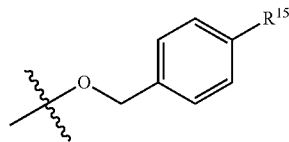

where $R^{15}$ is an oligopeptide or —OR' where R' is acetyl (Ac), AM, $PO_3^{2-}$, $PO_3(AM)_2$, or a glycoside and AM is acetoxymethyl;
further wherein (i) $R^2$ is not methyl or $C_{2-6}$ alkyl if $R^1$ is methyl or $C_{2-6}$ alkyl, OR (ii) $R^3$ is $R^{3a}$ or -$L^1$-$R^{B1}$;
or a spirolactone form and/or salt thereof.

Figure 1G:
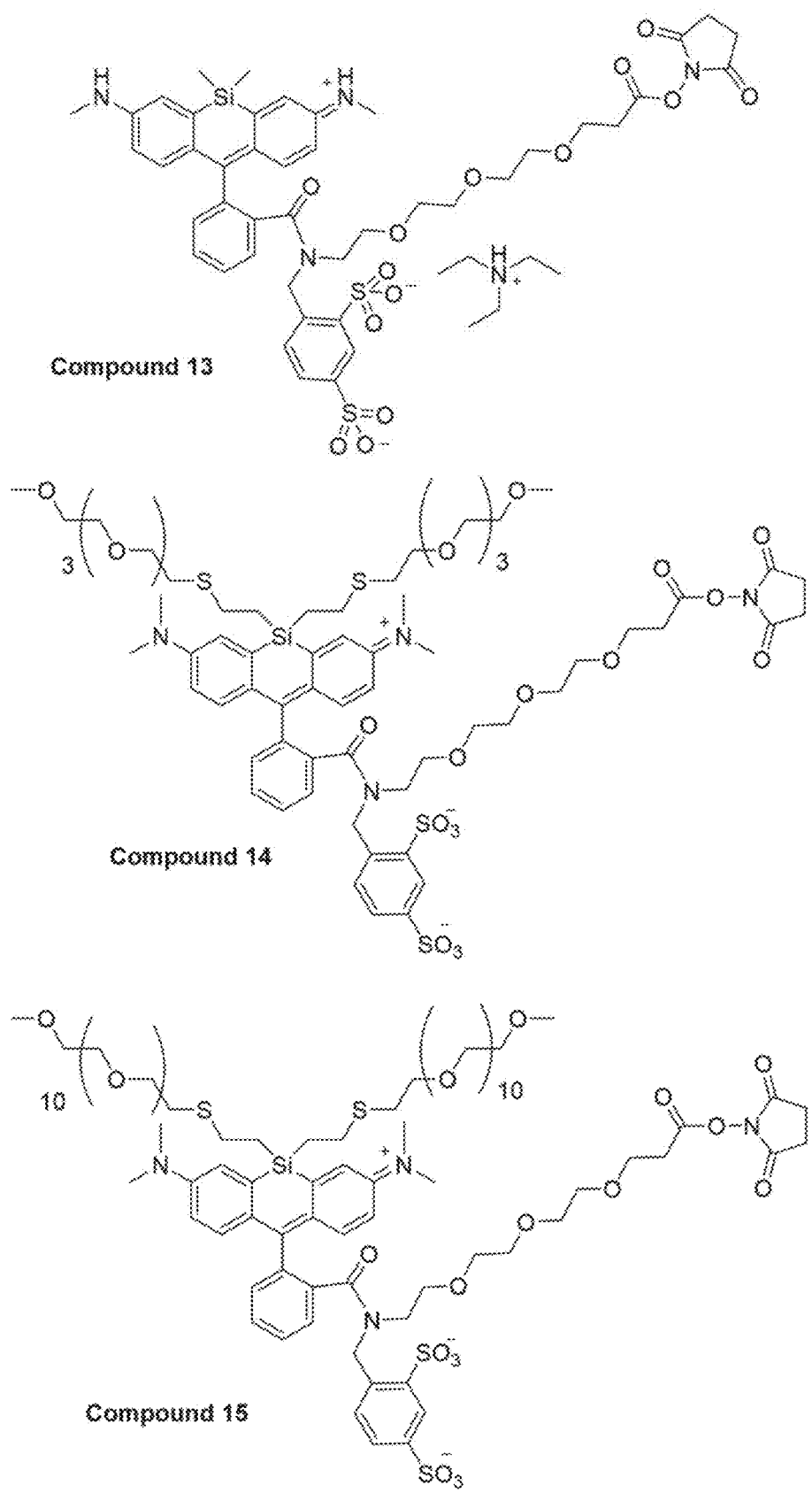
FIG. 1G shows the structures of Compounds 13, 14 and 15.
Figure 1H:
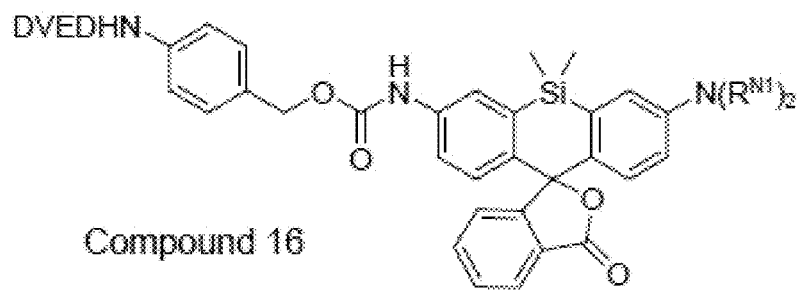
FIG. 1H shows the structures of Compounds 16, 17, 18, 19, 20 and 21.
Figure 1H:
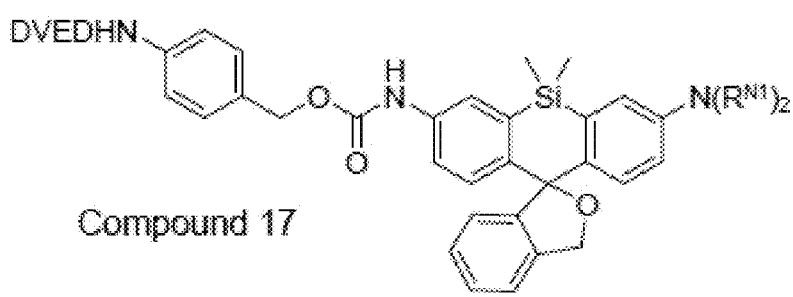
Figure 1H:
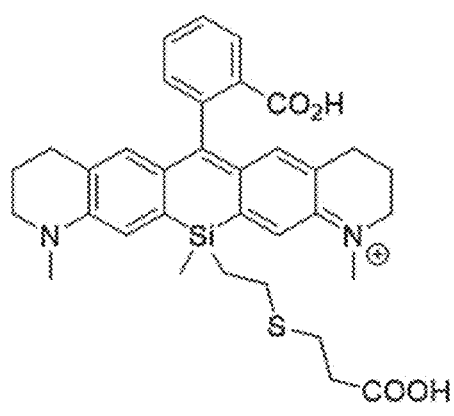
Figure 1H:
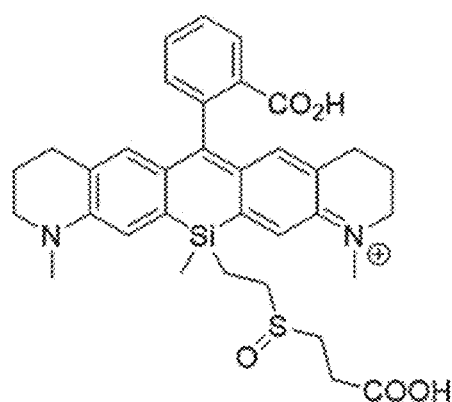
Figure 1H:
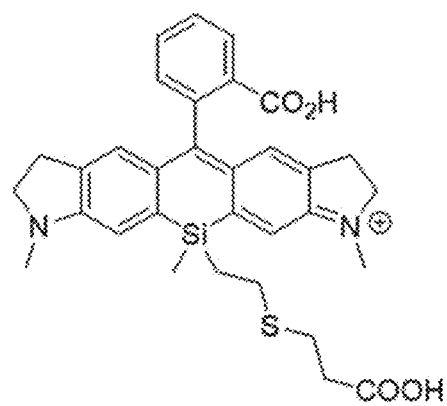
Figure 1H:
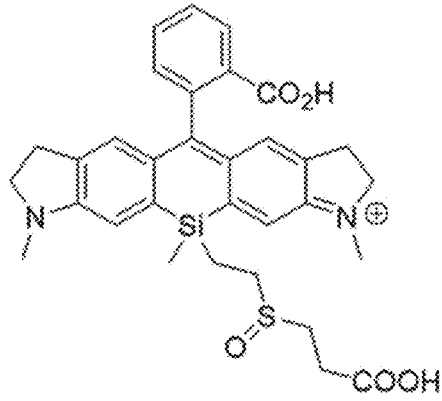
Figure 1I:
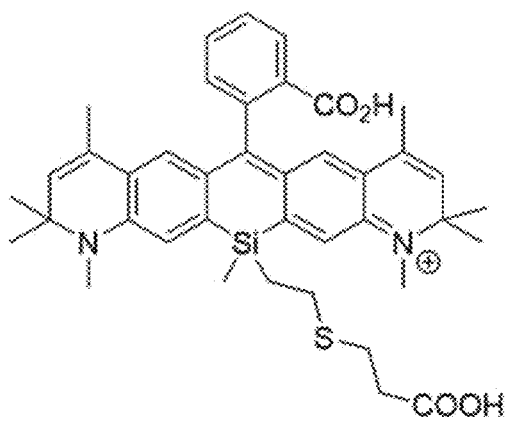
FIG. 1I shows the structures of Compounds 22, 23, 24, 25, 26 and 27.
Figure 1I:
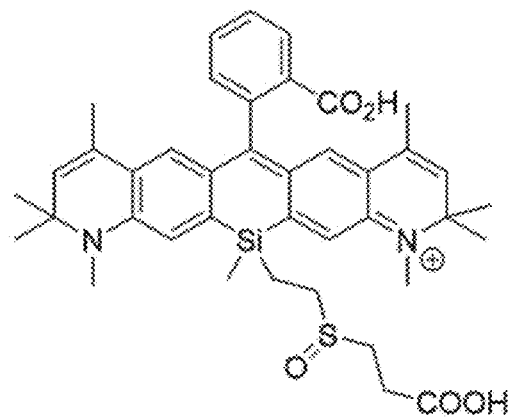
Figure 1I:
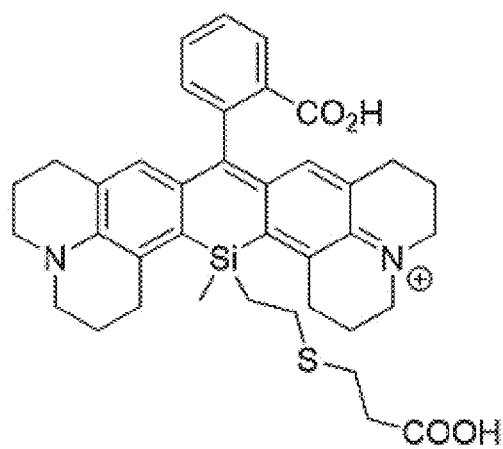
Figure 1I:
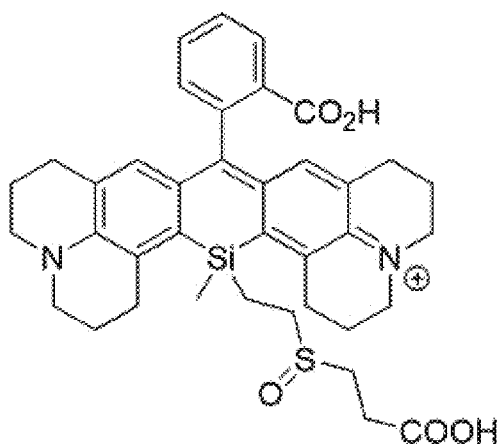
Figure 1I:
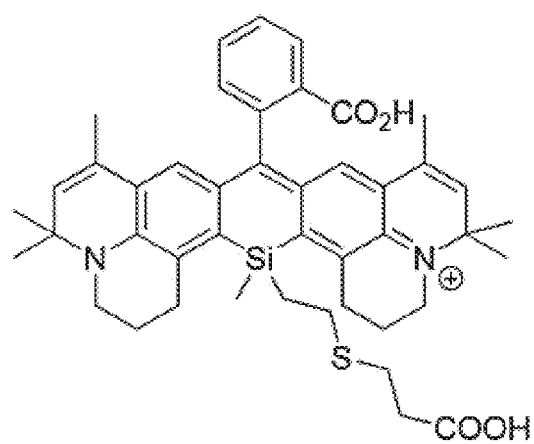
Figure 1I:
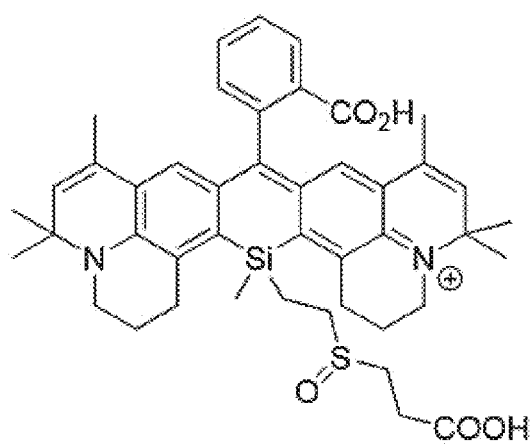
Figure 1J:
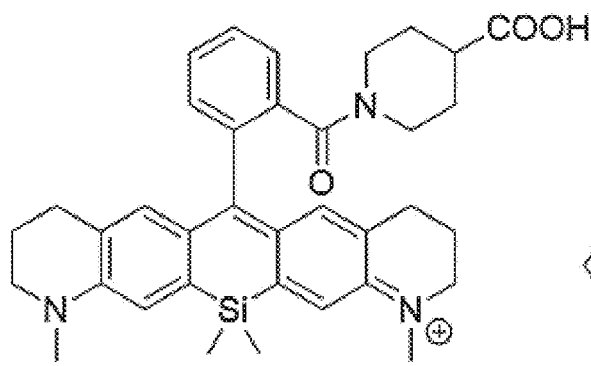
FIG. 1J shows the structures of Compounds 28, 29, 30, 31, 32 and 33.
Figure 1J:
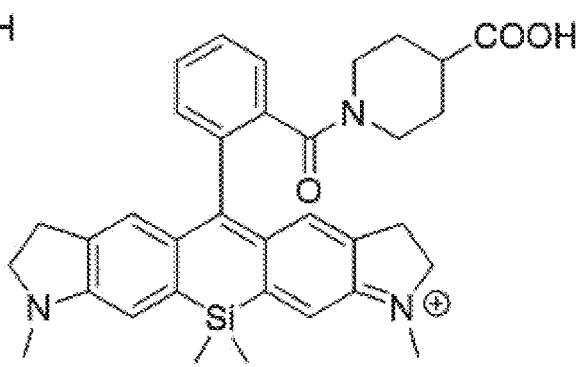
Figure 1J:
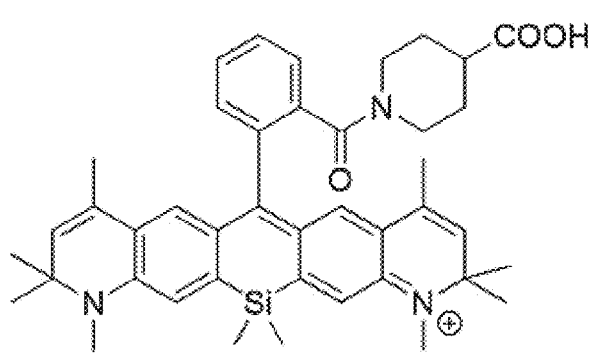
Figure 1J:
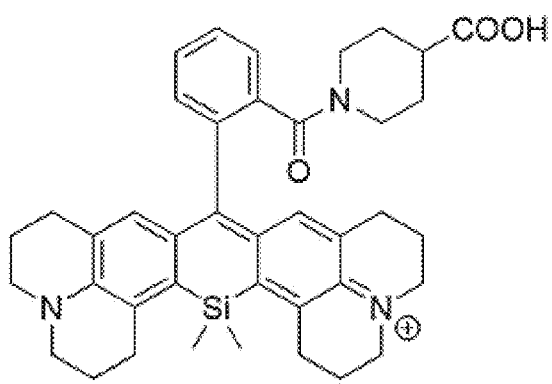
Figure 1J:
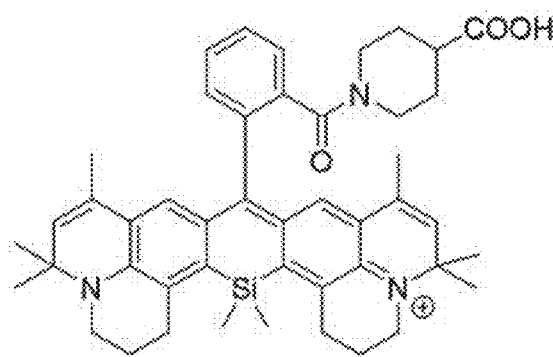
Figure 1J:
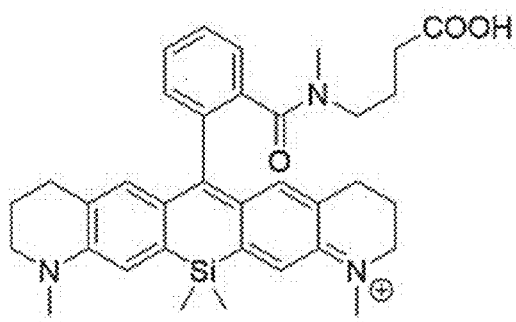
Figure 1K:
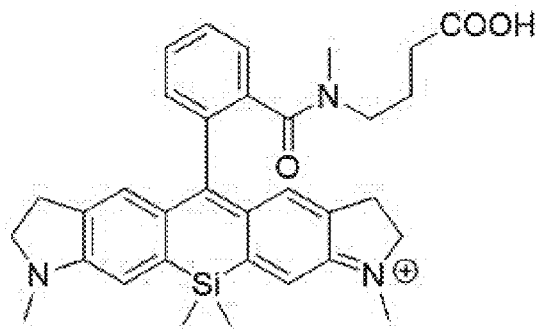
FIG. 1K shows the structures of Compounds 34, 35, 36, 37, 38 and 39.
Figure 1K:
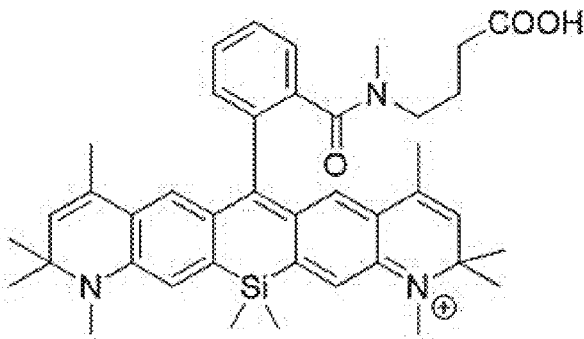
Figure 1K:
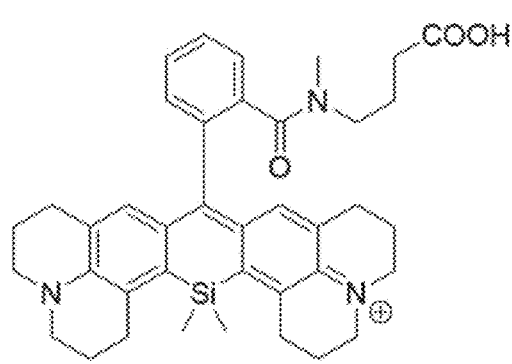
Figure 1K:
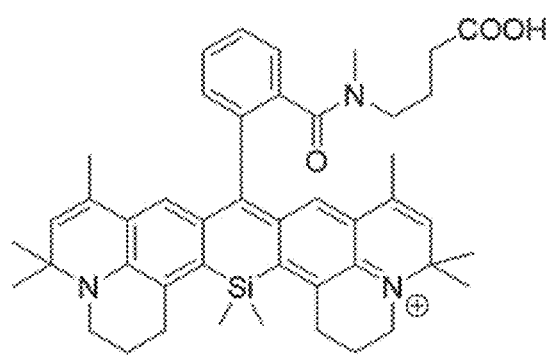
Figure 1K:
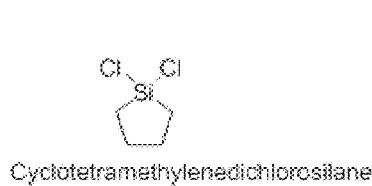
Figure 1K:
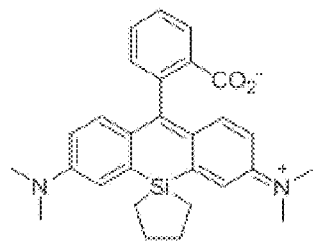
Figure 1K:
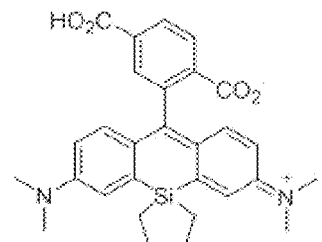
Figure 1N:
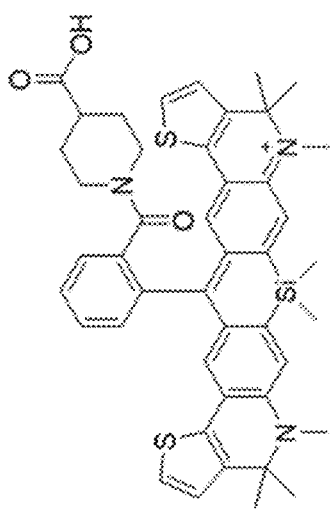
FIG. 1N shows the structures of Compounds 47, 48, 49 and 50.
Figure 1N:
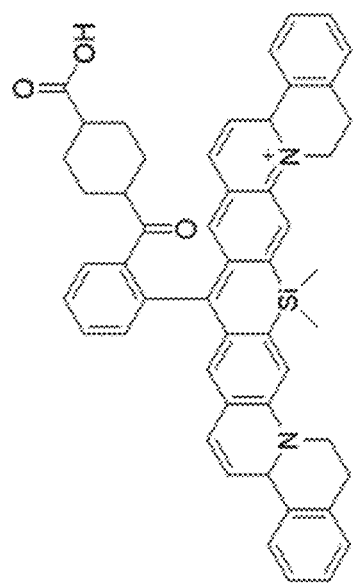
Figure 1N:
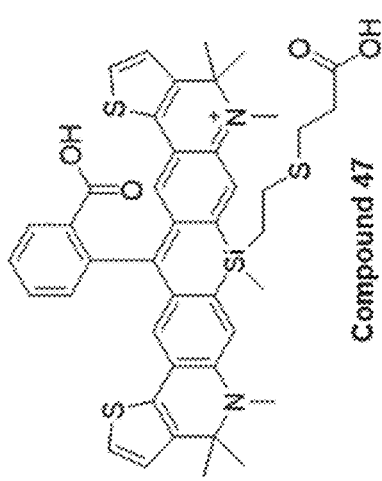
Figure 1N:
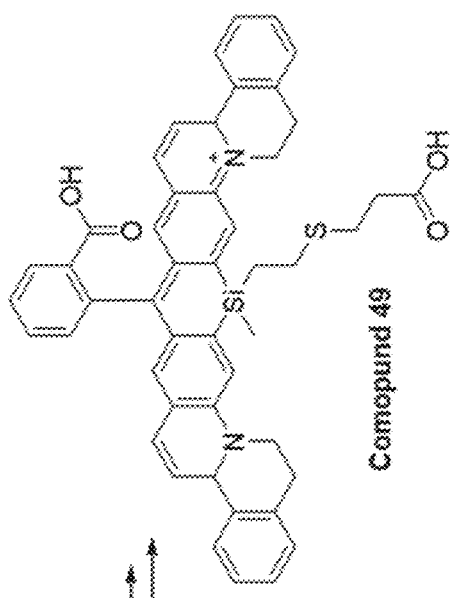
Figure 1N:
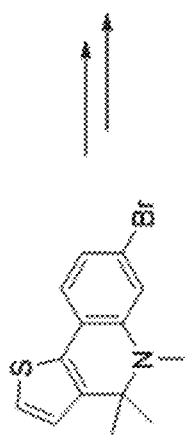
Figure 1N:
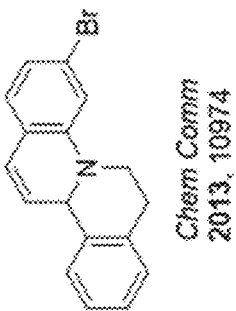
Figure 1P:
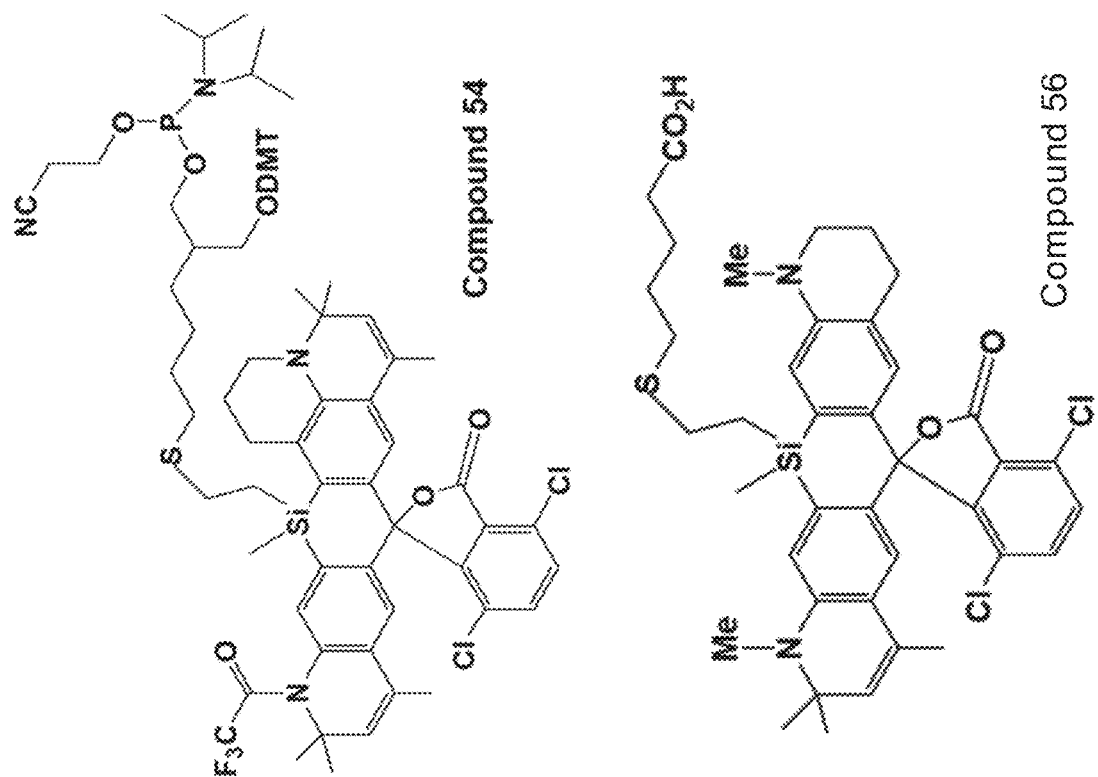
FIG. 1P shows the structures of Compounds 53, 54, 55 and 56.
Figure 1P:
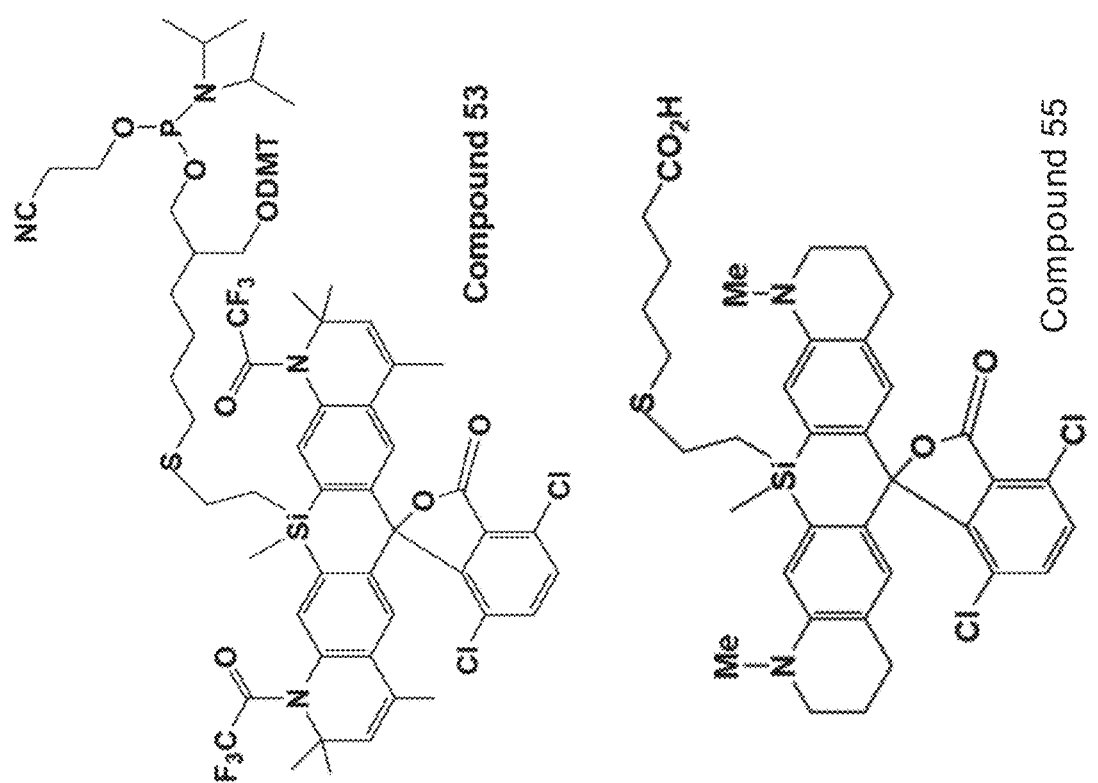
Figure 1Q:
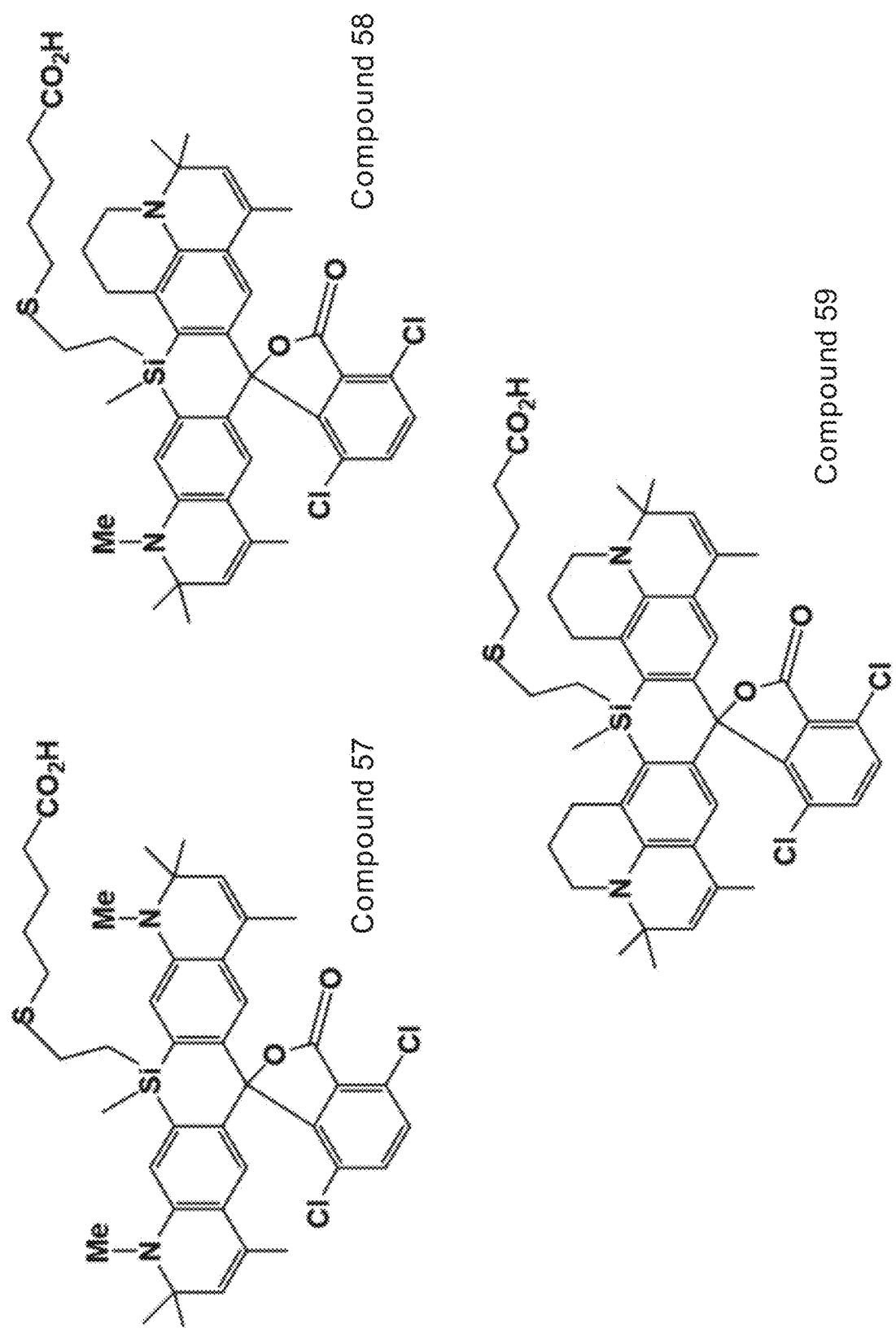
FIG. 1Q shows the structures of Compounds 57, 58 and 59.

Also disclosed are Compounds 1, 1A, 1B, 1C, 2, 2A, 3, 4A, 5, 6, 7, 7A, 7B, 8, 9, 10A, 10B, 11, 12, 13, 14, 15, 16, 17, 18, 19, 20, 21, 22, 23, 24, 25, 26, 27, 28, 29, 30, 31, 32, 33, 34, 35, 36, 37, 38, 39, 43, 45, 46, 47, 48, 49, 50, 51, 52, 53, 54, 55, 56, 57, 58, and 59 shown in FIGS. 1A-1Q. Although counterions such as triethylamine are shown with certain compounds such as compounds 10A-13, reference to such compounds does not include a particular counterion unless expressly indicated. As such, for example, "Compound 10A" includes salts with other cations as well as the corresponding free sulfonic acid (sulfonyl hydroxide). Similarly, in some cases precursors, side products, reagents, etc. are illustrated, e.g., with Compound 45; these are for informational purposes only and do not limit the structure of the compound itself. Substituents such as $R^1$, $R^2$, etc., can have the values set forth in any one of the embodiments set forth above and in the claims, e.g., the values set forth for Formula (I) in embodiment 1.

Also disclosed are compounds wherein $R^1$, $R^2$, $R^3$, $R^4$, E, $R^5$, $R^6$, $R^7$, $R^8$, $R^9$, $R^{N1}$, or $R^{N2}$ have the values set forth in any one of the embodiments set forth above and in the claims.

The selected compounds listed as Compounds 1, 1A, 1B, 1C, 2, 2A, 3, 4A, 5, 6, 7, 7A, 7B, 8, 9, 10A, 10B, 11, 12, 13, 14, 15, 16, 17, 18, 19, 20, 21, 22, 23, 24, 25, 26, 27, 28, 29, 30, 31, 32, 33, 34, 35, 36, 37, 38, 39, 43, 45, 46, 47, 48, 49, 50, 51, 52, 53, 54, 55, 56, 57, 58, and 59 above are not intended to be an exclusive list of the dyes of the present disclosure. Numerous modifications, substitutions, and alterations in substituents and compound structure are possible without departing from the spirit and scope of the disclosure. For example, as described herein, conjugates of compounds described herein are also provided.

Figure 1R:
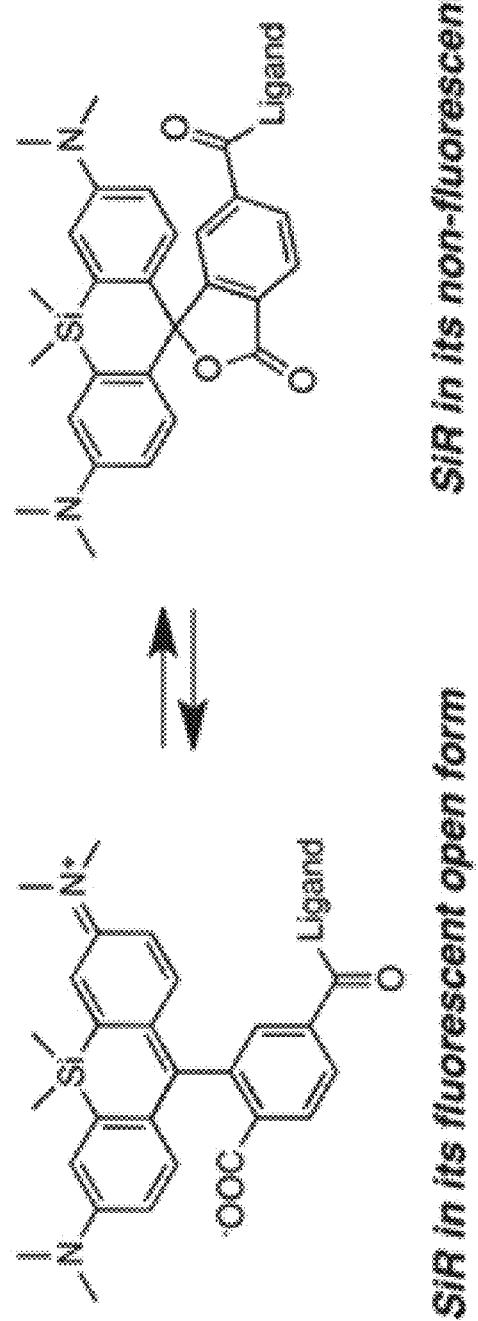

SiR compounds of the present disclosure comprising a 2'-carboxyl group on the phenyl ring (i.e., the $R^3$ position in formula (I)) can exist in equilibrium between a spirolactone (which may be non-fluorescent) and a fluorescent form (e.g., zwitterion). See FIG. 1R. Isomerization to a spirolactone form can render the SiR compound cell-permeable. Accordingly, also provided herein are spirolactone forms of SiR compounds disclosed herein, e.g., spirolactone forms of SiR compounds comprising a 2'-carboxyl group on the phenyl ring disclosed herein. Spirolactonization may be favored when the dye is unbound (perhaps, without wishing to be bound by any particular theory, due to hydrophobic aggregation of free dye molecules), while the fluorescent zwitterionic state may be favored when associated with a target. Thus, the dye can exhibit target-binding-dependent fluorogenicity in that a non-fluorescent spirolactone form converts to a fluorescent zwitterion upon target binding.

Alternatively, $R^3$ substituents other than a 2'-carboxyl group can prevent spirolactonization and result in the dye being unable to isomerize out of a fluorescent state and/or render the SiR dye of the present disclosure live-cell impermeant. Such dyes can be useful for live/dead cell discrimination. Such dyes can further be conjugated to target-binding moieties as described elsewhere herein, which can increase their residence time inside permeable and/or dead cells and/or the fluorescence differential in live/dead cell discrimination experiments.

In some embodiments, compounds exhibiting near-infrared fluorescence are provided. Fluorescence of an SiR compound of the present disclosure can be red-shifted by including additional rings in the fused ring system of the SiR. For example, an $R^{N1}$ and $R^5$ can together form a ring, and $R^6$ and an $R^{N2}$ can together form a ring. Rings formed by $R^{N1}$ and $R^5$ and $R^6$ and an $R^{N2}$ can each be further fused to at least one additional ring. Alternatively or in addition, an $R^{N1}$ and $R^7$ can together form a ring, and $R^B$ and an $R^{N2}$ can together form a ring. In some embodiments, a compound comprises a fused ring system comprising at least 5 rings. In some embodiments, a compound comprises a fused ring system comprising at least 7 rings. In some embodiments, a compound comprises a fused ring system comprising at least 9 rings. In some embodiments, any one of the foregoing fused ring systems consists of 5- and 6-membered rings. In some embodiments, any one of the foregoing fused ring systems consists of 6-membered rings. Exemplary compounds comprising a fused ring system of 5 or more rings are compounds 18-37 and 45-59. In some embodiments, the fused ring system of any one of the foregoing compounds is combined with $R^1$, $R^2$, $R^3$, and $R^4$ as defined for formula (I) or as set forth in any embodiment disclosed herein, including $R^1$, $R^2$, $R^3$, and $R^4$ of another SiR compound or $R^1$, $R^2$, $R^3$, and $R^4$ as defined in any numbered embodiment or claim.

In some embodiments, the compound has a plane of mirror symmetry passing through the silicon and $R^4$ of formula (I), optionally with the exception that $R^1$ and $R^2$ are not necessarily identical. A formal charge on the nitrogen attached to $R^{N1}$ or the nitrogen attached to $R^{N2}$ and the formal locations of double bonds that can rearrange through resonance or delocalize in molecular orbitals or a conjugated pi system are not considered symmetry-disrupting. Additionally, $R^3$ and E are generally not symmetry-disrupting to the extent that they can occupy the plane of symmetry through rotation of the bond between the ring to which they are bound and the ring system comprising the silicon. Thus, for example, Compound 1A has a plane of mirror symmetry passing through the silicon and $R^4$ of formula (I), and Compound 1 has a plane of mirror symmetry passing through the silicon and $R^4$ of formula (I) with the exception that $R^1$ and $R^2$ are not identical.

Those of skill in the art will appreciate that compounds may exhibit the phenomena of tautomerism, conformational isomerism, geometric isomerism and/or stereo isomerism. As the formulae drawings within this specification and claims cannot necessarily represent all of the possible tautomeric, conformational isomeric, enantiomeric or geometric isomeric forms, it should be understood that the disclosure encompasses any tautomeric, conformational isomeric, enantiomeric and/or geometric isomeric forms of the compounds having one or more of the utilities described herein.

In addition, it will also be apparent that the compounds may exist in many different protonation states, depending on, among other things, the pH of their environment. While the structural formulae provided herein depict the compounds in only one of several possible protonation states, it will be understood that these structures are illustrative only, and that the disclosure is not limited to any particular protonation state. Any and all protonated forms of the SiR compounds are intended to fall within the scope of the disclosure.

Furthermore, the compounds of the disclosure may bear multiple positive or negative charges. The associated counter ions with the enzyme substrates are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the disclosure, and that the disclosure encompasses the compounds in association with any type of counter ion unless otherwise specified.

In certain embodiments of the present disclosure, a composition is provided, the composition comprising any of the compounds provided herein and at least one solvent. In certain embodiments, the solvent comprises water or DMSO, or a combination thereof. In certain embodiments, the composition further comprises a culture medium.

In certain embodiments, compositions are provided, the compositions comprising: a) one or more of the compounds provided herein; and b) a carrier.

In certain embodiments, compositions are provided, the compositions comprising: a) one or more of the compounds provided herein; and b) an analyte.

2. Reactive Groups, Carrier Molecules and Solid Supports

In an exemplary embodiment, the SiR compounds provided herein comprise a reactive group or reactive ligand which is a member selected from an acrylamide, an activated ester of a carboxylic acid, an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine, a hydrazide, an imido ester, an isocyanate, an isothiocyanate, a maleimide, a phosphoramidite, a reactive platinum complex, a sulfonyl halide, a thiol group, and a photoactivatable group. In some embodiments, a compound comprises a reactive group or reactive ligand useful for conjugation to another molecule. Exemplary reactive groups and/or ligands include, but are not limited to, N-hydroxy succinimide (NHS) ester, carboxyl, carboxylester, maleimide, amide, sulfodichlorophenyl (SDP) ester, sulfotetrafluorophenyl (STP) ester, tetrafluorophenyl (TFP) ester, pentafluorophenyl (PFP) ester, acetoxymethyl (AM) ester, nitrilotriacetic acid (NTA), aminodextran and cyclooctyne-amine.

These reactive groups can be covalently attached either during or after the synthesis of the SiR compounds provided herein in order to provide reactive group-containing SiR compounds. In this way, reactive group-containing SiR compounds can be covalently attached to a wide variety of carrier molecules or solid supports that contain or are modified to contain functional groups with suitable reactivity, resulting in chemical attachment of the components. In an exemplary embodiment, the reactive group of a SiR compound disclosed herein and the functional group of the carrier molecule of solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the SiR compound to the carrier molecule or solid support.

For example, a general protocol for conjugating an NHS ester to a linker or molecule with a nucleophilic group (e.g., amino group or sulfhydryl) entails dissolving the NHS ester in aqueous acetonitrile (the percentage of acetonitrile is determined by the hydrophobicity of the dye to attain solubility) with linker in water (or aqueous acetonitrile solution if the linker is hydrophobic). Aqueous sodium bicarbonate buffer (1 M) is added to the solution to achieve 0.1M buffer concentration while vortexing or shaking. The mixture is shaken at room temperature for 10 minutes to 30 minutes. The crude conjugate in the reaction mixture can be purified by reverse-phase HPLC.

Selected examples of functional groups and linkages are shown in Table 1, where the reaction of an electrophilic group and a nucleophilic group yields a covalent linkage. One skilled in the art can select an appropriate pairing of groups depending on the identity of the compounds being conjugated, the reactivity of other moieties in those compounds (e.g., to avoid undesired side products), and the properties desired for the covalent linkage. Accordingly, in some embodiments, a reactive ligand is selected from an electrophilic group or nucleophilic group listed in Table 1. In some embodiments, the reactive group or reactive ligand of a compound is selected from an electrophilic group listed in Table 1. In some embodiments, the reactive group or reactive ligand of a compound is selected from a nucleophilic group listed in Table 1.

TABLE 1

Examples of some routes to useful covalent linkages

| Electrophilic Group | Nucleophilic Group | Resulting Covalent Linkage |
| --- | --- | --- |
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a suitable leaving group (e.g., succinimidyloxy (—OC$_4$H$_4$O$_2$), sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^x$ or —OCNR$^x$NHR$^y$, where R$^x$ and R$^y$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates.

The choice of the reactive group used to attach a SiR compound of the present disclosure to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantification.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. In this way, SiR compounds provided herein that comprise a photoactivatable reactive group associate with anionic proteins and can be covalently conjugated to the proteins. Photoactivatable reactive groups include, without limitation, benzophenones, aryl azides and diazirines.

In certain embodiments, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. In certain embodiments, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

The selection of a covalent linkage to attach the reporter molecule to the carrier molecule or solid support typically depends on the chemically reactive group on the component to be conjugated. The discussion regarding reactive groups in the section immediately preceding is relevant here as well. In addition to the hydrazinyl appendage, exemplary reactive groups typically present on the biological or non-biological components include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A carrier molecule or solid support may be conjugated to more than one reporter molecule, which may be the same or different, or to a substance that is additionally modified by a hapten. Although some selectivity can be obtained by careful control of the reaction conditions, selectivity of labeling is best obtained by selection of an appropriate reactive compound.

Where a conjugate of a SiR compound of Formula (I) is formed, the product is still considered a compound of Formula (I), in which the newly conjugated material is considered bonded to an SiR moiety through one of the pendent groups of Formula (I), e.g., $R^1$, $R^2$, $R^3$, $R^4$, E, $R^5$, $R^6$, $R^7$, $R^8$, $R^9$, $R^{N1}$ or $R^{N2}$.

Carrier Molecules:

In another exemplary embodiment, the SiR compound of the present description is covalently bound to a carrier molecule. If the compound has a reactive group (or reactive ligand), then the carrier molecule can alternatively be linked to the compound through the reactive group. The reactive group may contain both a reactive functional moiety and a linker, or only the reactive functional moiety.

A variety of carrier molecules are useful in the present disclosure. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In another exemplary embodiment, at least one member selected from $R^1$, $R^2$, $R^3$, $R^4$, E, $R^5$, $R^6$, $R^7$, $R^8$, $R^9$, $R^{N1}$, or $R^{N2}$ comprises a carrier molecule. In another exemplary embodiment one of $R^1$, $R^2$, $R^3$, $R^4$, E, $R^5$, $R^6$, $R^7$, $R^8$, $R^9$, $R^{N1}$, or $R^{N2}$ comprises a carrier group bound through a substituted alkyl group or reactive group, such as an alkyl-succinimidyl group.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorescent proteins.

Antibody binding proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCOalkyl$ and combinations thereof. Thus, the enzyme substrates can be cleaved by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis OR), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL (GE Healthcare, Fairfield, CT), heparin, glycogen, amylopectin, mannan, inulin, starch, agarose and cellulose, or is a polymer such as a polyethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye compound into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier molecule is a metal chelating moiety.

While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Raju et al., *Am. J. Physiol,* 256: C540 (1989); and pyridyl-based and phenanthroline metal ion chelators, as described in U.S. Pat. No. 5,648,270 to Kuhn et al. (1997).

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect an analyte in a sample. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization Solid Supports:

In certain embodiments, the SiR compounds disclosed herein are covalently bonded to a solid support. The solid support may be attached to the SiR compounds either through the fluorophore, or through a reactive group, if present, or through a carrier molecule, if present.

Solid supports suitable for use herein are typically substantially insoluble in liquid phases. Solid supports for use herein are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as SEPHAROSE (GE Healthcare, Fairfield, CT), poly (acrylate), polystyrene, poly(acrylamide), polyol, agarose, agar, cellulose, dextran, starch, FICOLL (GE Healthcare), heparin, glycogen, amylopectin, mannan, inulin, nitrocellulose, diazocellulose, polyvinylchloride, polypropylene, polyethylene (including polyethylene glycol)), nylon, latex bead, magnetic bead, paramagnetic bead, superparamagnetic bead, starch and the like.

In certain embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc, for attaching the dye compounds disclosed herein. Useful reactive groups are disclosed above and are equally applicable to the solid support reactive functional groups herein.

A suitable solid phase support may be selected on the basis of desired end use and suitability for various synthetic protocols. For example, where amide bond formation is desirable to attach the SiR compounds disclosed herein to the solid support, resins generally useful in peptide synthesis may be employed, such as polystyrene (e.g., PAM-resin obtained from Bachem Inc., Peninsula Laboratories, etc), POLYHIPE resin (obtained from Aminotech, Canada), polyamide resin (obtained from Peninsula Laboratories), polystyrene resin grafted with polyethylene glycol (TENTA-GEL, Rapp Polymere, Tubingen, Germany), polydimethylacrylamide resin (available from Milligen/Biosearch, California), or PEG A beads (obtained from Polymer Laboratories).

3. Conjugates to Target-Binding Moieties

In general, with respect to compounds described herein comprising an SiR moiety and a conjugated moiety (e.g., target-binding moiety, nucleotide, polynucleotide, phosphoramidite, etc.), the SiR moiety has the structure of Formula (I) wherein a substituent thereof (e.g., $R^1$, $R^2$, $R^3$, $R^4$, E, $R^5$, $R^6$, $R^7$, $R^8$, $R^9$, $R^{N1}$, or $R^{N2}$) comprises the conjugated moiety, which is optionally connected to the SiR moiety through a linker. In some embodiments, $R^1$ or $R^2$ comprises the conjugated moiety. In some embodiments, $R^3$ or $R^4$ comprises the conjugated moiety.

In some embodiments, a conjugate is provided in which a SiR moiety is joined to a target-binding moiety, such as an antibody, cytoskeleton-binding moiety, or nucleic-acid binding moiety. SiR compounds comprising target-binding moieties can be used to fluorescendy stain the target bound by the target-binding moiety, e.g., for fluorescence microscopy and super-resolution microscopy applications described elsewhere herein.

For example, to prepare such conjugates, a reactive group of the target-binding moiety (e.g., an amine on an antibody) can be reacted with a reactive group, such as an NHS ester, on a compound of Formula (I), to provide a conjugate according to the disclosure. In some embodiments, a compound disclosed herein is first activated by converting a moiety thereof to a reactive ligand that reacts with the target-binding moiety. The products of such conjugation reactions are also considered compounds disclosed herein.

Figure 2A:
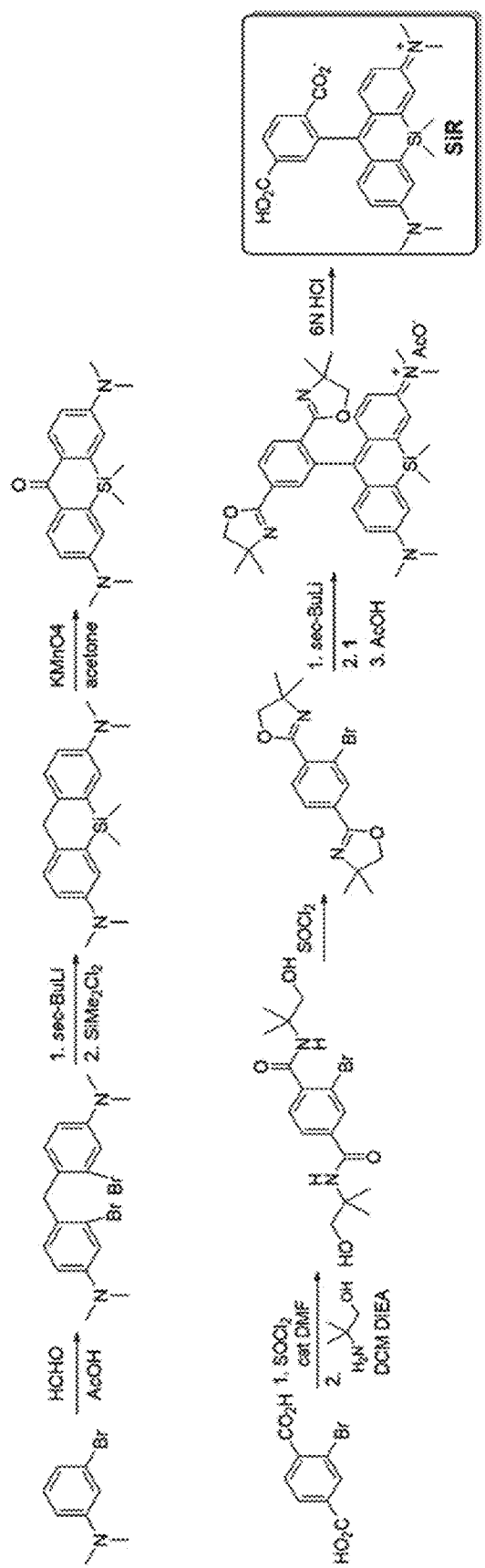
FIGS. 2A-2E illustrate preparation of various SiR compounds.
Figure 2B:
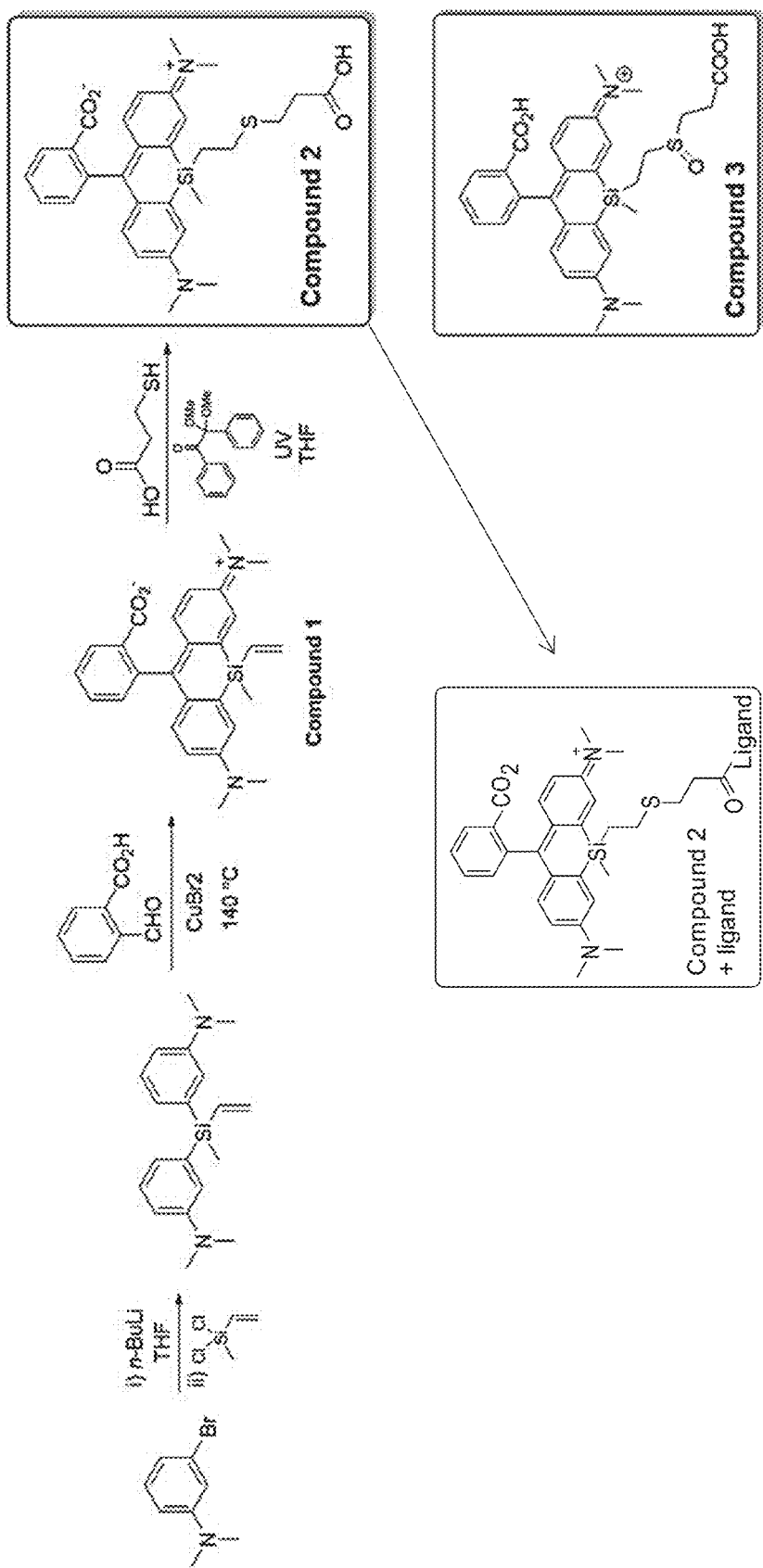
Figure 2C:
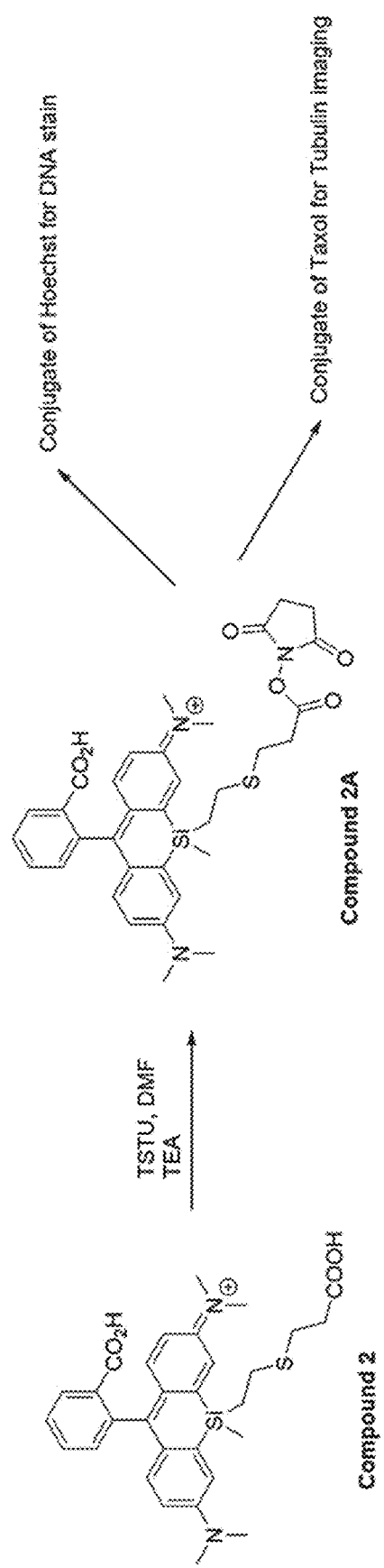
Figure 2D:
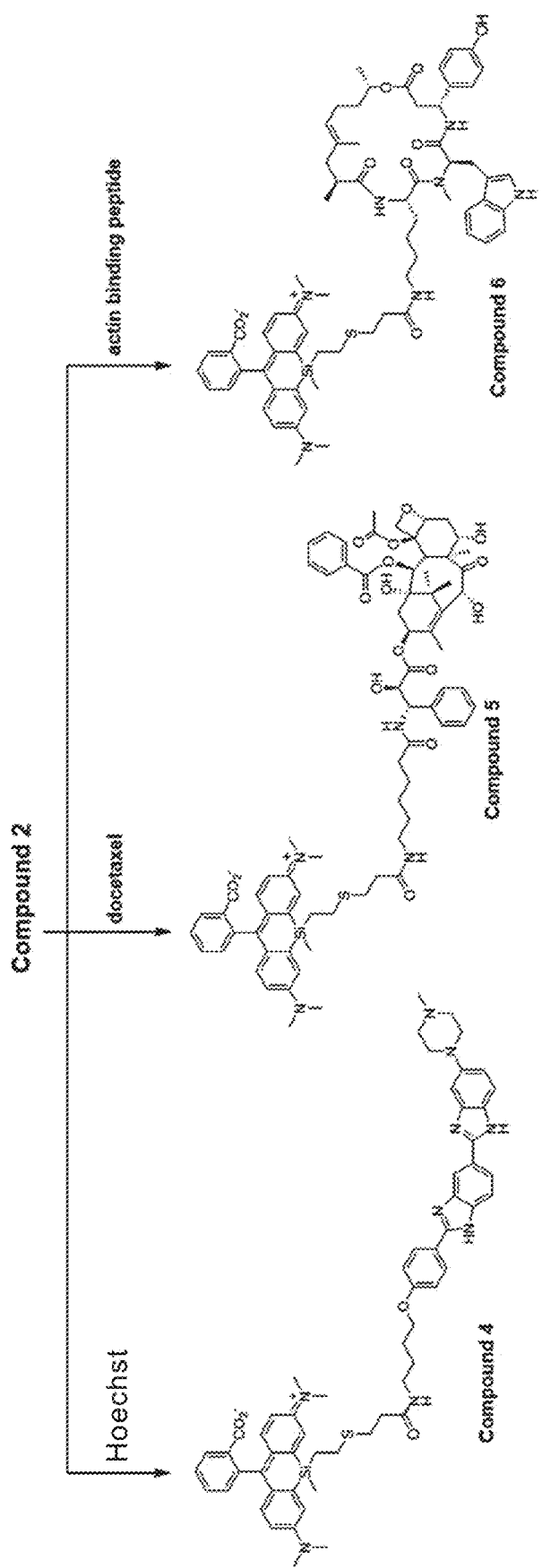

Accordingly, in some embodiments, a compound of Formula (I) comprises a target-binding moiety. In some embodiments, the target-binding moiety is part of $R^1$, $R^2$, $R^3$, or $R^4$ of Formula (I). The target-binding moiety can be conjugated to the SiR moiety, e.g., at one of the foregoing positions, using appropriate derivatization procedures, e.g., starting from a compound of Formula (I) in which $R^1$, $R^2$, $R^3$, or $R^4$ comprises a reactive ligand, e.g., a vinyl at $R^1$ or $R^2$ (or a different reactive group such as a carboxyl or amine, which can be provided, e.g., using a thiol-ene reaction as discussed elsewhere herein; see FIGS. 2B-2D for exemplary synthetic routes involving derivatization at $R^2$, which can be applied mutatis mutandis to derivatization at $R^1$), or a reactive ligand such as a carboxyl at $R^3$ or $R^4$. See FIG. 2E for an exemplary synthetic route involving derivatization at $R^3$, which can be applied mutatis mutandis to derivatization at $R^4$.

In some embodiments, the target binding moiety is a cytoskeleton-binding moiety.

In some embodiments, the cytoskeleton-binding moiety is a microtubule-binding moiety, such as docetaxel. An exemplary structure of a conjugated docetaxel is

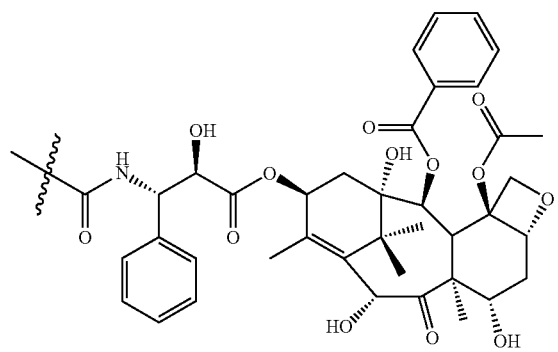

where the wavy line indicates the connection to the SiR moiety, e.g., through a linker. See, e.g., Compound 5.

In some embodiments, the cytoskeleton-binding moiety is an actin-binding peptide. An exemplary structure of a conjugated actin-binding peptide is

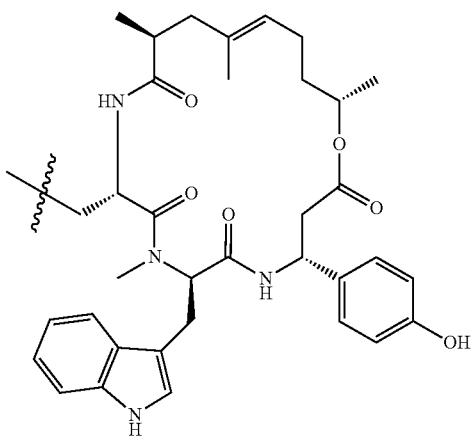 [SMILES: *C[C@@H]1NC(=O)[C@@H](C)C/C(C)=C/CC[C@H](C)OC(=O)C[C@H](c2ccc(O)cc2)NC(=O)[C@@H](Cc2c[nH]c3ccccc23)N(C)C1=O]

where the wavy line indicates the connection to the SiR moiety, e.g., through a linker. See, e.g., Compound 6.

In some embodiments, the target-binding moiety is an actin-binding moiety, such as a phalloidin. An exemplary phalloidin conjugate can be prepared using a silicon rhodamine, such as Compound 7A.

In some embodiments, the target-binding moiety is a nucleic acid-binding moiety, such as a DNA-binding moiety. An exemplary nucleic acid-binding moiety is a Hoechst moiety or nitro-Hoechst moiety. An exemplary structure of a conjugated Hoechst moiety is

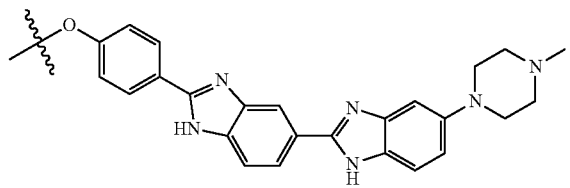 [SMILES: *Oc1ccc(-c2nc3cc(-c4nc5cc(N6CCN(C)CC6)ccc5[nH]4)ccc3[nH]2)cc1]

where the wavy line indicates the connection to the SiR moiety, e.g., through a linker. See, e.g., Compounds 4 and 7. An exemplary structure of a conjugated nitro-Hoechst moiety is

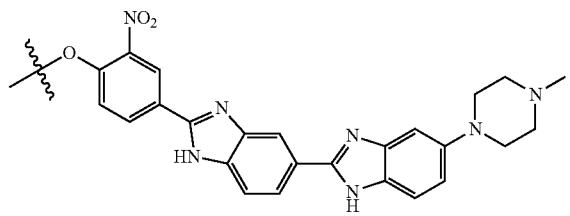 [SMILES: *Oc1ccc(-c2nc3cc(-c4nc5cc(N6CCN(C)CC6)ccc5[nH]4)ccc3[nH]2)cc1[N+](=O)[O-]]

where the wavy line indicates the connection to the SiR moiety, e.g., through a linker. See, e.g., Compound 7B. In applications that may involve another dye with fluorescence spectra overlapping those of Hoechst, it may be desirable to use a nitro-Hoechst moiety, which has reduced fluorescence bleed-through (see Example 4).

Figure 10:
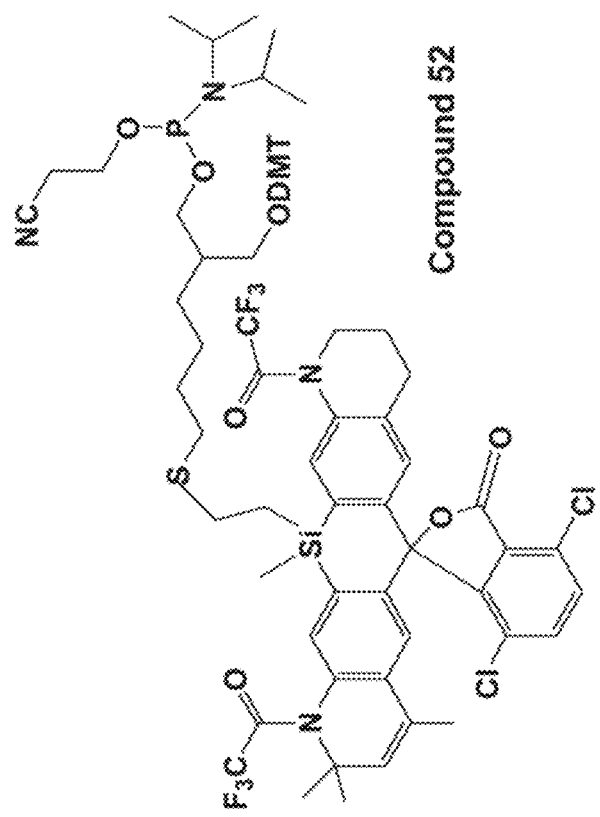
FIGS. 10A-10B show the structures of exemplary compounds useful for laboratory procedures such as staining fixed cells or labelling antibodies.
Figure 10:
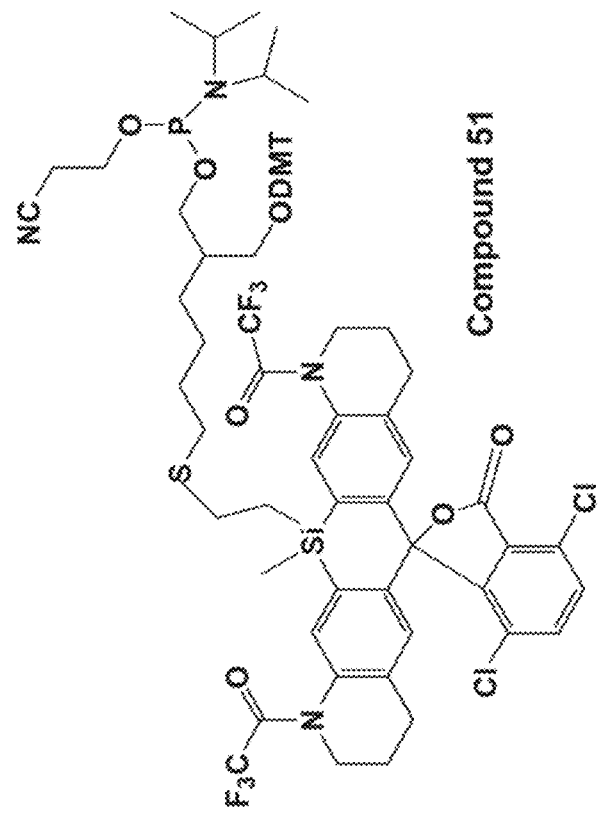

See FIG. 10A for a general illustration of preparation of a conjugate for staining fixed cells involving derivatization at the $R^3$ position.

4. Phosphoramidites and Labeled Nucleosides, Nucleotides, and Polynucleotides

Also provided herein are compounds according to Formula (I) that comprise a phosphoramidite. The phosphoramidite can be part of the $R^1$, $R^2$, $R^3$, or $R^4$ groups of Formula (I).

In some embodiments, the compound is a phosphoramidite compound having the Formula (L1):

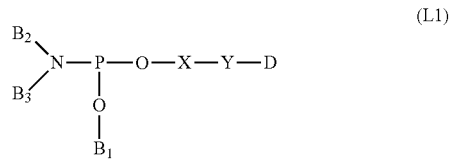

(L1)

wherein X and Y together form a linker; $B_1$ is a phosphite ester protecting group; $B_2$ and $B_3$ taken separately are lower alkyl, lower alkene, aryl, and cycloalkyl containing up to 10 carbon atoms; and D is the SiR-containing dye moiety. Such compounds are suitable for labeling the 5'-end of a chemically-synthesized polynucleotide or a chemically-automatable-synthesized polynucleotide using solid-support synthesis through the sugar-portion of the nucleotide. Y can be attached to D through one of positions $R^1$, $R^2$, $R^3$, or $R^4$ of Formula (I). X and Y may take a variety of forms, however, the structure X—Y must be such that (i) it is stable to DNA synthesis conditions, (ii) does not substantially interfere with polynucleotide-target hybridization, and (iii) does not quench the fluorescence of the dye to which it is attached, e.g., U.S. Pat. Nos. 5,231,191, 5,258,538, and 4,757,141 and 5,212,304. In some embodiments, X is linear or cyclic lower alkyl, linear or cyclic substituted lower alkyl, polyethylene oxide, lower aryl having between 1 and 8 carbon atoms, peptide, or polyether. In some embodiments, Y is amido, sulfonamido, urea, urethane, or thiourea. For example, Y can be amido and X can be —$(CH_2)_n$— where n ranges from 2 to 30, e.g., from 2 to 10, such as from 2 to 6. In another example, Y can be amido and X can be —$(CH_2CH_2O)_n$— (i.e., linear polyethylene oxide) where n ranges from 2 to 30, e.g., from 2 to 10, such as from 2 to 6.

Phosphoramidite compounds may be synthesized by a variety of known methods. Generally, the synthesis proceeds as follows. Phenolic hydroxyls of D, if any, are protected with dye-protecting groups that can be removed with a DNA synthesis deprotection agent, e.g., ammonia, ethanolamine, methylamine/ammonium hydroxide mixtures, and mixtures of t-butylamine/water/methanol (1:2:1), e.g., see U.S. Pat. No. 5,231,191. Dyes so protected are referred to herein as "protected derivatives" of the dye. In some embodiments, the protecting group is an ester of benzoic acid or pivalic acid. The reactive ligand of the protected dye, e.g., carboxylic acid, is then activated, e.g., with carbodiimide, and reacted with an alcohol linker derivative, e.g., an amino alcohol, e.g., ethanolamine, hexanol amine, or the like, in N,N-dimethylformamide (DMF), or another like aprotic solvent to yield a protected dye with a free alcohol functionality, e.g., alcohol-amide derivative. The free alcohol is then reacted with a phosphitylating agent using standard procedures, e.g., di-(N,N-diisopropylamino)methoxyphosphine in acetonitrile containing catalytic amounts of tetrazole diisopropylamine, to yield the phosphoramidite, e.g., U.S. Pat. No. 5,231,191.

In some embodiments, a polynucleotide labeled with an SiR moiety described herein is provided. Such a polynucleotide can be produced, e.g., by labeling the 5'-end of a chemically-synthesized or chemically-automatable-synthesized polynucleotide using solid-support synthesis through the sugar-portion of the nucleotide with a compound of Formula (L1). Alternatively, a polynucleotide comprising a first reactive ligand (e.g., nucleophilic reactive ligand, such as a primary amine) can be labeled by reacting it with a compound of Formula (I) comprising a second reactive ligand compatible with the first reactive ligand (e.g., electrophilic reactive ligand, such as an active ester, e.g., an NHS ester).

In some embodiments, a phosphoramidite compound is provided having the Formula (L2):

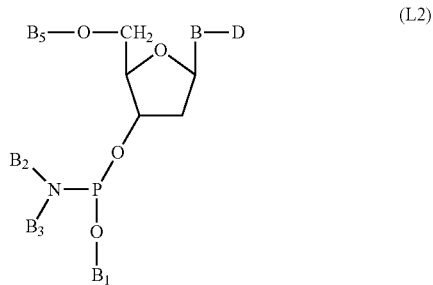

(L2)

wherein the variable substituents are defined as follows. $B_1$ is a phosphite ester protecting group; $B_2$ and $B_3$ taken separately are lower alkyl, lower alkene, aryl, or cycloalkyl containing up to 10 carbon atoms; $B_5$ is hydrogen or an acid-cleavable hydroxyl protecting group; B is a nucleoside/tide base, and D is the SiR-containing dye moiety. When B is purine or 7-deazapurine, the sugar moiety is attached at the $N^9$-position of the purine or 7-deazapurine, and when B is pyrimidine, the sugar moiety is attached at the $N^1$-position of the pyrimidine. B and D are linked through a linker attached to D at one of positions $R^1$, $R^2$, $R^3$, or $R^4$. If B is a purine, the linker is attached to the 8-position of the purine, if B is 7-deazapurine, the linker is attached to the 7-position of the 7-deazapurine, and if B is pyrimidine, the linker is attached to the 5-position of the pyrimidine.

In some embodiments, $B_5$ is triphenylmethyl radical or an electron-donating-substituted derivative thereof, where, as used herein, the term "electron-donating" denotes the tendency of a substituent to release valence electrons to neighboring atoms in the molecule of which it is a part, i.e., it is electropositive with respect to neighboring atoms. In some embodiments, electron-donating substituents include amino, lower alkyl, lower aryl having between 1 and 8 carbon atoms, lower alkoxy, and the like. More preferably, the electron-donating substituents are methoxy. Exemplary trityls include 4,4'-dimethoxytrityl, i.e. bis(p-anisyl)phenylmethyl, monomethoxytrityl, α-naphthyldiphenylmethyl, tri(p-methoxyphenyl)methyl, and the like. Attachment and cleavage conditions for these and other trityls can be found in Greene and Wuts, Protective Groups in Organic Synthesis, 2nd Edition (John Wiley, New York, 1991).

Generally, nucleotide phosphoramidites of Formula (L2) may be synthesized as described in U.S. Pat. No. 9,783,560, herein incorporated by reference in its entirety.

Compounds of Formula (L2) are suitable for the internal labeling of chemically synthesized polynucleotides. Accordingly, also provided herein is a polynucleotide comprising a base labeled with an SiR moiety disclosed herein, e.g., wherein the base is bonded to the SiR moiety through $R^1$, $R^2$, $R^3$, or $R^4$ of Formula (I). Such labeled polynucleotides are useful in a number of important contexts including as DNA sequencing primers, PCR primers, polynucleotide hybridization probes, polynucleotide ligation probes, and the like. In some embodiments, a labeled polynucleotide further comprises a second dye or quencher located such that fluorescence energy transfer takes place between a donor dye and an acceptor dye or quencher. Such multi-dye or dye/quencher energy-transfer polynucleotides find application as spectrally-tunable sequencing primers, e.g., Ju et al., Proc. Natl. Acad. Sci. USA 92: 4347-4351 (1995), and as hybridization probes, e.g., Lee et al. Nucleic Acids Research, 21: 3761-3766 (1993); U.S. Pat. No. 5,723,591 (TaqMan probes); U.S. Pat. No. 8,211,644 (molecular beacon probes).

Also provided herein is a labeled nucleoside/tide having the structure

NUC-DYE wherein NUC is a nucleoside/tide or nucleoside/tide analog and DYE is a SiR-containing dye moiety described herein. NUC and DYE can be connected by a linker wherein the linker is attached to DYE through one of positions $R^1$ or $R^2$ of Formula (I). If NUC comprises a purine base, the linker can be attached to the 8-position of the purine; if NUC comprises a 7-deazapurine base, the linker can be attached to the 7-position of the 7-deazapurine; and if NUC comprises a pyrimidine base, the linker can be attached to the 5-position of the pyrimidine.

Nucleoside labeling can be accomplished using any one of a large number of known nucleoside/tide labeling techniques employing known linkers, linking groups, and associated complementary functionalities. Generally, the linker linking the SiR compound and nucleoside should (i) be stable to polynucleotide synthesis conditions, (ii) not interfere with polynucleotide-target hybridization, (iii) be compatible with relevant enzymes, e.g., polymerases, ligases, and the like, and (iv) not adversely affect the fluorescence properties of the dye. Exemplary base labeling procedures suitable for use include the following: Gibson et al, Nucleic Acids Research, 15:6455-6467 (1987); Gebeyehu et al, Nucleic Acids Research, 15: 4513-4535 (1987); Haralambidis et al, Nucleic Acids Research, 15: 4856-4876 (1987); Nelson et al., Nucleosides and Nucleotides, 5(3): 233-241 (1986); Bergstrom, et al., JACS, 111: 374-375 (1989); U.S. Pat. Nos. 4,855,225, 5,231,191, and 5,449,767.

In some embodiments, the linkers comprise acetylenic amido or alkenic amido groups, the linker between the dye and the nucleoside/tide base being formed by reacting an activated N-hydroxysuccinimide (NHS) ester of the dye with an alkynylamino- or alkenylamino-derivatized base of a nucleoside/tide. In further embodiments, the resulting linker is 3-(carboxy)amino-1-propyn-1-yl. In other embodiments, the linker comprises a substituted propargylethoxyamido group having the structure —C≡C—CH$_2$OCH$_2$CH$_2$NR$^{N6}$X—, wherein X is —C(O)—(CH$_2$)$_n$—N(R$^{N7}$)— where n ranges from 1 to 5, —C(O)—Ar—(CH$_2$)$_n$—N(R$^{N7}$)— where n ranges from 1 to 5, or —C(O)—C≡C—CH$_2$—N(R$^{N7}$)—; R$^{N7}$ is H, lower alkyl or protecting group; and R$^{N6}$ is H or lower alkyl. See U.S. Pat. No. 5,770,716, which is herein incorporated by reference.

In some embodiments, the labeled nucleoside/tide is a compound of Formula (L3):

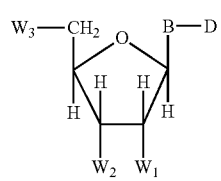

wherein B is a nucleotide base, e.g., uracil, cytosine, deazaadenine, or deazaguanosine; $W_1$ and $W_2$ taken separately are OH or a group capable of blocking polymerase mediated template-directed polymerization, e.g., H, fluorine and the like; $W_3$ is OH, or mono-, di- or triphosphate or phosphate analog; and D is an SiR moiety described herein, e.g., in which B is bonded to the SiR moiety through $R^1$, $R^2$, $R^3$, or $R^4$ of Formula (I). For example, the compound can be a dideoxynucleotide triphosphate in which $W_3$ is a triphosphate and $W_2$ and $W_1$ are H. Labeled dideoxy nucleotides find particular application as chain terminating agents, e.g., in Sanger-type DNA sequencing methods utilizing fluorescent detection. As another example, the compound can be a deoxynucleotide triphosphate in which $W_3$ is a triphosphate and $W_2$ and $W_1$ are OH and H, respectively. Such labeled deoxynucleotides find particular application in labeling polymerase extension products, e.g., in amplification reactions such as PCR or nick-translation.

Figure 8:
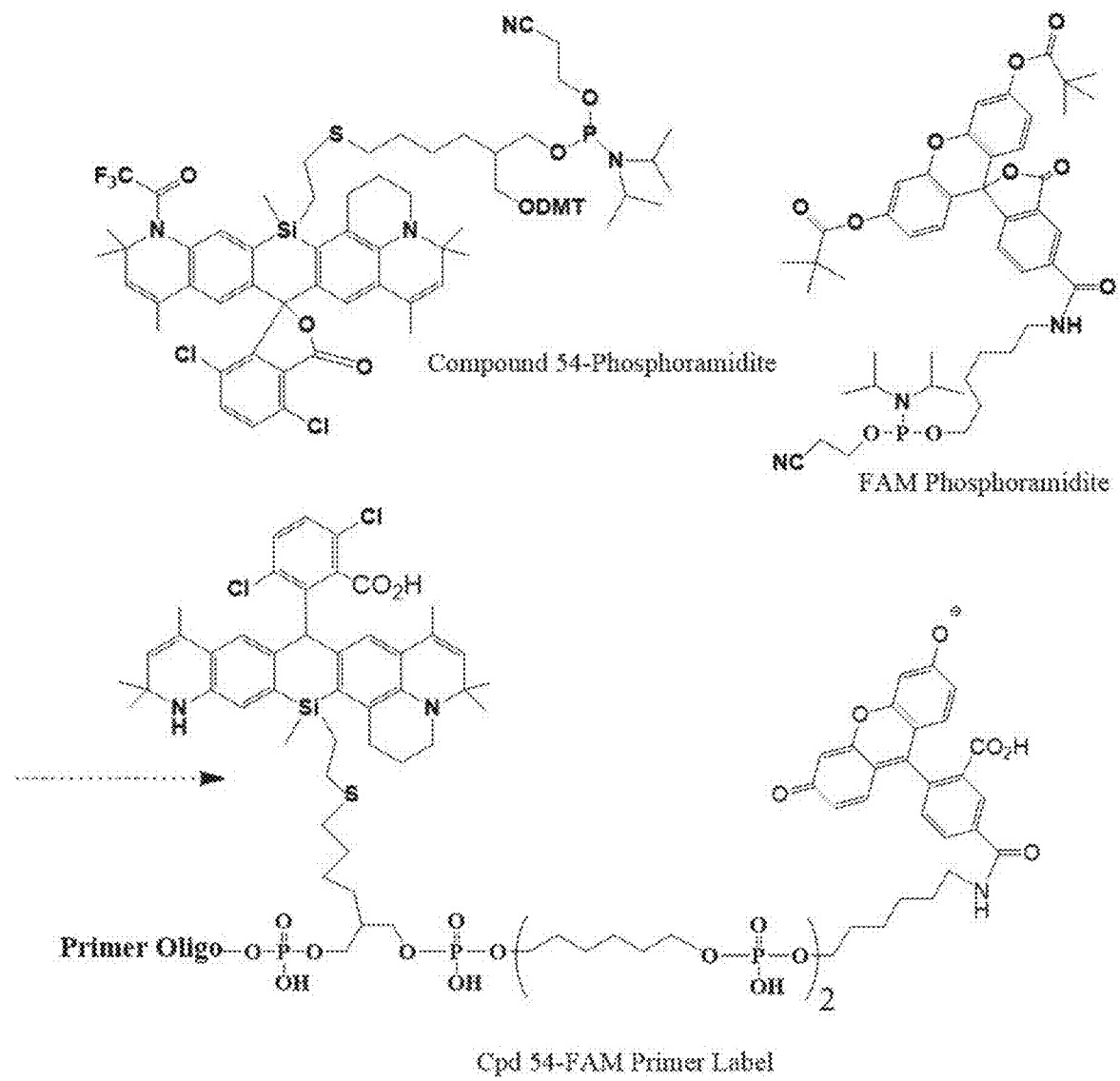
FIG. 8 illustrates using Compound 54-Phosphoramidite and FAM-Phosphoramidite for the generation of a Compound 54-FAM primer label that can be used to label polynucleotides or oligonucleotides, according to certain embodiments provided herein. The primer will emit above 650 nm.
Figure 9:
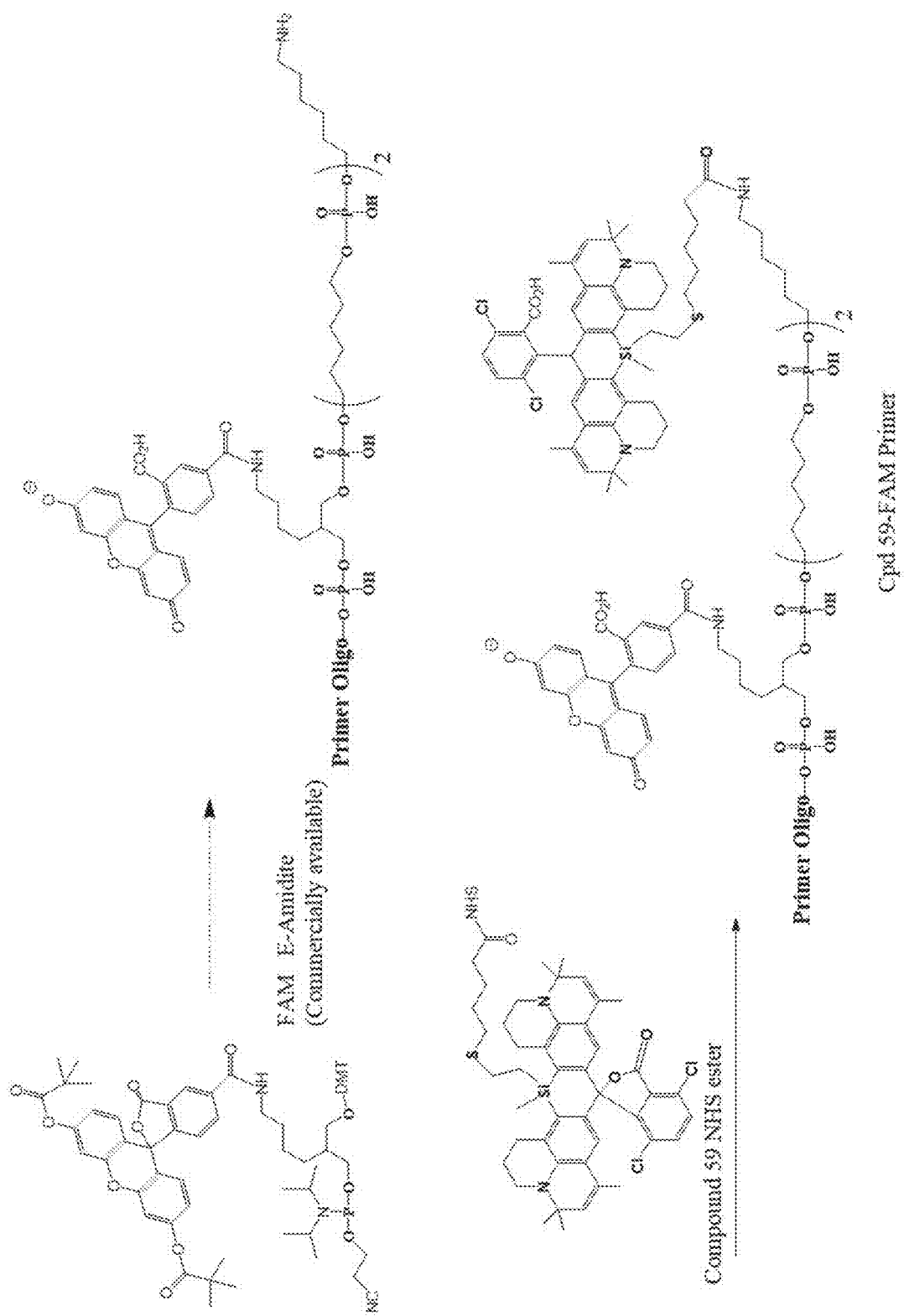
FIG. 9 illustrates the generation of a primer oligonucleotide conjugated to FAM and an SiR moiety derived from Compound 59 via an NHS ester thereof. The primer oligonucleotide is labeled by a Compound 59-FAM primer label, according to certain embodiments provided herein.

Preparation of an exemplary dual-labeled primer using a phosphoramidite compound according to the disclosure is illustrated in FIG. 8. Preparation of an exemplary dual-labeled primer using an NHS ester compound according to the disclosure is illustrated in FIG. 9.

For further discussion generally relevant to phosphoramidite compound, nucleoside, and nucleotide preparation, including useful reagents and reaction conditions, see U.S. Pat. Nos. 6,008,379 and 9,783,560, which are incorporated herein by reference.

5. Moieties to Increase Water Solubility

Increasing the water solubility of an SiR compound provided herein can be desirable, e.g., to allow use of the SiR compound at a higher concentration in an aqueous environment and/or to render the SiR compound impermeable to intact cell membranes of live cells. As such, in some embodiments, at least one, two, three, four, or more of $R^1$, $R^2$, $R^3$, $R^4$, E, $R^5$, $R^6$, $R^7$, $R^8$, $R^9$, $R^{N1}$, and $R^{N2}$ comprise one or more solubilizing functionalities, which are polar or charged (e.g., anionic, cationic, or zwitterionic) groups. In some embodiments, at least one, two, three, four, or more of $R^1$, $R^2$, $R^3$, $R^4$, E, $R^5$, $R^6$, $R^7$, $R^8$, $R^9$, $R^{N1}$, and $R^{N2}$ comprise one or more polar groups such as oxygen-, nitrogen-, or chlorine-containing groups and/or hydrogen bond donors or acceptors. In some embodiments, at least one, two, three, four, or more of $R^1$, $R^2$, $R^3$, $R^4$, E, $R^5$, $R^6$, $R^7$, $R^8$, $R^9$, $R^{N1}$, and $R^{N2}$ comprise one or more polar groups such as oxygen-, nitrogen-, or chlorine-containing groups. Exemplary solubilizing functionalities include carboxyls, amines, alcohols, nitros, chloros, carbonyls, esters, sulfates, sulfonates, phosphates, phosphonates, ethers (e.g., polyethylene oxides), amides, carbonates, carbamates, and the like.

In some embodiments, solubilizing functionalities can be provided as part of a linker. For example, a polyethylene oxide linker, $-(CH_2CH_2O)_n-$, can be provided, e.g., where n is 2, 3, 4, 5, 6, 7, 8, 9, 10, or more, such as at least 3. In some embodiments, such a linker can comprise a reactive ligand at one end useful for further derivatization, e.g., an NHS ester, carboxyl, carboxylester, maleimide, amide, sulfodichlorophenyl (SDP) ester, sulfotetrafluorophenyl (STP) ester, tetrafluorophenyl (TFP) ester, pentafluorophenyl (PFP) ester, acetoxymethyl (AM) ester or other reactive ligand described herein.

In some embodiments, solubilizing functionalities can be provided as substituents on an aryl or heteroaryl. In some embodiments, a compound comprises an aryl or heteroaryl (e.g., phenyl) substituted with at least 1, 2, or 3 solubilizing functionalities, which may be the same or different (e.g., sulfonates). In some embodiments, a compound comprises an aryl or heteroaryl (e.g., phenyl) substituted with at least 1, e.g., at least 2 sulfonates, such as 2 sulfonates in a meta orientation to each other.

An exemplary solubilizing substituent is one comprising a polyethylene oxide linker, reactive ligand, and phenyl substituted with 2 sulfonates, e.g.,

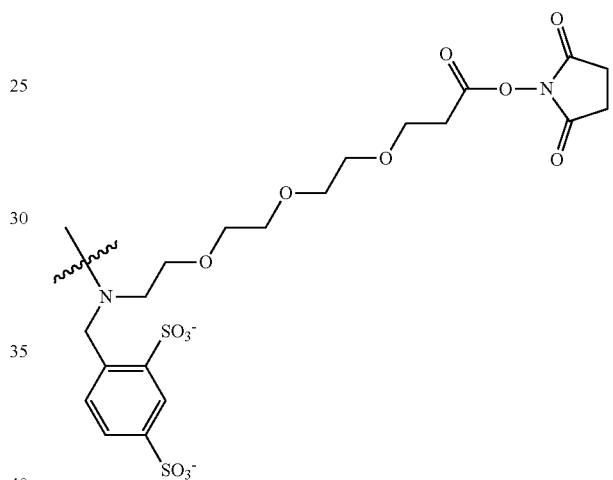

where the wavy line indicates the connection to the SiR moiety. See, e.g., compounds 10A-14. See also FIG. 10B. The amine of such a compound can be attached to a reactive ligand such as an acid chloride or other electrophile, e.g., generated by activation of a carboxyl. In some embodiments, a solubilizing substituent such as any of those discussed above is attached at the $R^3$ position of Formula (I). In some embodiments, a solubilizing substituent such as any of those discussed above is attached at the $R^4$ position of Formula (I).

6. Uses; Staining and Detection Methods

The SiR compounds and conjugates provided herein can be used in a variety of biological applications. The SiR compounds and conjugates have been found to have unexpected properties, including increased brightness and photostability without sacrificing other characteristics. It was surprisingly found that conjugation of the SiR compounds at the $R^1$ or $R^2$ position did not adversely affect the photochemical properties of the compounds; rather, the brightness and photostability was seen to be increased (see, for example, Compounds 4, 5 and 6).

In some embodiments, SiR compounds provided herein can be used to label or stain cells, cellular structures, organelles, target molecules, and the like. In some embodiments, methods of staining or labeling cells or cellular structures are provided, the methods comprising: a) contacting a sample containing one or more cells or cellular structures with a SiR compound of Formula (I) to form a contacted sample; b) incubating the contacted sample for an appropriate amount of time to form an incubated sample; c) illuminating the sample with an appropriate wavelength to form an illuminated sample; and d) detecting fluorescence emission from the illuminated sample.

In some embodiments, methods of detecting target molecules are provided, the methods comprising: a) contacting a sample containing or thought to contain a target molecule with a SiR compound of Formula (I) to form a contacted sample; b) incubating the contacted sample for an appropriate amount of time to form an incubated sample; c) illuminating the sample with an appropriate wavelength to form an illuminated sample; and d) detecting fluorescence emission from the illuminated sample, wherein the fluorescence emission is used to detect the target molecule.

In some embodiments, methods are provided for detecting a biological structure, the methods comprising: a) combining a sample that contains or is thought to contain a specific biological structure, with a SiR compound of Formula (I), wherein said biological structure contains nucleic acids; b) incubating the combined sample and SiR compound for a time sufficient for the SiR compound to combine with the nucleic acids in the biological structure to form a pattern of SiR-nucleic acid complexes having a detectable fluorescent signal that corresponds to the biological structure; and c) detecting the fluorescent signal that corresponds to the biological structure.

In some embodiments, the compounds used in the methods provided herein are selected from 1, 1A, 1B, 1C, 2, 2A, 3, 4A, 5, 6, 7, 7A, 7B, 8, 9, 10A, 10B, 11, 12, 13, 14, 15, 16, 17, 18, 19, 20, 21, 22, 23, 24, 25, 26, 27, 28, 29, 30, 31, 32, 33, 34, 35, 36, 37, 38, 39, 43, 45, 46, 47, 48, 49, 50, 51, 52, 53, 54, 55, 56, 57, 58, and 59, or an open or spirolactone form and/or salt or free acid thereof.

Labeled antibodies. In some embodiments, SiR moieties provided herein can be conjugated to antibodies as described herein to provide compounds of Formula (I) comprising an antibody. As such, methods for staining or detecting an antigen or cells, cellular components, tissues, etc., comprising an antigen are provided, the methods comprising contacting a sample suspected of comprising the antigen with a compound of Formula (I) comprising an antibody specific for the antigen. Also provided herein are methods for staining or detecting an antigen or cells, cellular components, tissues, etc., comprising an antigen are provided, the methods comprising contacting a sample suspected of comprising the antigen with a primary antibody specific for the antigen and contacting the primary antibody with a compound of Formula (I) comprising an antibody specific for the primary antibody (i.e., a secondary antibody labeled with an SiR moiety disclosed herein). Corresponding uses of such compounds of Formula (I) as primary or secondary antibodies to stain or detect an antigen of interest or cells, cellular components, tissues, etc., comprising the antigen are also provided. Such methods and uses encompass immunofluorescence, immunohistochemistry, flow cytometry (e.g., FACS), Western blotting, fluorescence ELISA, and any other approach where fluorescently labeled antibodies can be used.

Cytoskeletal staining. In some embodiments, SiR moieties of the present disclosure can be conjugated to a cytoskeleton binding moiety as described herein to provide compounds of Formula (I) comprising a cytoskeleton binding moiety. As such, methods for staining or detecting a cytoskeletal component (e.g., actin or microtubules) are provided, comprising contacting a cellular sample (e.g., comprising permeabilized and/or fixed cells) with a compound of Formula (I) comprising a cytoskeleton binding moiety (e.g., an actin- or microtubule-binding moiety, such as any of those described herein).

Nucleic acid staining and detection. In some embodiments, SiR moieties of the present disclosure can be conjugated to a nucleic acid binding moiety as described herein to provide compounds of Formula (I) comprising a nucleic acid binding moiety. In some embodiments, SiR moieties of the present disclosure can be attached to a polynucleotide, or to a nucleotide which is incorporated into a polynucleotide, which can then serve as a labeled primer or probe. Such compounds can be combined with a sample that contains or is thought to contain a nucleic acid polymer, and then the mixture of compound and sample is incubated for a time sufficient for the compound to combine with nucleic acid polymers in the sample to form one or more compound-nucleic acid complexes having a detectable fluorescent signal. The nucleic acid can be DNA, e.g., dsDNA or ssDNA. The nucleic acid can also be RNA or an RNA-DNA hybrid. The compounds can be used to label or detect nucleic acids in a wide variety of samples, such as in aqueous solutions, sequencing or amplification reactions such as PCR, cellular samples (e.g., for FISH or general nuclear or chromosome staining) and electrophoretic gels. Those skilled in the art will recognize when to use compounds comprising general nucleic acid- or DNA-binding moieties and when to use probes or primers that target specific sequences.

In some embodiments, methods of staining nucleic acids are provided, the methods comprising: combining a sample that contains or is thought to contain a nucleic acid with a compound of Formula (I); and incubating the sample and compound for a time sufficient for the compound to combine with the nucleic acid in the sample to form one or more compound-nucleic acid complexes that give a detectable fluorescent signal. In some embodiments, the compounds are selected from 1, 1A, 1B, 1C, 2, 2A, 3, 4A, 5, 6, 7, 7A, 7B, 8, 9, 10A, 10B, 11, 12, 13, 14, 15, 16, 17, 18, 19, 20, 21, 22, 23, 24, 25, 26, 27, 28, 29, 30, 31, 32, 33, 34, 35, 36, 37, 38, 39, 43, 45, 46, 47, 48, 49, 50, 51, 52, 53, 54, 55, 56, 57, 58, and 59, or an open or spirolactone form and/or salt or free acid thereof.

A target polynucleotide can be detected specifically, for example, using an SiR compound described herein which is capable of specifically binding the target polynucleotide, and determining whether a complex comprising the target polynucleotide and the SiR compound was formed, e.g., by detecting fluorescence from the complex or detecting a change in fluorescence resulting from complex formation, optionally wherein the change in fluorescence resulting from complex formation is a reduction of quenching by a quencher due to cleavage or a conformational change.

The characteristics of the SiR compound-nucleic acid complex, including the presence, location, intensity, excitation and emission spectra, fluorescence polarization, fluorescence lifetime, and other physical properties of the fluorescent signal can be used to detect, differentiate, sort, quantitate, and/or analyze aspects or portions of the sample. The compounds of the disclosure are optionally used in conjunction with one or more additional reagents (e.g., detectably different fluorescent reagents), including compounds of the same class having different spectral properties (see, e.g., discussion of shifts in emission and near-infrared dyes elsewhere herein).

Also provided are methods of sequencing a polynucleotide using SiR compounds disclosed herein. One skilled in the art will recognize the various ways fluorescent moieties can be employed in sequencing methods, for example, as labels on primers, chain-terminating nucleotides such as dideoxynucleotides, or reversible terminator nucleotides or dinucleotides (see, e.g., U.S. Pat. No. 8,017,338, PCT Pub. No. WO2008/037568, and U.S. Pat. No. 7,476,504 for general discussions of reversible terminator nucleotides and dinucleotides). Sequencing methods in which a sequencing reaction product is separated before detection, e.g., by electrophoresis such as capillary electrophoresis, may be used. Alternatively, sequencing methods in which products are detected in situ may be used (see, e.g., documents cited above).

Live/dead cell assays. Certain embodiments provide a method, use, or composition for staining cells and/or assessing cell viability, being compatible for use with, for example, flow cytometry and fluorescence microscopy. Such methods and uses can comprise incubating a cell or mixture of cells with an SiR compound disclosed herein; providing a stimulus to the cell or mixture of cells to elicit a fluorescent signal; and measuring the fluorescent signal. Methods and uses can further comprise quantifying the amount of live and/or dead cells, e.g., by determining whether the degree of fluorescence exceeds a predetermined threshold (indicating nonviability), or by grouping results into live and dead populations (where dead cell populations show a greater extent of staining given their compromised membrane integrity).

In some embodiments, the SiR compound of the present disclosure is delivered or passes into nonviable eukaryotic cells, e.g., mammalian cells, such as human cells. When the cells are illuminated with a light source, then fluorescence emissions can be collected, detected, analyzed, or measured. The cells in the assay may be treated with a substance or reagent that induces cell death, e.g., camptothecin or staurosporine. Data may be acquired using any appropriate fluorescence detection apparatus such as a plate reader, fluorescence microscope, or flow cytometer.

In some embodiments, the cell or mixture of cells are incubated with at least one, two, three, or four additional fluorescent molecules, wherein the at least one, two, three, or four additional fluorescent molecules are spectrally distinguishable from the compound according to the present disclosure, and fluorescent signals are measured measuring from the at least one, two, three, or four additional fluorescent molecules. Fluorescence from two sources is considered spectrally distinguishable if the emission maxima are separated by at least 30 nm or if fluorescence from the sources can be distinguished through the use of optical filters, e.g., a pair of filters wherein fluorescence from at least one of the molecules is differentially reduced by at least one of the filters.

In another embodiment, the assay method may be conducted where cells are contained in a plurality of vessels. In any vessel, the cells may be of one type or different types of cells. The cells may be the same type grown under different conditions, e.g. in the presence of different media. Some of the cells may be treated with an apoptosis inducer or a caspase inhibitor. The plurality of vessels, an array, may be illuminated by a light source, e.g. a scanning light source. The cells may be of the same or different organisms.

Super-resolution imaging and microscopy; single molecule localisation. In some embodiments, a compound described herein is used in super-resolution imaging or microscopy. For reviews of super-resolution imaging and microscopy, see Huang et al., Annu Rev Biochem. 2009; 78: 993-1016; Leung et al., Applied Spectroscopy 2011; 65: 967-980; and Schermelleh et al., J. Cell Biol. 2010; 190: 165-175. In some embodiments, a compound described herein is used in single molecule localization microscopy (e.g., in live cells). For detailed discussion of single molecule localization microscopy, see Patterson et al., Annu. Rev. Phys. Chem. 2010; 61: 345-367; Qu et al., Proc Natl Acad Sci USA 2004; 101: 11298-11303; and Shtengel et al., Proc Natl Acad Sci USA 2009; 106: 3125-3130. In any such method or use, a sample can be contacted with a compound described herein (e.g., which comprises a target-binding moiety) under conditions permissive for staining of the sample or a component of interest thereof with the compound. The stained sample can then be imaged according to a super-resolution or single molecule localization imaging or microscopy technique.

Staining Solution. In some embodiments, the SiR compound of the present disclosure is prepared for use by dissolving the SiR compound in a staining solution, e.g., an aqueous or aqueous-miscible solution that is compatible with the sample and the intended use. For biological samples, where minimal perturbation of cell morphology or physiology is desired, the staining solution is selected accordingly. For solution assays, the staining solution in some embodiments does not perturb the native conformation of the target material undergoing evaluation. High concentrations of organic solvents, cations, and oxidizing agents also generally reduce fluorescence, as does the ionic detergent sodium dodecyl sulfate (SDS) at concentrations ≥0.01%. A number of staining solution additives, however, do not interfere with the fluorescence of the compound-nucleic acid complex (e.g. urea up to 8M; CsCl up to 1 g/mL; formamide up to 50% of the solution; and sucrose up to 40%). The SiR compounds provided herein generally have greater stability in buffered solutions than in water alone; and agents that reduce the levels of free oxygen radicals, such as β-mercaptoethanol, contribute to the stability of the compounds.

A staining solution can be made by dissolving the SiR compound of the present disclosure directly in an aqueous solvent such as water, a buffer solution, such as buffered saline (in some embodiments non-phosphate for some viability discrimination applications), a Tris(hydroxymethyl)aminomethane (TRIS) buffer (e.g., containing EDTA), or a water-miscible organic solvent such as dimethylsulfoxide (DMSO), dimethylformamide (DMF), or a lower alcohol such as methanol or ethanol. The SiR compound can be preliminarily dissolved in an organic solvent (in some embodiments 100% DMSO) at a concentration of greater than or equal to about 100-times that used in the staining solution, then diluted one or more times with an aqueous solvent such as water or buffer, such that the SiR compound is present in an effective amount.

An effective amount of SiR compound of the present disclosure is the amount sufficient to give a detectable fluorescence response in combination with target material. The SiR compound concentration in the solution must be sufficient to contact the target material in the sample and to give a detectable signal, but too much compound may cause problems with background fluorescence. The optimal concentration and composition of the staining solution is determined by the nature of the sample (including physical, biological, biochemical and physiological properties), the nature of the SiR compound-sample interaction (including the transport rate of the compound to the site of the nucleic acids), and the nature of the analysis being performed, and can be determined according to standard procedures such as those described in examples below.

Sample Types. The SiR compound is combined with a sample that contains or is thought to contain a biological material of interest, e.g., cell (which may be of a specific type), antigen, cellular component, or nucleic acid.

The sample is optionally a biological structure (i.e. an organism or a discrete unit of an organism), or a solution (including solutions that contain biological structures), or a solid or semi-solid material. Consequently, the sample material used to practice the disclosure is optionally free in solution, immobilized in or on a solid or semi-solid material, extracted from a biological structure (e.g. from lysed cells, tissues, organisms or organelles), or remains enclosed within a biological structure. The target material can also be found in the cytosol of a cell, cytoplasm of a cell, or can be extracellular. In order for the target to bind to the SiR compounds, the target can be provided in an aqueous environment to contact the SiR compound, even if the nucleic acids are not enclosed in a biological structure.

The sample can be natural or synthetic and can be obtained from a wide variety of sources. The presence of the target material in the sample may be due to natural biological processes, or the result of a successful or unsuccessful synthesis or experimental methodology, undesirable contamination, or a disease state. The target material may be endogenous to the natural source or introduced as foreign material, such as by infection, transfection, or therapeutic treatment. Target material may be present in all, or only part, of a sample, and the presence of target material may be used to distinguish between individual samples, or to differentiate a portion or region within a single sample, or to identify the sample or characteristics of the sample.

In some embodiments, the sample containing target material is a cell or is an aqueous or aqueous-miscible solution that is obtained directly from a liquid source or as a wash from a solid material (organic or inorganic) or a growth medium in which cells have been introduced for culturing or a buffer solution in which target material has been placed for evaluation. Where the target material is in cells, the cells are optionally single cells, including microorganisms, or multiple cells associated with other cells in two or three dimensional layers, including multicellular organisms, embryos, tissues, biopsies, filaments, biofilms, etc. Alternatively, the sample is a solid, optionally a smear or scrape or a retentate removed from a liquid or vapor by filtration. In one aspect of the disclosure, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot. Industrial sources also include fermentation media, such as from a biological reactor or food fermentation process such as brewing or foodstuffs, such as meat, gain, produce, or dairy products.

Where the target material is present in a solution, the sample solution can vary from one of purified or synthetic target material to crude mixtures such as cell extracts or homogenates or other biological fluids, or dilute solutions from biological, industrial, or environmental sources. In some cases, it is desirable to separate the target material from a mixture of other biomolecules or fluids in the solution prior to combination with the compound. Numerous techniques exist for separation and purification of various target materials, such as nucleic acids, polypeptides, metabolites, oligo- and polysaccharides, lipids, and combinations thereof from generally crude mixtures with other biological molecules. These include such means as chromatographic techniques and electrophoretic techniques, using a variety of supports or solutions or in a flowing stream. Alternatively, mixtures of biomolecules may be treated with appropriate degradative enzymes (e.g., RNase, DNase, and/or protease) so that non-target material is degraded and can be more easily removed.

The source and type of sample, as well as the use of the SiR compound, will determine which compound characteristics, and thus which SiR compounds, will be most useful for staining a particular sample. Where the fluorescence of the compound is detected utilizing sustained high intensity illumination (e.g. microscopy), SiR compounds with rate of photobleaching lower than commonly used compounds (e.g. fluorescein) are preferred, particularly for use in live cells. The relatively low toxicity of the compounds to living systems generally enables the examination of nucleic acids in living samples with little or no perturbation caused by the compound itself. Where the compound must penetrate cell membranes or a gel, more permeant SiR compounds are preferred, although some cells readily take up compounds that are shown to be impermeant to other cells by means other than passive diffusion across cell-membranes, e.g. by phagocytosis or other types of ingestion. Compounds that rapidly and readily penetrate cells do not necessarily rapidly penetrate gels. In applications where the nucleic acids are stained on a gel, the SiR compound is also selected to have a high binding affinity (e.g., $K_d \geq 10^{-6}$ M); whereas in applications where the nucleic acid will be prestained prior to undergoing a separation step, such as gel or capillary electrophoresis, even higher binding affinity (e.g., $K_d \geq 10^{-8}$ M) is preferred to ensure good separation. In staining nucleic acids in solution, high binding affinity translates into greater sensitivity to small amounts of nucleic acid, but compounds with a moderate binding affinity (e.g., $10^{-6}$ M $\leq K_d \leq 10^{-8}$ M) are more effective over a greater dynamic range. The photostability, toxicity, binding affinity, quantum yield, and fluorescence enhancement of SiR compounds are determined according to standard methods known in the art.

Additional Reagents. The SiR compounds of the present disclosure can be used in conjunction with one or more additional reagents that are separately detectable. The additional reagents may be separately detectable if they are used separately, e.g. used to stain different aliquots of the same sample or if they stain different parts or components of a sample, regardless of whether the signal of the additional reagents is detectably different from the fluorescent signal of the compound-nucleic acid complex. Alternatively, the SiR compound of the disclosure is selected to give a detectable response that is different from that of other reagents desired to be used in combination with the SiR compounds. In some embodiments the additional reagent or reagents are fluorescent and have different spectral properties from those of the compound-nucleic acid complex. For example, SiR compounds described herein can be used in combination with commonly used fluorescent antibodies such as those labelled with fluorescein isothiocyanate or phycoerythrin. Any fluorescence detection system (including visual inspection) can be used to detect differences in spectral properties between compounds, with differing levels of sensitivity. Such differences include, but are not limited to, a difference in excitation maxima, a difference in emission maxima, a difference in fluorescence lifetimes, a difference in fluorescence emission intensity at the same excitation wavelength or at a different wavelength, a difference in absorptivity, a difference in fluorescence polarization, a difference in fluorescence enhancement in combination with target materials, or combinations thereof. The detectably different compound is optionally one of the SiR compounds of the disclosure having different spectral properties and different selectivity. In one aspect of the disclosure, the compound-nucleic acid complex and the additional detection reagents have the same or overlapping excitation spectra, but possess visibly different emission spectra, e.g., having emission maxima separated by ≥10 nm, ≥20 nm, or ≥50 nm. Simultaneous excitation of all fluorescent reagents may require excitation of the sample at a wavelength that is suboptimal for each reagent individually, but optimal for the combination of reagents. Alternatively, the additional reagent(s) can be simultaneously or sequentially excited at a wavelength that is different from that used to excite the subject compound-nucleic acid complex.

The additional compounds are optionally used to differentiate biological samples, e.g., containing cells or components thereof, according to size, shape, metabolic state, physiological condition, genotype, or other biological parameters or combinations thereof. The additional reagent is optionally selective for a particular characteristic of the sample for use in conjunction with a non-selective reagent for the same characteristic, or is selective for one characteristic of the sample for use in conjunction with a reagent that is selective for another characteristic of the sample. In one aspect of the disclosure, the additional compound or compounds are metabolized intracellularly to give a fluorescent product inside certain cells but not inside other cells, so that the fluorescence response of the cyanine compound of the disclosure predominates only where such metabolic process is not taking place. Alternatively, the additional compound or compounds are specific for some external component of the cell such as cell surface proteins or receptors, e.g. fluorescent lectins or antibodies. In yet another aspect of the disclosure, the additional compound or compounds actively or passively cross the cell membrane and are used to indicate the integrity or functioning of the cell membrane (e.g. calcein AM or BCECF AM). In another aspect, the additional reagents bind selectively to AT-rich nucleic acids and are used to indicate chromosome banding. In another aspect of the disclosure, the additional reagent is an organelle stain, i.e. a stain that is selective for a particular organelle, for example the additional reagent(s) may be selected for potential sensitive uptake into the mitochondria (e.g. rhodamine 123 or tetramethyl rosamine) or for uptake due to pH gradient in an organelle of a live cell (e.g. Diwu, et al., CYTOMETRY supp. 7, p 77, Abstract 426B (1994)).

The additional compounds are added to the sample being analyzed to be present in an effective amount, with the optimal concentration of compound determined by standard procedures generally known in the art. Each compound is optionally prepared in a separate solution or combined in one solution, depending on the intended use. After illumination of the dyed cells at a suitable wavelength, as above, the cells are analyzed according to their fluorescence response to the illumination. In addition, the differential fluorescence response can be used as a basis for sorting the cells or nucleic acids for further analysis or experimentation. For example, all cells that "survive" a certain procedure are sorted, or all cells of a certain type in a sample are sorted. The cells can be sorted manually or using an automated technique such as flow cytometry, according to the procedures known in the art, such as in U.S. Pat. No. 4,665,024 to Mansour, et al. (1987).

7. Kits

In another aspect, kits are provided comprising a SiR compound disclosed herein (which may be, but is not necessarily, a conjugate disclosed herein) and one or more other reagents. Any embodiment of a SiR compound described herein can be provided in a kit. In some embodiments, at least one additional reagent described above is included in a kit with a compound according to this disclosure. In certain embodiments, the kits further comprise one or more of the following: a buffering agent, a purification medium, or a vial comprising a sample. In some embodiments, a kit further comprises a cytotoxic agent, apoptosis inducer, cells, a solvent, or a desiccant. Kits may also include reagents useful to conduct the methods of the disclosure, e.g., conjugation methods, assay methods, or synthetic methods. As an example of the latter, a compound comprising a vinyl group can be provided with reagents for performing a thiol-ene reaction to derivatize the compound with a substituent; or a compound comprising a reactive ligand, such as an NHS ester or other reactive ligand described herein, can be provided with reagents for performing a nucleophilic substitution reaction to derivatize the compound with a substituent. In some embodiments, kits comprise at least one of an organic solvent and a desiccant. In some embodiments, the solvent is DMSO. In some embodiments, kits further comprise at least one additional substance such as a solvent, buffer, stabilizer, pH adjusting agent, etc. In some embodiments, the kit further comprises an antifade reagent.

The kit may also include eukaryotic cells. In some embodiments, the kit is compatible for use with flow cytometry. In some embodiments, the kit is compatible for use with fluorescence microscopy. In some embodiments, the kit comprises reagents for conjugating a compound to an antibody.

In some embodiments, the SiR compound in the kit is conjugated to an antibody, which can, e.g., be suitable for use as a secondary antibody (e.g., an antibody from a first species, such as rabbit or goat, specific for an antibody of a second species, such as human, mouse or rabbit, wherein the second species differs from the first species).

In some embodiments, the kit is compatible for use with a nucleic acid synthesis reaction, e.g., an amplification reaction such as PCR, qPCR, or rtPCR, or DNA sequencing. Such kits can comprise NTPs or dNTPs, a polymerase, and one or more primers. At least one of the NTPs/dNTPs or primers can be labeled with a compound disclosed herein, or the kit can further comprise a probe labeled with a compound disclosed herein. In some embodiments, such a labeled probe further comprises a quencher or energy transfer partner for the silicon-rhodamine moiety, e.g., which can render the probe suitable for use in assays involving degradation, cleavage, or conformational changes of a probe that change (e.g., increase) fluorescence by the SiR moiety, such as TaqMan assays or assays using molecular beacon probes.

In certain embodiments, the kits disclosed herein comprise one or more of the compounds described herein and one or more containers in which to store the one or more compounds. The kit optionally contains instructions for how to prepare the one or more compounds or how to prepare a composition containing the one or more SiR compounds, and how to administer the compound or composition containing the compound. In certain embodiments, the kit comprises instructions for performing a method disclosed herein. In certain embodiments, the method is an in vitro method. The kit may further comprise one or more pieces of equipment to deliver the SiR compound, or composition containing the compound including, but not limited to, syringes, pipettes, pipette bulbs, spatulas, vials, syringe needles, and various combinations thereof.

8. Preparative Methods for SiR Compounds and Related Intermediates

Methods of preparing compounds of formula (I), including Compounds 1, 1A, 1B, 1C, 2, 2A, 3, 4A, 5, 6, 7, 7A, 7B, 8, 9, 10A, 10B, 11, 12, 13, 14, 15, 16, 17, 18, 19, 20, 21, 22, 23, 24, 25, 26, 27, 28, 29, 30, 31, 32, 33, 34, 35, 36, 37, 38, 39, 43, 45, 46, 47, 48, 49, 50, 51, 52, 53, 54, 55, 56, 57, 58, and 59 described herein, are provided. Also provided are methods of preparing synthetic intermediates useful for preparing compounds of formula (I).

Many functionalized SiR dyes have been synthesized by modifying the xanthene moiety for different biological applications, especially for super-resolution imaging and intracellular targeting. However, modification of the xanthene moiety usually results in significant changes in the photophysical properties of the dye, such as absorption and emission wavelengths, quantum yield and photostability. For this reason, a new synthetic strategy is provided herein to introduce functional or reactive group (s) to the SiR dye compounds at position 10 silicon. Specifically, one or more vinyl groups are introduced at the 10 position to form mono-vinyl and bis-vinyl SiR dyes, which can be further derivatized by thiol-ene reaction to introduce functional or reactive group(s). In the synthetic method provided herein, no Si-xanthone intermediate is involved (see FIGS. 2B and 2E).

Furthermore, most of the current synthetic procedures to make SiR derivatives use extremely hazardous reagents (for example tert-butyllitumn, sec-butyllithium, thionyl chloride, and 6 N HCl) as well as require long and laborious synthetic steps. In contrast, the synthetic approach provided herein needs only two steps to make the key SiR core structure, followed by a final thiol-ene reaction that provides a linker, herein termed an "EthylSulfurPropionic acid linker" or "ESP linker", which can be coupled with various ligands for target organelles (See, FIGS. 2B-2E). SiR compounds of the present disclosure that comprise this ESP linker have unexpected properties, including increased brightness and photostability.

Moreover, a thiol-ene reaction with the methylvinyl-SiR (Compound 1) can provide linkers of different lengths ranging from 4 to 12 atoms. The proximity of the fluorophore to target ligands is important in designing SiR live cell fluorescent probes Formulae P1a, P1b, P2, and P2a, representing useful precursors or synthetic intermediates for preparing compounds of Formula (I), are shown below. Exemplary compounds and steps according to this route are shown in FIGS. 2B-E.

Briefly, in a first synthetic route, described from end to beginning, a compound of Formula (I) can be prepared from a compound of Formula (P2) and a compound of Formula (P2a). A compound of Formula (P2a) can be prepared by known methods. A compound of Formula (P2) can be prepared from compounds of Formulae (P1a) and (P1b) (which may be the same or different) and $SiCl_2R^1R^2$. All of compounds of Formulae (P1a) and (P1b) and $SiCl_2R^1R^2$ can be prepared by known methods.

In some embodiments, a method of preparing a compound of Formula (I) is provided, comprising reacting a compound of Formula (P2)

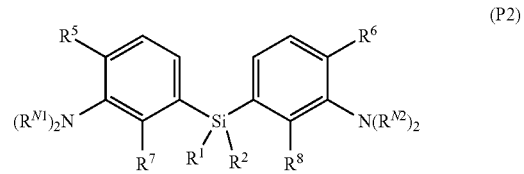

with a compound of Formula (P2a)

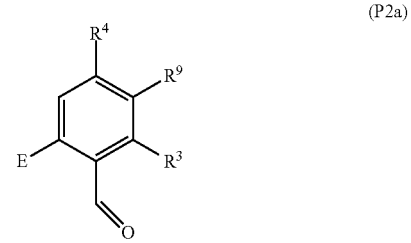

in the presence of $CuBr_2$ at a temperature above 100° C., wherein $R^1$, $R^2$, $R^3$, $R^4$, E, $R^5$, $R^6$, $R^7$, $R^8$, $R^9$, $R^{N1}$, and $R^{N2}$ have values described herein, thereby producing a compound of Formula (I).

In some embodiments, a method is provided of preparing a compound of Formula (P2):

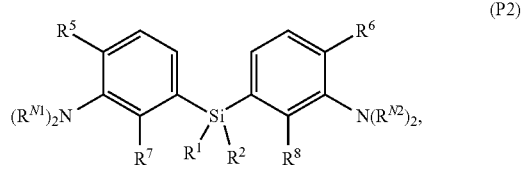

the method comprising reacting compounds of Formula (P1a)

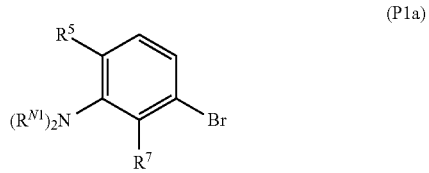

and Formula (P1b)

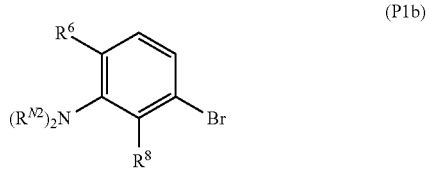

with an organolithium base, such as butyllithium, and then with $SiCl_2R^1R^2$, wherein $R^1$, $R^2$, $R^5$, $R^6$, $R^7$, $R^B$, $R^{N1}$, and $R^{N2}$ have values described herein. A method using a compound of Formula (P2) may also comprise preparing the compound of Formula (P2) as set forth above.

Synthetic routes for certain compounds of Formula (I) further comprise additional steps, e.g., where desired substituents are less compatible with steps leading to an initial compound of Formula (I).

For example, $R^1$ and/or $R^2$ can be a vinyl in the initial compound of Formula (I) and can then be derivatized through a thiol-ene reaction and optionally additional steps to provide other values of $R^1$ and/or $R^2$ described herein. A thiol-ene reaction can comprise reacting a thiol, e.g., HS-linker-Z, where Z is a reactive group, e.g., a reactive group described herein such as a carboxyl or amine, with a compound of Formula (I) where $R^1$ and/or $R^2$ is vinyl to provide a compound of Formula (I) in which $R^1$ and/or $R^2$ is linked to reactive group Z. Z can be used to further derivatize the compound, e.g., to provide a conjugate to a target-binding moiety, e.g., a target-binding moiety described herein such as a nucleic acid binding moiety, a cytoskeleton-binding moiety, etc. See, e.g., Compounds 4-6, among others.

Alternatively or in addition, $R^3$ or $R^4$ can be a carboxyl in the initial compound of Formula (I) and then can be further derivatized, e.g., to provide a linker and a reactive ligand or target-binding moiety. For example, the carboxyl can be converted to an acyl chloride with $POCl_3$ and then further substituted using known chemistry (e.g., comprising nucleophilic substitution of the chloride) to arrive at compounds such as Compounds 7 and 7B (see FIG. 2E).

Additional details and optional steps useful for providing various compounds of Formula (I) are described elsewhere herein, e.g., in the figures, the Examples, and in the description of conjugates, reactive ligands, phosphoramidites, nucleotides and nucleosides, and moieties to increase solubility above.

EXAMPLES

The following examples are provided to illustrate certain disclosed embodiments and are not to be construed as limiting the scope of this disclosure in any way.

Example 1. Preparation of Compounds

Synthesis of 3,3'-(methyl(vinyl)silanediyl)bis(N,N-dimethylaniline)

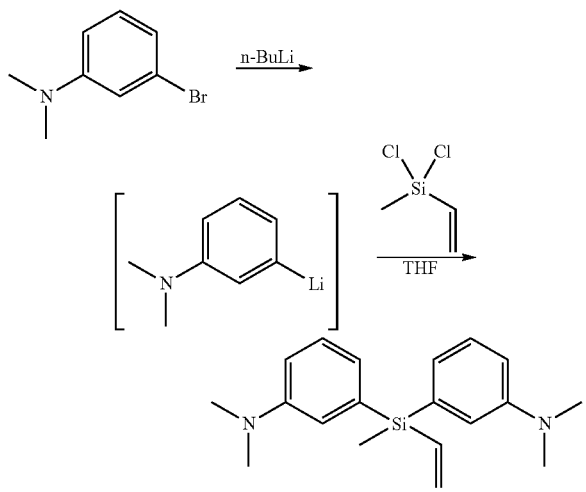

To a well-dried 1 L three-neck round bottom flask was added 3-bromo-NNJ-dimethylaniline (25 g, 125.0 mmol). THF (300 mL) was transferred to the flask. The reaction mixture was cooled to −78° C., and maintain the temperature for 30 min. n-BuLi (59.8 mL of 2.3 M n-BuLi in hexanes, 137 mmol) was added into an additional funnel, and added to the reaction mixture dropwise over 45 min. After stirring for 1 h at the same temperature, methylvinyldichlorosilane (10.61 mL, 81.2 mmol) was added to the reaction mixture at −78° C. Dry ice bath was removed to increase temperature to room temperature (RT), and further stirring for 90 min at RT. The reaction mixture was quenched with water, and removed most of THF using a rotavapor. The crude was diluted with EtOAc (150 mL), and the aqueous layer further extracted with EtOAc (2×150 mL). The combined organic layer was washed with brine, dried over $Na_2SO_4$, filtered, and concentrated. The crude was purified by column chromatography on silica gel (Hex:EtOAc=9:1) to give 3,3'-(methyl(vinyl)silanediyl)bis(N,N-dimethylaniline) (12.6 g, 65%).

Synthesis of Compound 1

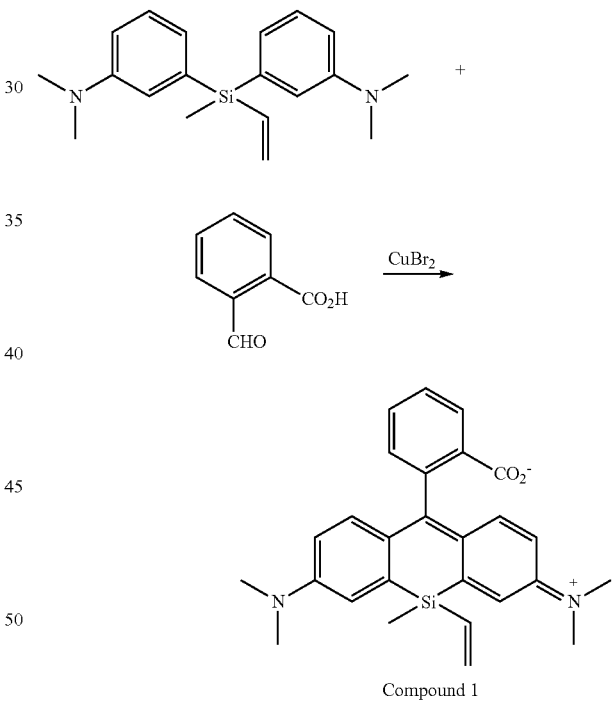

Compound 1

To a 75 mL pressure vessel were added 3,3'-(methyl(vinyl)silanediyl)bis(N,N-dimethylaniline) (3.8 g, 12.24 mmol), 2-carboxybenzaldehyde (3.67 g, 24.48 mmol), and $CuBr_2$ (273 mg, 1.22 mmol). The reaction mixture was stirred for 3 h at 120° C. After cooling down to RT, the deep blue crude was diluted in $CHCl_3$ (150 mL) and water (150 mL). The aqueous layer was further extracted with $CHCl_3$ (100 mL×2) and the combined organic layer was transferred to a separatory funnel. The organic layer, dried over $Na_2SO_4$, filtered, and concentrated using a rotavapor. The crude was purified by column chromatography on silica gel (Hex:EtOAc=9:1) to give Compound 1 (890 mg, 17%).

Synthesis of Compound 2

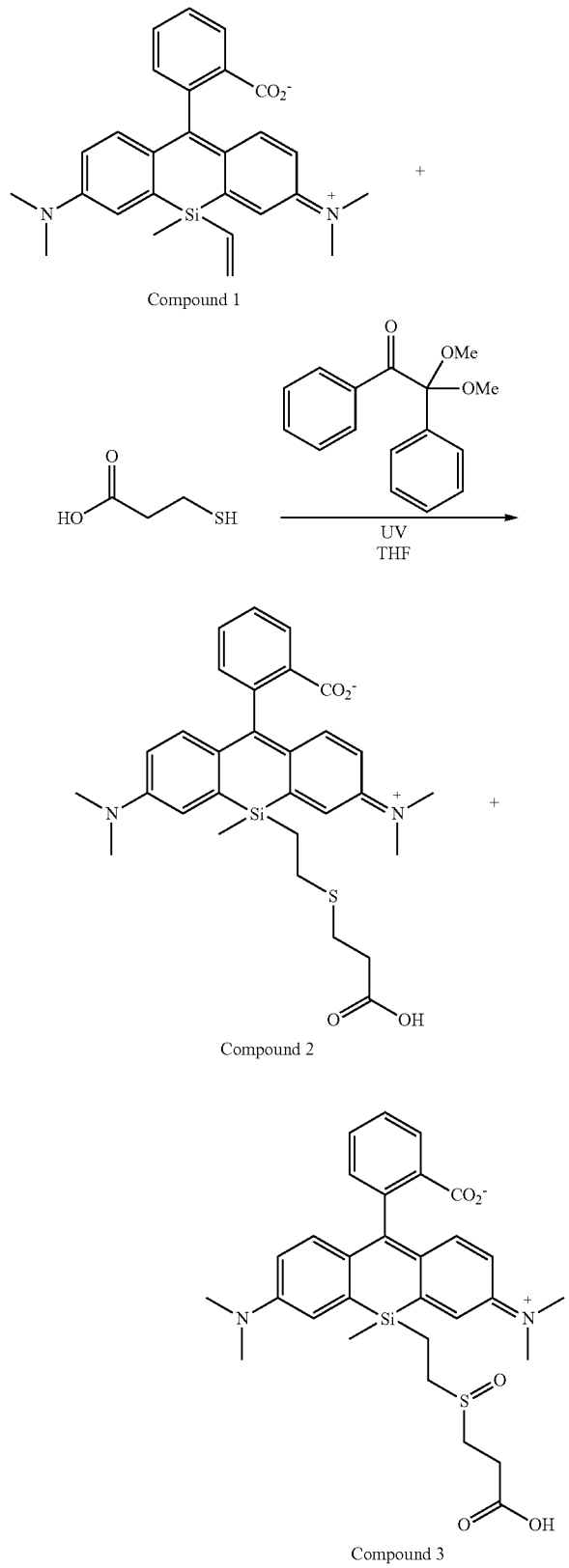

To a 250 mL quartz flask containing Compound 1 (400 mg, 0.91 mmol) were added 3-mercaptopropionic acid (154 mg, 1.45 mmol), DMPA (58 mg, 0.23 mmol), and THF (20 mL). The flask was connected with an argon balloon. The reaction was illuminated with long wavelength UV light for 2 h at RT. The photolysis reaction mixture was concentrated using a rotavapor. The crude was purified by column chromatography on silica gel ($CHCl_3$:MeOH=9:1) to give Compound 2 (350 mg, 71%) and Compound 3 (46 mg, 9%).

Synthesis of Compound 2A

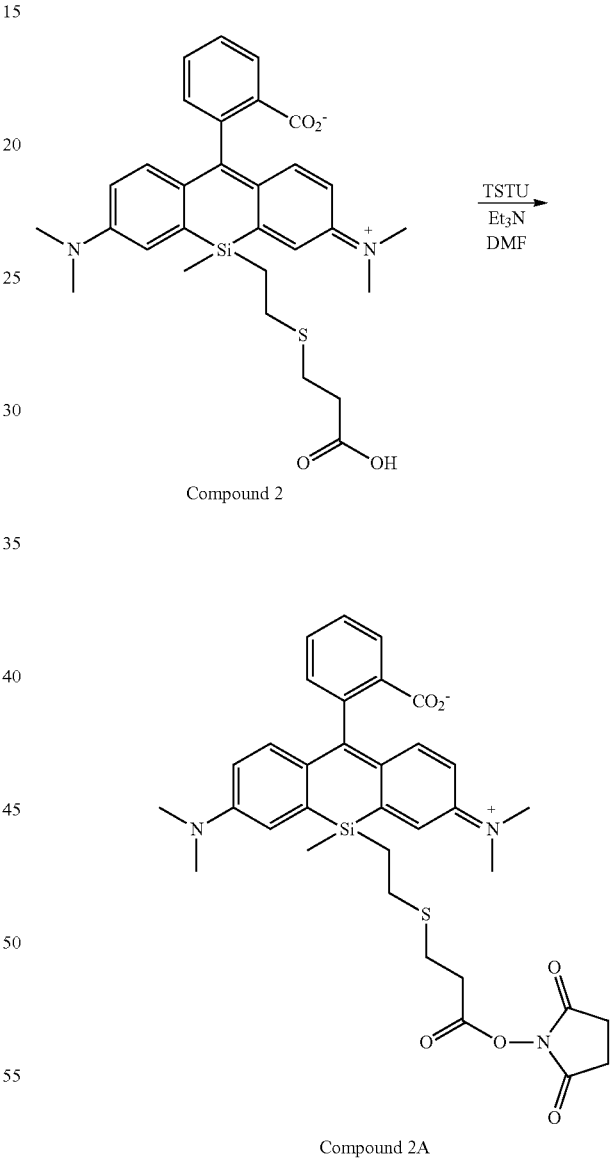

To a flask containing Compound 2 (330 mg, 0.6 mmol) were added DMF (10 mL), triethylamine (252 μL, 1.81 mmol), and TSTU (363 mg, 1.21 mmol). The reaction mixture was stirred for 1.5 h at RT. Solvent was removed using a high vacuum pump via rotary evaporation. The crude was purified by column chromatography on silica gel ($CHCl_3$:MeOH=9:1) to give Compound 2A (243 mg, 62%).

Synthesis of Compound 4

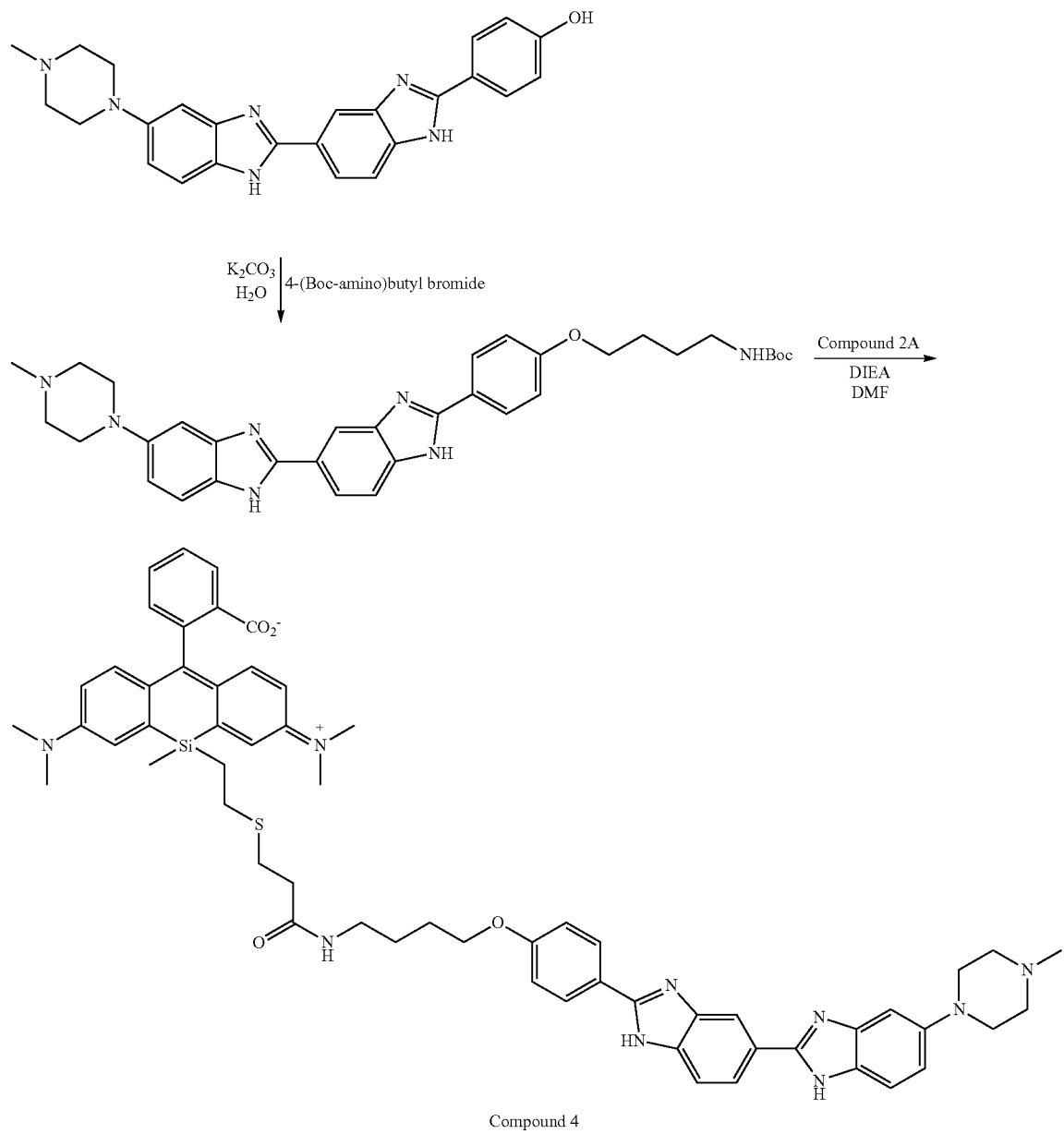

Compound 4

To a solution of 2'-(4-hydroxyphenyl)-5-(4-methyl-1-piperazinyl)-2,5'-bi(1H-benzimidazole) (28 mg, 66.0 µmol) in DMF (2 mL) were added $K_2CO_3$ (25 mg, 0.18 mmol) and 4-(Boc-amino)butyl bromide (21.6 mg, 85.7 mmol), and the reaction mixture was heated at 60° C. for 24 h. The solvent was removed using a high vacuum pump via rotary evaporation. The crude was purified by column chromatography on silica gel ($CHCl_3$:MeOH=3:1) to give an intermediate (15 mg, 38%).

20% TFA in DCM (1.0 mL) was added to the intermediate (14 mg, 23.5 µmol), and stirred for 15 min at RT. The solvent was removed using a rotavapor to give the Boc-deprotected intermediate. To a solution of Compound 2A (12 mg, 18.6 µmol) in DMF (2.0 mL) were added DIEA (12 mg, 93.2 µmol) and the Boc-deprotected intermediate in DMF (1.0 mL), and the reaction was stirred for 2 h at RT. Solvent was removed using a high vacuum pump via rotary evaporation. The crude was purified by Biotage on C-18 column (MeOH/$H_2O$, 0% to 95% gradient) to give Compound 4 (10.5 mg, 44%).

Compound 4 can exist as a mixture of two diastereomers due to the stereo center on the silicon atom and spirolactonization. During the Biotage C-18 purification, two diastereomers (Compound 4B and Compound 4C) were isolated. One diastereomer ran slower on TLC than Compound 4C, so this diastereomer is referred to in the figures as "bottom", and Compound 4C is referred to as "top". However, Applicant notes that this designation is arbitrary as the configuration of the two diastereomers has yet been assigned.

Synthesis of Compound 5

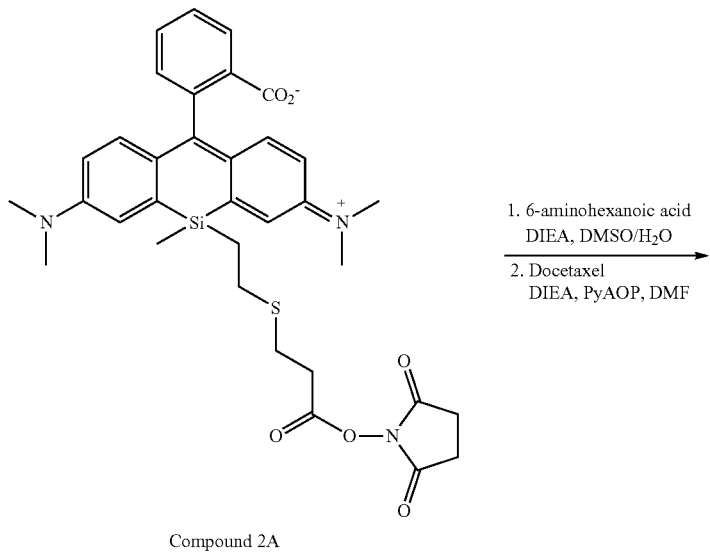

Compound 2A

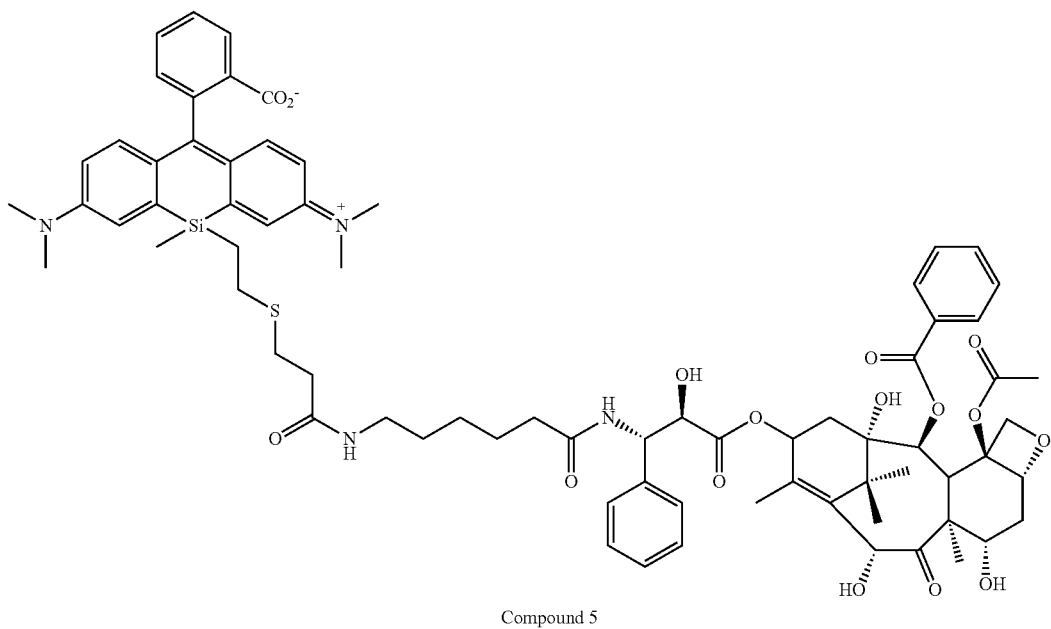

Compound 5

To a solution of Compound 2A (200 mg, 0.31 mmol) in DMSO (8 mL) was added a solution of 6-aminohexanoic acid (61 mg, 0.47 mmol) and DIEA (120 mg, 0.93 mmol) in DMSO/H2O (1:1.8 mL), and stirred for 2 h at RT. The crude was purified by Biotage on C-18 column (MeOH/H$_2$O, 0% to 95% gradient) to give an intermediate (80 mg).

Docetaxel (117 mg, 0.15 mmol) was dissolved in formic acid (3.0 mL), stirred for 20 min, and the solvent was removed to afford 3'-aminodocetaxel. To a solution of the intermediate (80 mg, 0.12 mmol), DIEA (73 mg, 0.61 mmol), and PyAOP (95 mg, 0.18 mmol) in DMF (4 mL) was added the above 3'-aminodocetaxel in DMF (2 mL). Solvent was removed using a high vacuum pump via rotary evaporation. The crude was purified by column chromatography on silica gel (CHCl$_3$:MeOH=9:1) to give Compound 5 (65 mg, 15%).

Each diastereomer of Compound 5 was isolated during the final column chromatography purification. Compound 5B ran slower on TLC than Compound 5C, so this diastereomer is referred to in the figures as "bottom", and Compound 5C is referred to as "top". However, correct configuration of two diastereomers have not assigned yet.

Synthesis of Compound 6
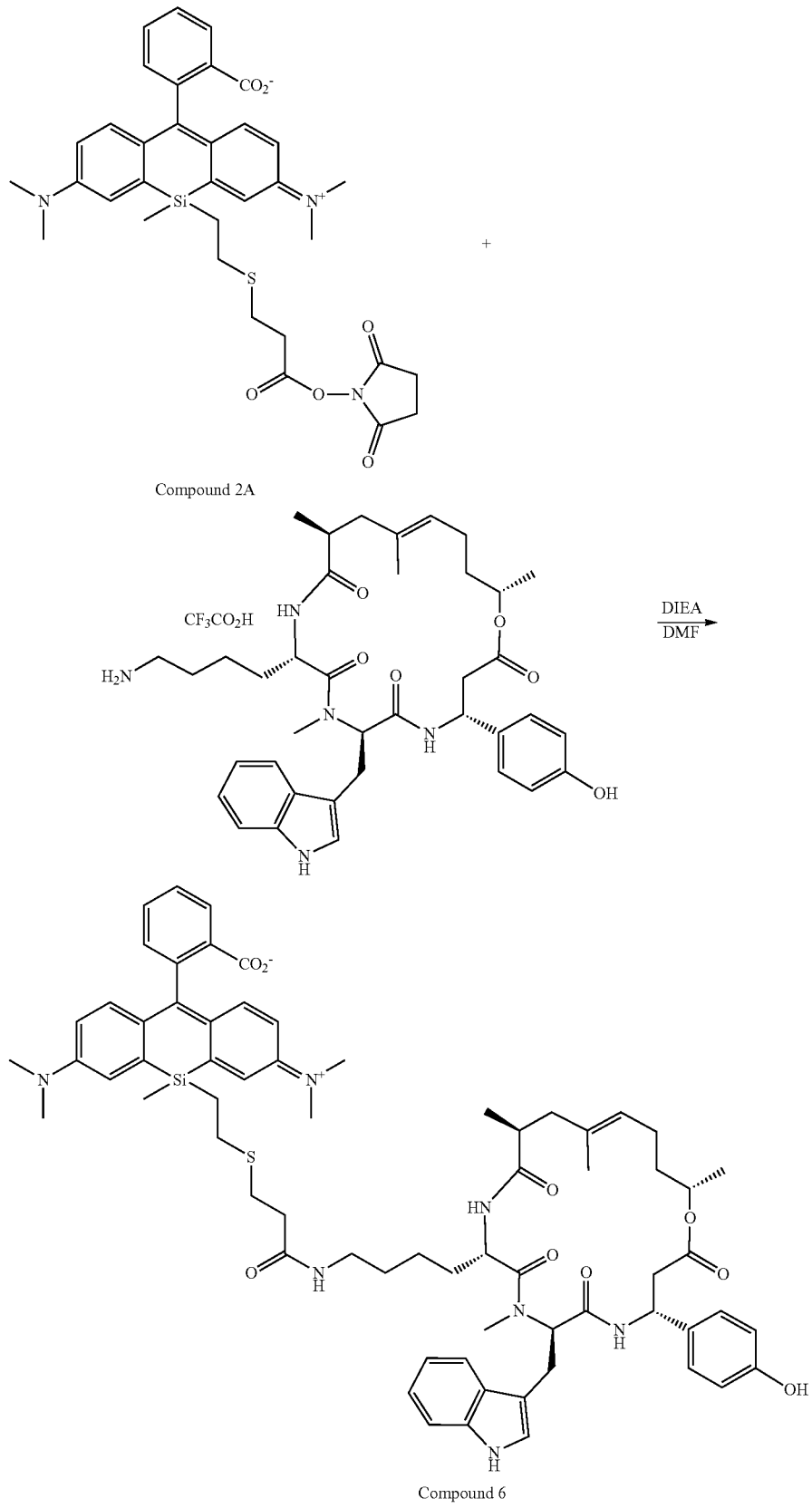

(4R,7R,10S,13S,E)-7-((1H-indol-3-yl)methyl)-10-(4-aminobutyl)-4-(4-hydroxyphenyl)-8,13,15,19-tetramethyl-1-oxa-5,8,11-triazacyclononadec-15-ene-2,6,9,12-tetraone 2,2,2-trifluoroacetate[1] (2.0 mg, 2.5 μmol) was dissolved in 0.3 mL of dry DMF, containing N,N-diisopropyl-N-ethyl-amine (3.3 mg, 0.025 mmol). Compound 2A (2.5 mg, 3.8 μmol) was dissolved in 0.1 mL of chloroform and added to a solution of peptide. The solution was kept at RT for 1 hr, then evaporated to dryness. The residue was purified on analytical aluminum backed TLC plate using $CHCl_3$/MeOH (10:1) mixture. The bend of the product was cut off from TLC plate and extracted multiple times with CHCl3-MeOH mixture. The combined extract was filtered and the solvent was evaporated to give Compound 6 (2.0 mg, 66%).

Milroy, Lech-Gustav et al., "Selective Chemical Imaging of Static Actin in Live Cells" J. Am. Chem. Soc., vol. 134, Apr. 4, 2012, pp 8480-8486.

Compound 6A was synthesized according to the reaction scheme shown below.

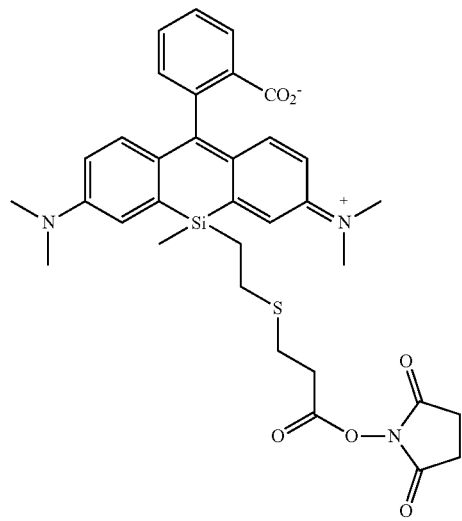

Compound 2A

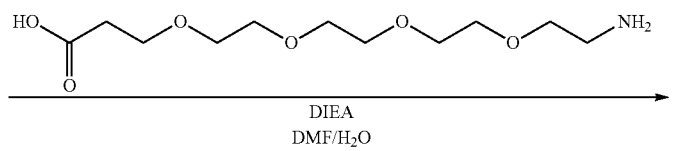

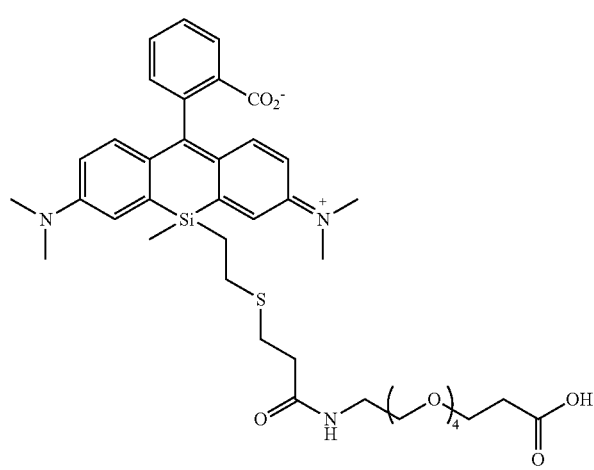

Intermediate

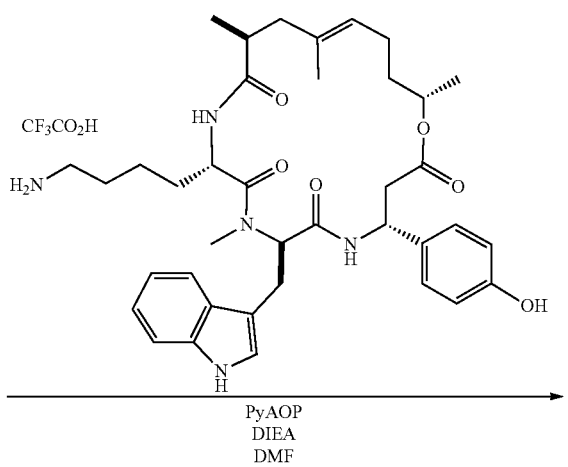

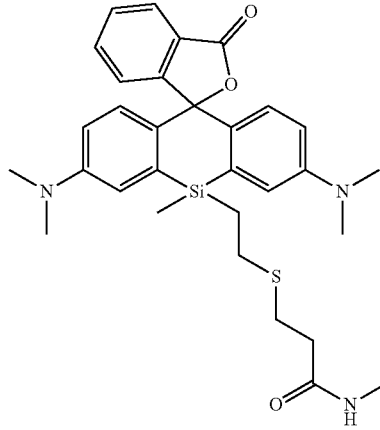
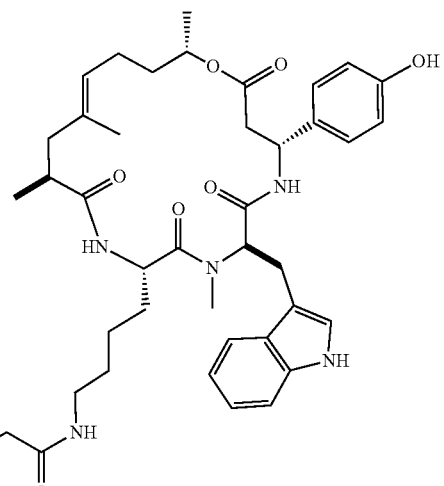

Compound 6A

Synthesis of Compound 6A

To a solution of 2A (100 mg, 0.155 mmol) in DMF (1.5 mL) were added a solution of amino-PEG$_4$ acid (43 mg, 0.17 mmol) in DI-water (0.5 mL), and DIEA (60 mg, 0.47 mmol). The reaction mixture was stirred for 30 min, and removed the solvent. The crude was purified by Biotage on C-18 column (MeOH/H$_2$O, 0% to 80% gradient) to give an intermediate (50 mg, 40%).

To a solution of the intermediate (61 mg, 76.20 µmol), DIEA (41 mg, 0.32 mmol), and PyAOP (50 mg, 0.095 mmol) in DMF (2 mL) was added the (4R,7R,10S,13S,19S,E)-7-((1H-indol-3-yl)methyl)-10-(4-aminobutyl)-4-(4-hydroxyphenyl)-8,13,15,19-tetramethyl-1-oxa-5,8,11-triazacyclononadec-15-ene-2,6,9,12-tetraone 2,2,2-trifluoroacetate (50 mg, 63.5 µmol). The reaction mixture was stirred for 30 min at RT, and solvent was removed using a high vacuum pump via rotary evaporation. The crude was purified by Biotage on C-18 column (MeOH/H$_2$O, 0% to 90% gradient) to give Compound 6A (51 mg, 55%).

Each diastereomer of Compound 6A was isolated during the final column chromatography purification. Compound 6A-A ran slower on TLC than Compound 6A-B, so this diastereomer is referred to in the figures as "ESP-PEG4-A", and Compound 6A-B is referred to as "ESP-PEG4-B". However, correct configuration of the two diastereomers has not yet been assigned. Compound 6B containing a PEG$_{12}$ linker was prepared according to the above procedure.

Synthesis of Compound 6B

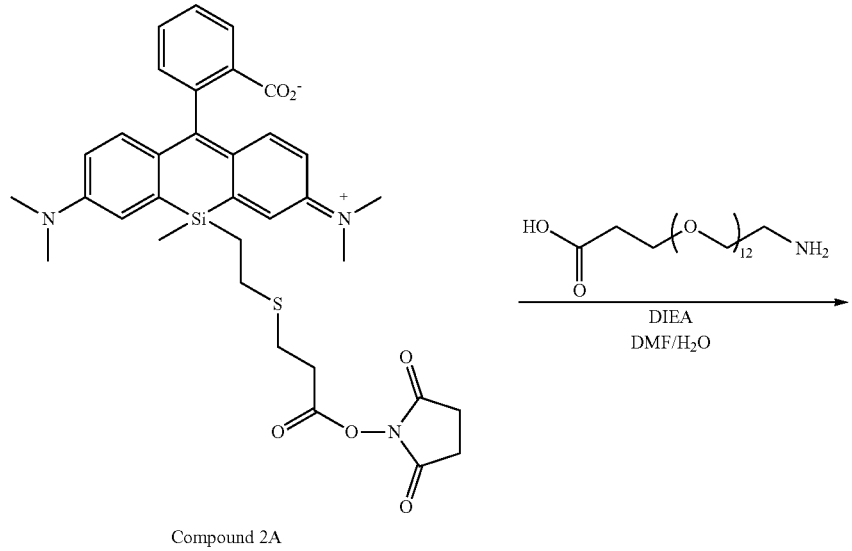

Compound 2A

77
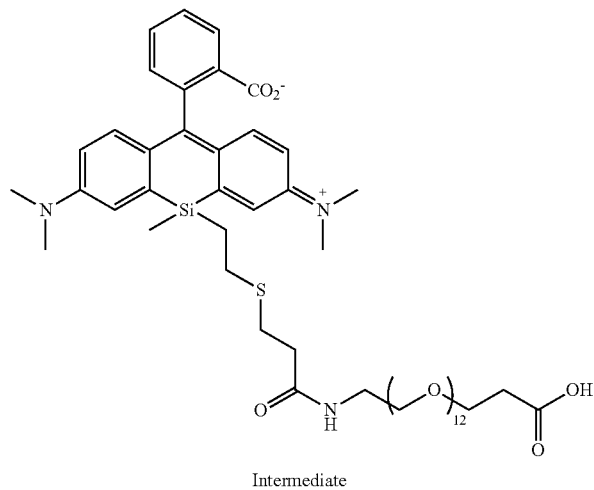
Intermediate
-continued
78
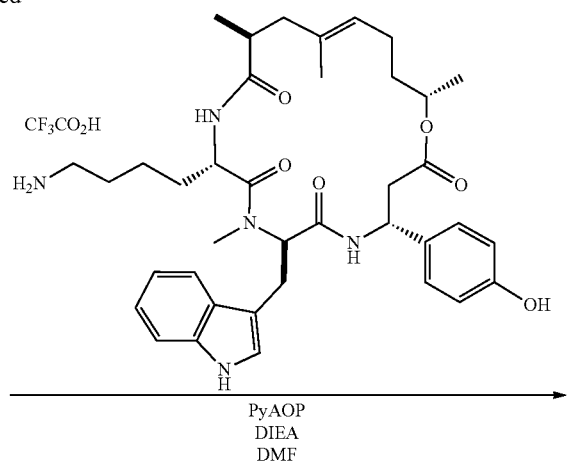
$\xrightarrow{\text{PyAOP, DIEA, DMF}}$
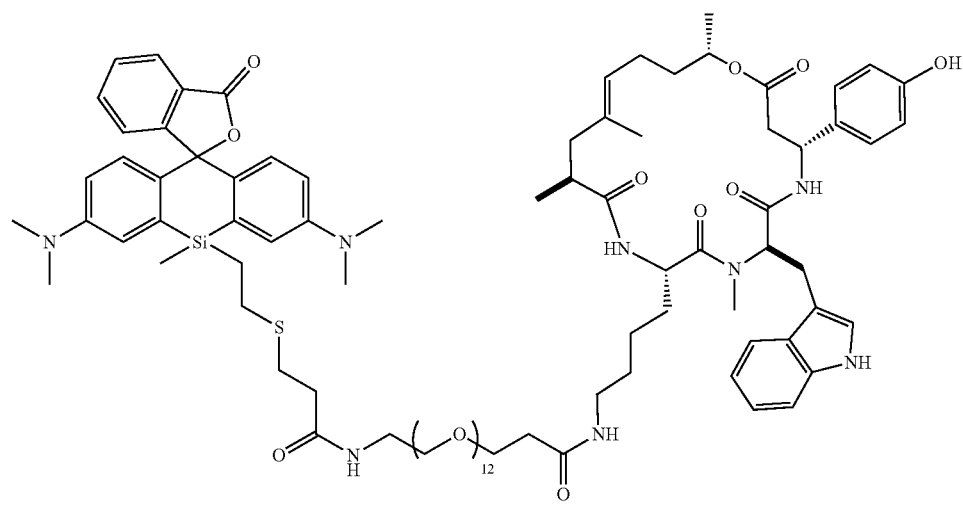
Compound 6B The synthesis of Compound 6C is shown below.
Synthesis of Compound 6C
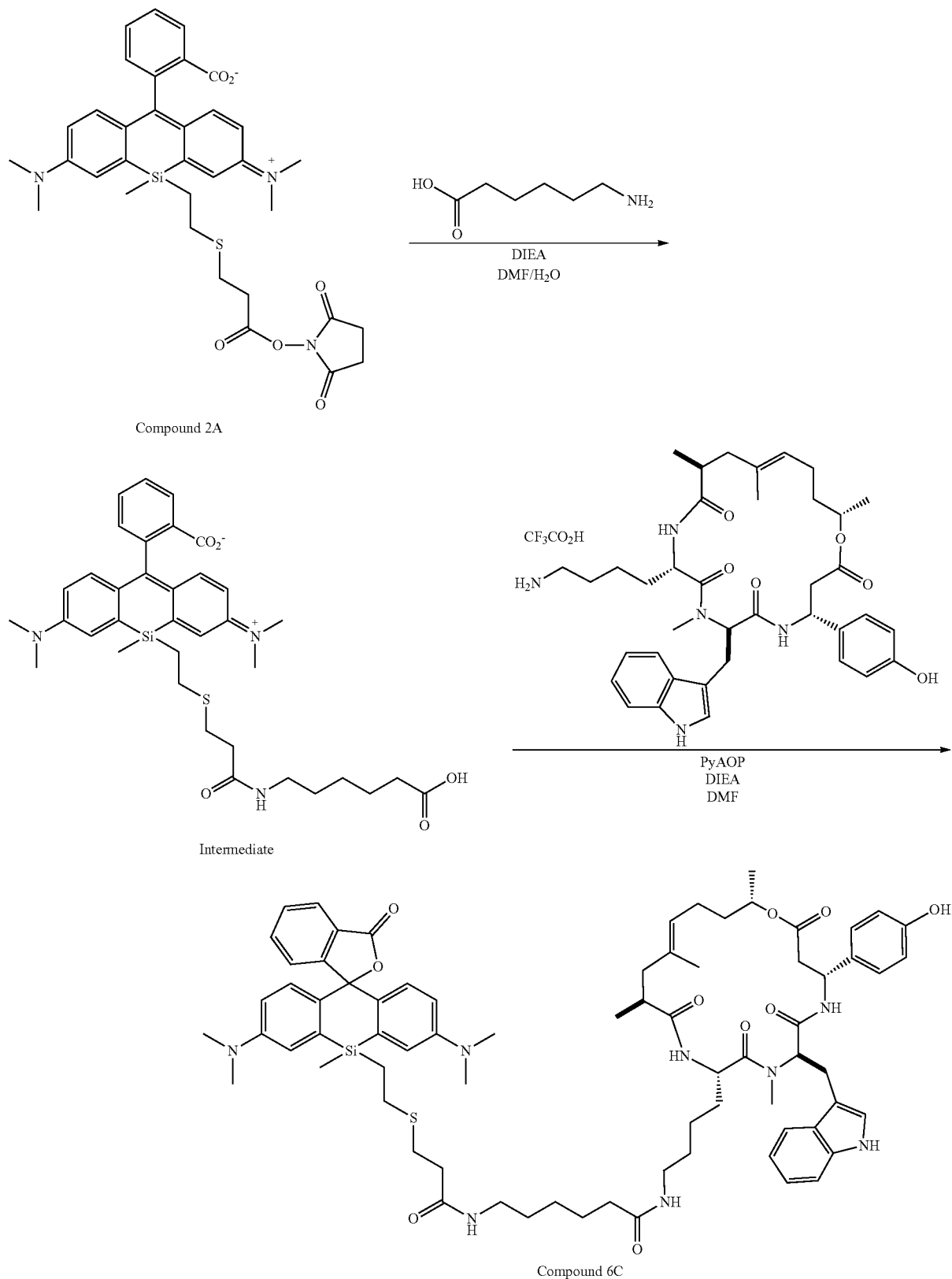

Compound 6C containing a C6 linker was prepared according to the procedure to make Compound 6 described above.

Synthesis of 3,3'-(dimethylsilanediyl)bis(N,N-dimethylaniline)

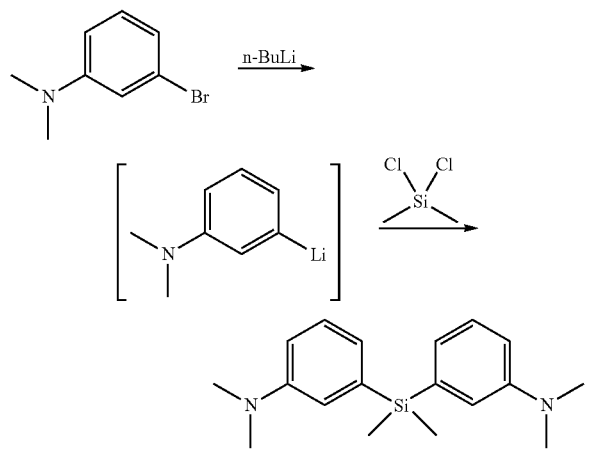

To a well-dried 500 mL three-neck round bottom flask were added 3-bromo-N,N-dimethylaniline (6.01 g, 30.0 mmol), and THF (60 mL). The reaction mixture was cooled to −78° C., and maintain the temperature for 30 min. n-BuLi (12.0 mL of 2.5 M n-BuLi in hexanes, 30.0 mmol) was added to the reaction mixture dropwise using a syringe over 5 min at −78° C. After stirring for 30 min at the same temperature dimethyldichlorosilane (1.51 mL, 12.5 mmol) was added to the reaction mixture at −78° C. The dry ice bath was removed to increase the temperature to RT, and further stirring for 90 min at RT. The reaction mixture was quenched with saturated $NH_4Cl$ solution, and diluted with DI-water (60 mL). The aqueous layer was extracted with EtOAc (3×60 mL). The combined organic layer was washed with brine (100 mL), dried over $Na_2SO_4$, filtered, and concentrated. The crude was purified by column chromatography on silica gel (Hex:EtOAc=9:1) to give 3,3'-(dimethylsilanediyl)bis(N,N-dimethylaniline) (2.92 g, 65%).

Synthesis of 2-(7-(dimethylamino)-3-(dimethyliminio)-5,5-dimethyl-3,5-dihydrodibenzo[b,e]silin-10-yl)benzoate

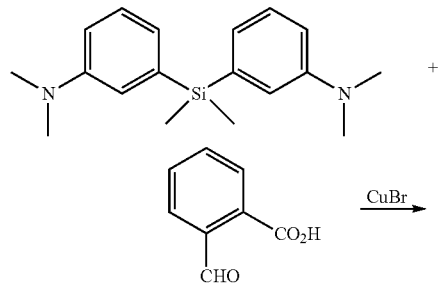

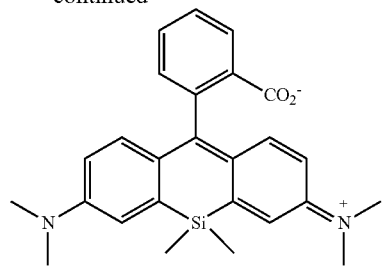

To a 75 mL pressure vessel were added 3,3'-(methyl(vinyl)silanediyl)bis(N,N-dimethylaniline) (2.8 g, 9.38 mmol), 2-carboxybenzaldehyde (4.23 g, 28.14 mmol), and $CuBr_2$ (210 mg, 0.94 mmol). The reaction mixture was stirred for 3 h at 120° C. After cooling down to RT, the deep blue crude was dissolved in $CHCl_3$ (100 mL), and washed with 2 N NaOH (120 mL). The aqueous layer was further extracted with $CHCl_3$ (60 mL×2), the combined organic layer was transferred to a separatory funnel. The organic layer was dried over $Na_2SO_4$, filtered, and concentrated using a rotavapor. The crude was purified by column chromatography on silica gel (Hex:EtOAc=9:1) to give 2-(7-(dimethylamino)-3-(dimethyliminio)-5,5-dimethyl-3,5-dihydrodibenzo[b,e]silin-10-yl)benzoate (828 mg, 21%).

Synthesis of Compound 7A

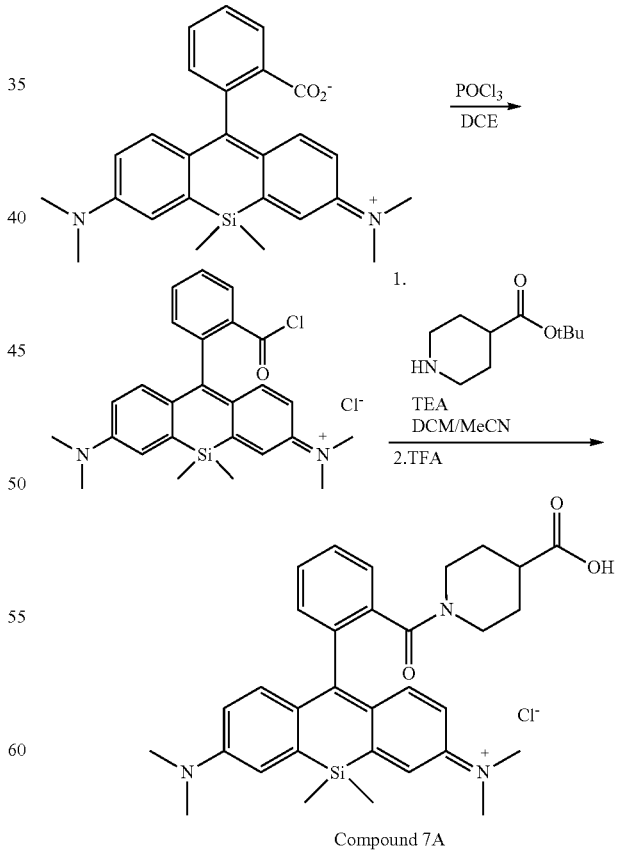

Compound 7A

To a solution of 2-(7-(dimethylamino)-3-(dimethyliminio)-5,5-dimethyl-3,5-dihydrodibenzo[b,e]silin-10-yl)benzoate (300 mg, 0.70 mmol) in 1,2-dichloroethane (4 mL) was added POCl₃ (1.96 mL, 21.0 mmol). The reaction mixture was stirred for 4 h. The volatile material was removed on rotary evaporator under house vacuum to give the acylated crude.

tert-Butyl piperidine-4-carboxylate hydrochloride (186 mg, 0.84 mmol) and DCM/MeCN (1:1.14 mL) were added to the flask containing the above acylated crude. To this solution was added triethylamine (1.95 mL, 14.0 mmol) at 0° C., and further stirred for 15 h at RT. Solvent was removed using a rotavapor. The crude was purified by Biotage on C-18 column (Di-water (0.1% TFA)/acetonitrile (0.1% TFA), 0 to 95% gradient) to give the ester compound (287 mg).

50% TFA in DCM was added to the ester compound, and stirred for 2 h. The volatile material was removed by a rotavapor, and the crude was purified by Biotage on C-18 column (Di-water (0.1% TFA)/acetonitrile (0.1% TFA), 0 to 95% gradient) to give Compound 7A (188 mg, 41% over 3 steps).

Synthesis of Compound 7B

Intermediate 1 (20 mg, 42.6 µmol), 4-(Boc-amino)butyl bromide (14 mg, 55.4 µmol), and K₂CO₃ (15.9 mg, 0.12 mmol) was dissolved in DMF (1 mL). The reaction mixture was stirred for 5 h. Solvent was removed using a high vacuum pump via rotary evaporation. The crude was purified by column chromatography on silica gel (CHCl₃:MeOH=4:1) to give Intermediate 2 (8 mg, 29%).

A solution of Intermediate 2 (4.4 mg, 6.87 µmol) in 30% TFA in DCM (1 mL) stirred for 10 min. The solvent was removed using a rotavapor. To a solution of the Compound 7A (5.0 mg, 8.7 µmol) in DMF (1.0 mL) were added PyAOP (5.4 mg, 10.3 µmol) and DIEA (4.4 mg, 34.3 µmol). After 5 min stirring at RT, deprotected intermediate in DMF (1.0 mL) added to the above solution. The reaction mixture was stirred for 2 h at RT. Solvent was removed using a high vacuum pump via rotary evaporation. The crude was purified by Biotage on C-18 column (Di-water (0.1% TFA)/acetonitrile (0.1% TFA), 0 to 95% gradient) to give Compound 7B (5.5 mg, 53%).

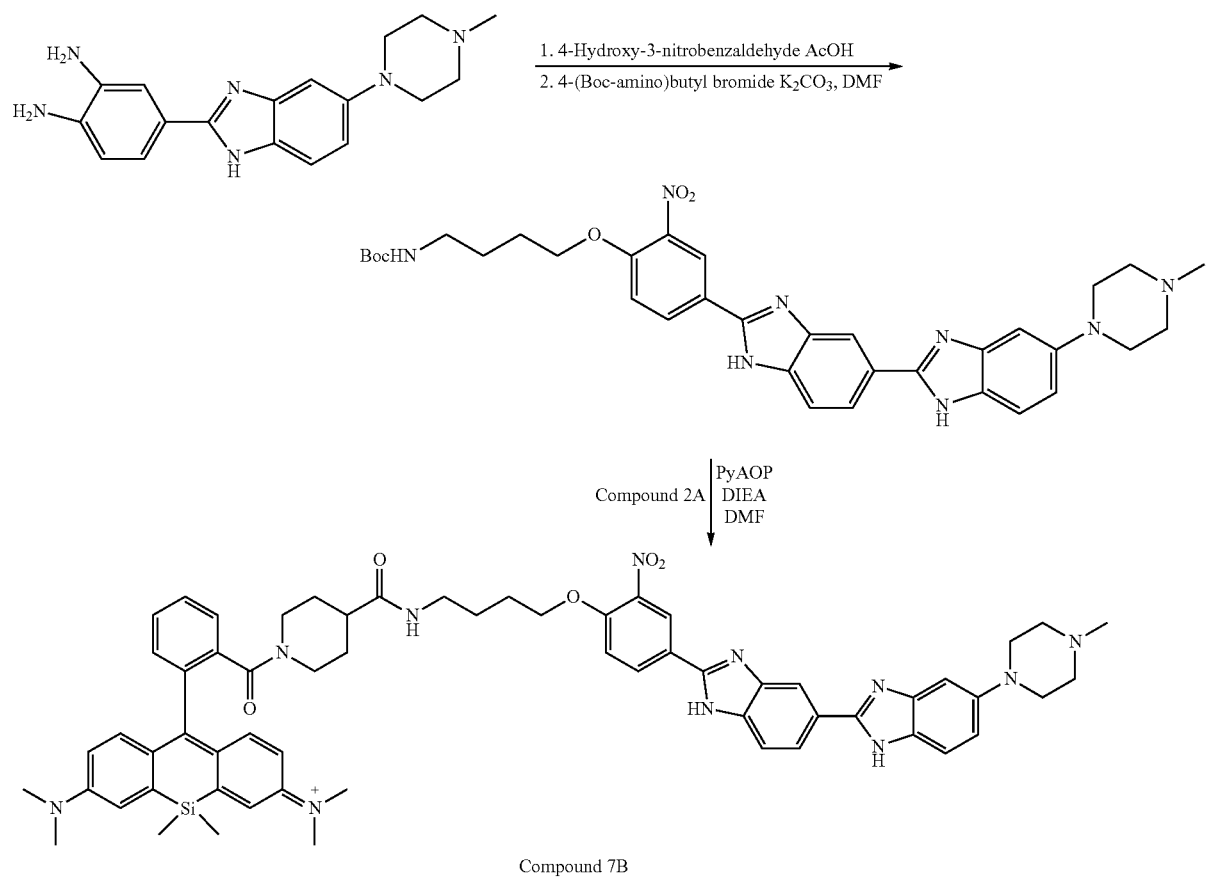

A solution of 4-[6-(4-methyl-1-piperazinyl)-1H-benzimidazol-2-yl]-2-benzenediamine (50 mg, 0.16 mmol) and 4-hydroxy-3-nitrobenzaldehyde (39 mg, 0.23 mmol) in AcOH (5.0 mL) was heated at 130° C. for 3 h. The solvent was removed using a rotavapor. The crude was purified by column chromatography on silica gel (CHCl₃:MeOH=3:1) to give Intermediate 1 (22 mg, 18%).

Example 2. Nuclear Staining

To demonstrate the applicability of Compound 2-based fluorescent materials, a live cell nuclear dye was synthesized by incorporating a Hoechst moiety at the ESP-dye linker site. Unexpectedly, Compound 2-based probes greatly improved fluorophore brightness without sacrificing other desired properties.

Figure 3A:
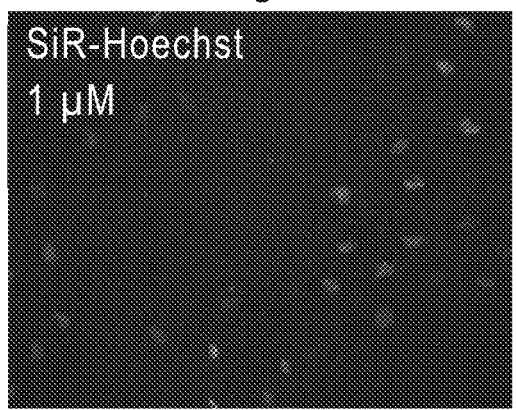
FIGS. 3A-3E show a comparison of live cell staining of SiR-Hoechst (Spirochrome, Switzerland) or Compound 4 at two different concentrations and of the mean nuclear signal intensity. Positive staining cells appear as gray to white objects on a black background. Staining was noticeably brighter with Compound 4.
Figure 3B:
Figure 3C:
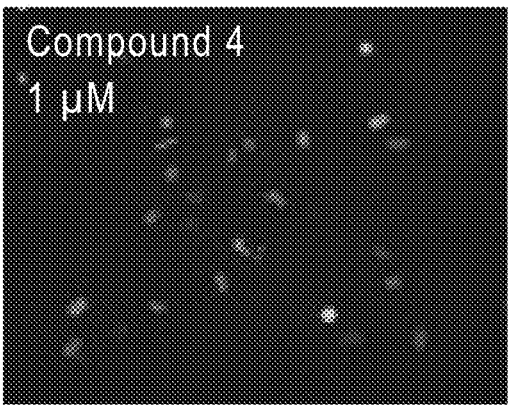
Figure 3D:
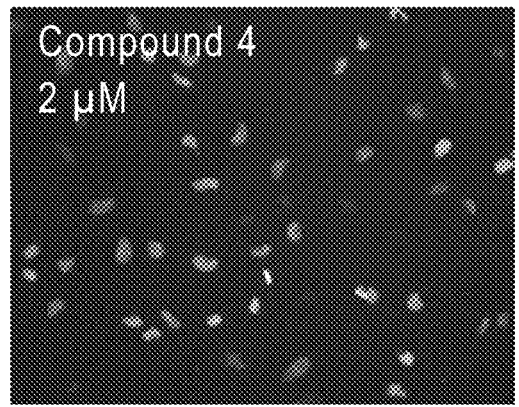
Figure 3E:
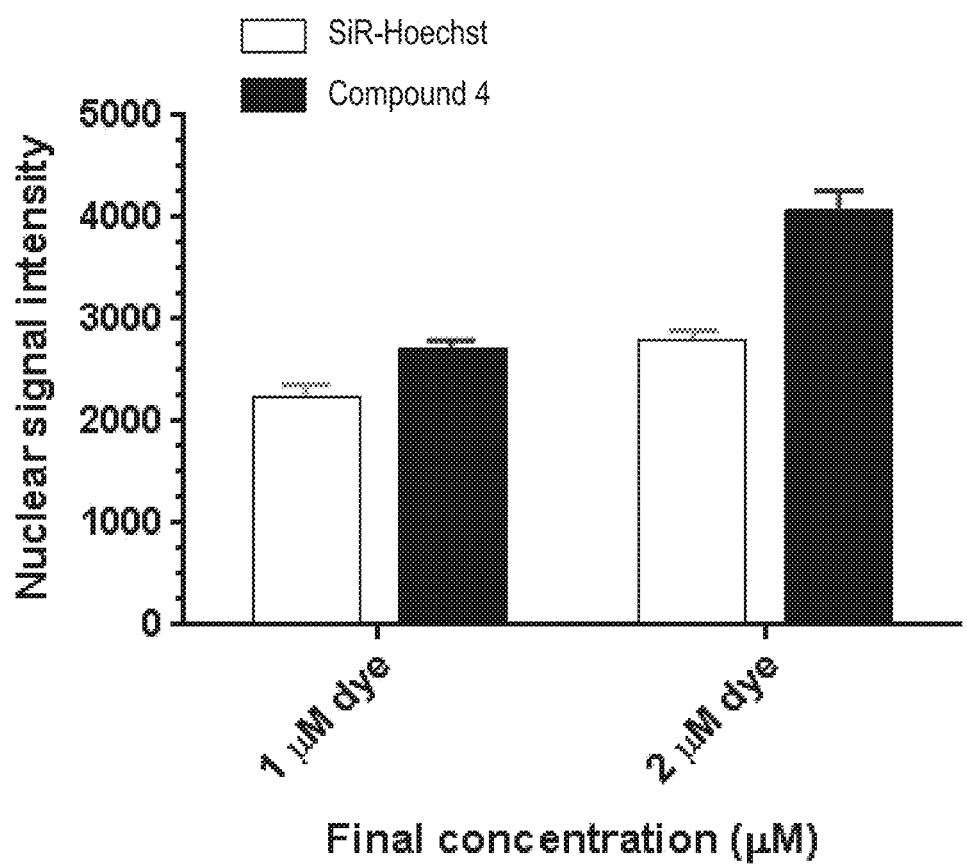

The fluorescence intensity of Compound 4 was compared to SiR-Hoechst (Spirochrome, Switzerland) using fluorescence microscopy. Live HeLa cells were stained with SiR-Hoechst or Compound 4 at 1 µM or 2 µM for 30 minutes at 37° C. After washing with LCIS buffer to remove excess dye, images from 5 replicates were collected using the Cy5 channel of a fluorescence microscope and analyzed using HCS Studio software. Representative images of cells are shown in FIGS. 3A-3B (stained with SiR-Hoechst) and FIGS. 3C-3D (stained with Compound 4). FIG. 3E shows a bar plot comparing the nuclear signal intensity of cells stained with SiR-Hoechst and Compound 4. The mean nuclear signal intensity was 48% higher in the cells stained with Compound 4 than in the cells stained with SiR-Hoechst, based on averaging the ratios of fluorescence intensity at 1 µM and 2 µM.

Example 3. Cytoskeletal Staining

To further demonstrate the applicability of Compound 2-based fluorescent materials, a tubulin probe also was made using a targeting ligand, docetaxel. Unexpectedly, Compound 2-based probes greatly improved fluorophore brightness without sacrificing other desired properties. The fluorescence intensity of Compound 5 (a tubulin probe using docetaxel as the target-binding moiety) was compared to SiR-Taxol (Spirochrome, Switzerland). Live HeLa cells were stained with 0.5 µM Compound 5 or SiR-Taxol for 30 minutes at 37° C. and prepared for imaging. Images are shown in FIGS. 4A-4B (stained with Compound 5), and FIGS. 4C-4D (stained with SiR-Taxol). Cells stained with Compound 5 showed a brighter signal than cells stained with SiR-Taxol.

Example 4. Nuclear Staining in Live and Fixed Cells and Photostability of Compound 7

Figure 2E:
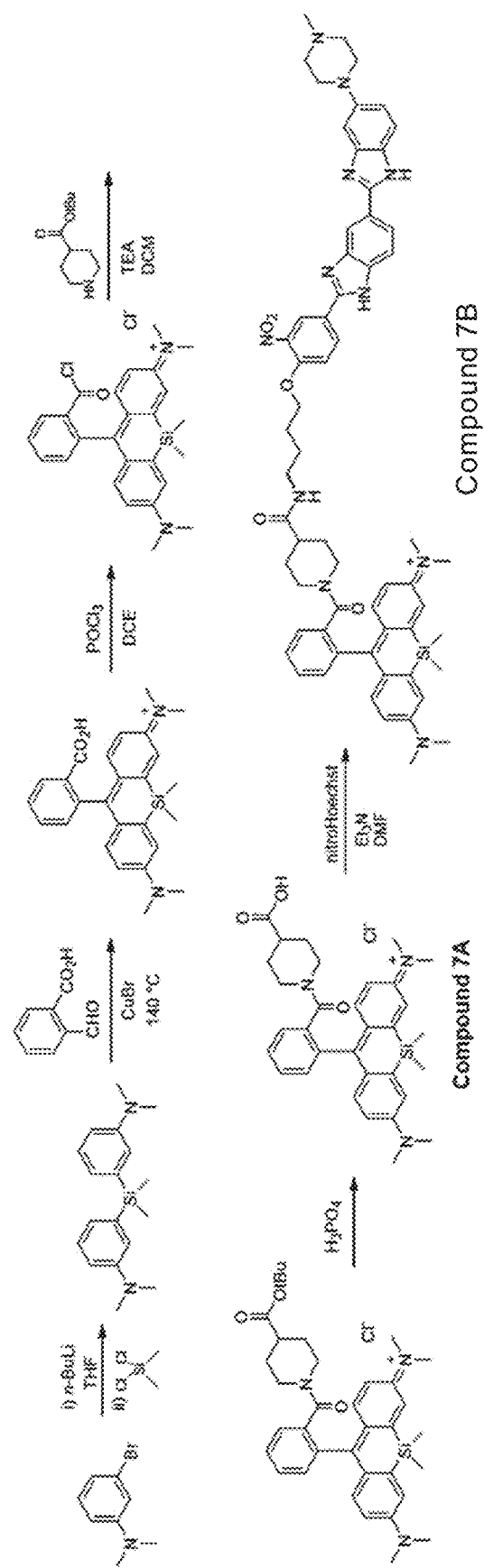

SiR derivatives exist in equilibrium via 2'-carboxyl group on the phenyl ring between a non-fluorescent spirolactone and a fluorescent zwitterion. The spirolactone form is a predominant form enabling SiR cell permeability. To make a cell impermeant SiR dye, a bulky secondary amine, such as piperidine, was incorporated onto the 2'-carboxyl group, thereby preventing spirolactonization and resulting in the SiR dyes always being fluorescent or "on". Compound 7A was synthesized and coupled with Hoechst to make Compound 7 or with nitroHoechst to make Compound 7B (FIG. 2E).

The fluorescence intensity and photostability of Compound 7 were compared with TO-PRO-3, a fixed cell nucleic acid stain with far-red fluorescence. Fixed HeLa cells were stained with 1 µM Compound 7 or TO-PRO-3 for 30 minutes at RT and prepared for imaging using the Cy5 channel of a fluorescence microscope. As shown in FIG. 5C, Compound 7 staining was unexpectedly brighter than TO-PRO-3 staining shown in FIG. 5A. Compound 7 still retained substantial fluorescence, as shown in FIG. 5D, after a 1 minute exposure to excitation light, whereas the TO-PRO-3 staining was more diminished, as shown in FIG. 5B.

Because Hoechst dye is fluorescent in the blue channel, there is a possibility of bleed-through into the blue channel of the Hoechst-conjugated SiR dyes. Addition of a nitro group to the Hoechst moiety resulting in Compound 7B, the bleed-through was surprisingly reduced by about 50% in the DAPI channel. In addition, the signal in the Cy5 channel was surprisingly increased by about 12%.

HeLa cells were plated on a 96-well plate at a density of 5 k/well and left overnight (o/n) in the $CO_2$ incubator. The cells were then formaldehyde-fixed and detergent-permeabilized. The cells were then stained with either 0.5 µM final concentration of Compound 7 or Compound 7B. The cells were then washed and imaged on a CellInsight CX5 high content imaging instrument. FIGS. 6A-6D show that Compound 7B is brighter than Compound 7 when imaged in the Cy5 channel (FIGS. 6A and 6C, respectively), and shows less bleed-through into the DAPI channel (FIGS. 6B and 6D, respectively). FIG. 6E shows that the Compound 7B fluorescence signal increased 12% in the Cy5 channel when compared to Compound 7 (see FIG. 6E, #3 and #1, respectively), and the Compound 7B fluorescence signal surprisingly decreased by 50% in the DAPI channel when compared with Compound 7 (FIG. 6E, #4 and #2, respectively).

Example 5. Photostability of Compound 10B

Attaching a water-soluble linker to SiR compounds of the present disclosure increases their water-solubility, which is useful for antibody labeling and other applications. The water-soluble SiR dyes of the present disclosure and their conjugates were extremely photostable compared with AlexaFluor 647 conjugates.

Figure 7A:
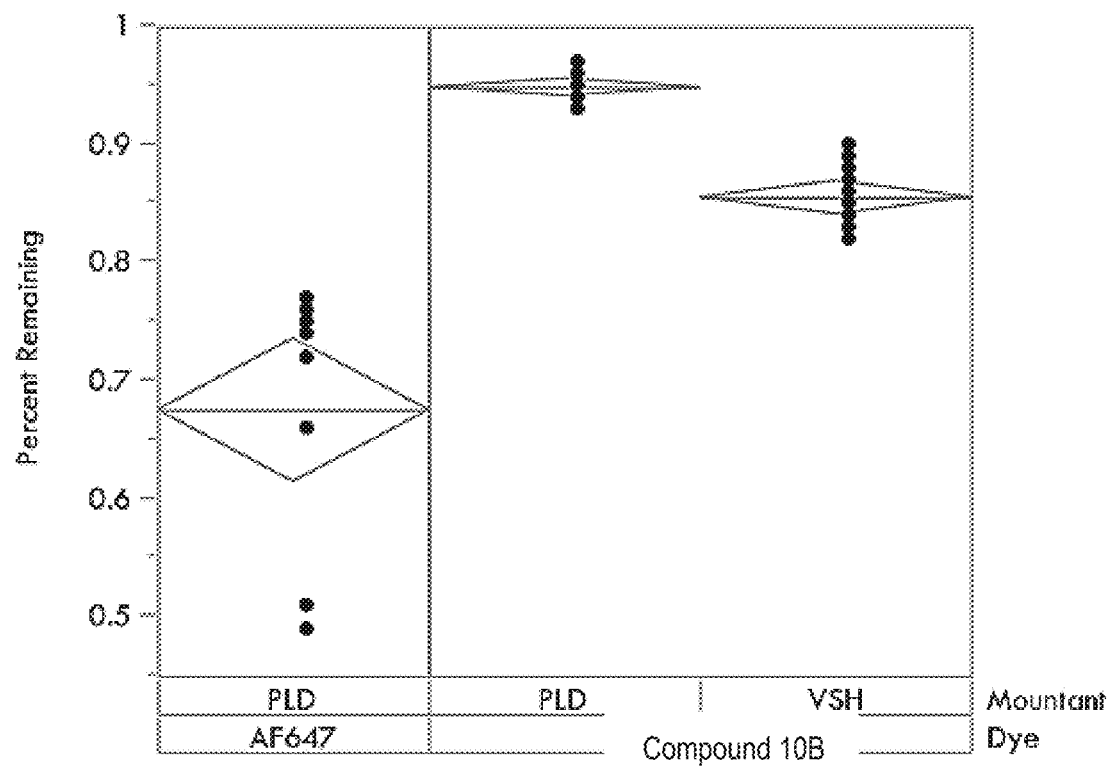
FIGS. 7A-7B compare the photostability of Compound 10B to ALEXA FLUOR™ 647 dye ("AF647", Thermo Fisher Scientific, Waltham, MA) after preparing the slides with PROLONG™ Diamond ("PLD", Thermo Fisher Scientific, Waltham, MA) or VECTASHIELD™ mounting medium ("VSH", Vector Laboratories, Burlingame, CA). HeLa cells were placed on slides and stained with 50 μM of Compound 10B or AF647.
Figure 7B:
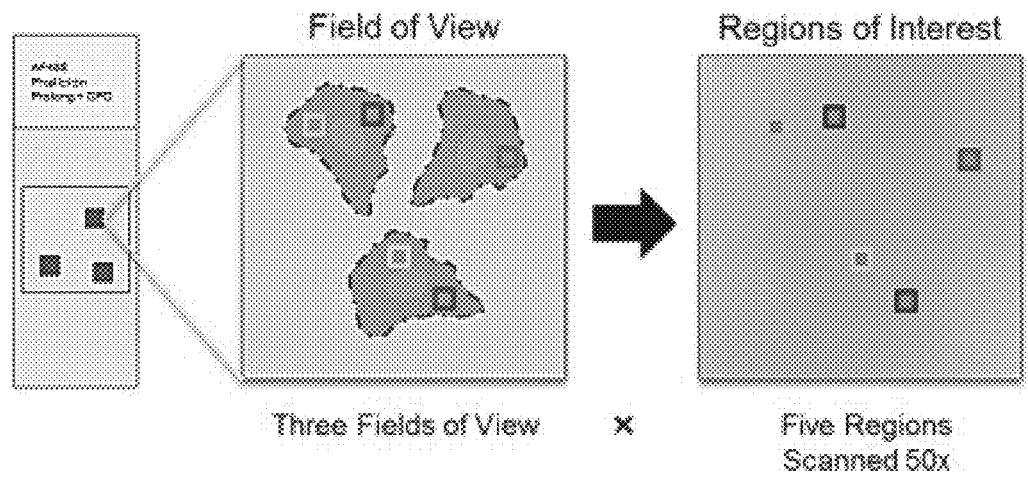

Hela cells were placed on slides and stained with 50 µM of Compound 10B or ALEXA FLUOR™ 647 DYE ("AF647", Thermo Fisher Scientific, Waltham, MA) for 60 minutes at 25° C. Slides were mounted with PROLONG™ Diamond ("PLD", Thermo Fisher Scientific, Waltham, MA) or VECTASHIELD™ (Vector Laboratories, Burlingame, CA) to reduce photobleaching, and cover-slipped. FIG. 7B shows how each specimen was imaged and how for each sample, regions of interest within 3 fields of view were selected for scanning. Each region was scanned 50 times with a confocal microscope using the 633 nm laser and then imaged. AF647 plus VECTASHIELD was completely photobleached (data not shown). As shown in FIG. 7A, the percentage of fluorescence remaining after 50 scans in specimens stained with Compound 10B was greater than in specimens stained with AF647 regardless of the mounting medium used.

Example 6. Fluorescence Characteristics of Disclosed SiR Compounds

The fluorescence characteristics of various disclosed compounds and ALEXA FLUOR™ 647 dye (AF647) dissolved in water (dye only) or as goat anti-mouse (GAM) IgG conjugates dissolved in phosphate buffered saline (PBS) were determined. Three replicates were performed to determine the excitation and emission maxima and quantum yield. Quantum yield was measured for the dye only samples. Data are shown in Table 3 (ND=not determined).

TABLE 3

Excitation and emission maxima of compounds dissolved in water only or as GAM IgG conjugates dissolved in PBS

| Compound | Quantum yield | Dye Only in water | | GAM IgG conjugate in PBS | |
|---|---|---|---|---|---|
| | | Max Abs (nm) | Max Em (nm) | Max Abs (nm) | Max Em (nm) |
| 2A | ND | ND | ND | 664 | 683 |
| 10A/B | 0.41 | 666 | 678 | 667 | 688 |
| 8 | ND | ND | ND | 664 | 684 |
| 12 | 0.45 | 661 | 673 | 662 | 681 |
| 11 | 0.38 | 670 | 683 | 671 | 693 |
| 14 | ND | ND | ND | 665 | 685 |
| 13 | 0.5 | 630 | 642 | 635 | 655 |
| AF647 | 0.32 | 650 | 675 | 651 | 673 |

Certain compounds were tested when dissolved in solvents. Three replicates were performed to determine the excitation and emission maxima. Data are shown in Table 4.

TABLE 4

Excitation and emission maxima of compounds dissolved in solvents

| Compound | Max Abs (nm) | Max Em (nm) | Solvent |
|---|---|---|---|
| 7A | 657 | 682 | MeOH |
| 5 | 650 | 676 | MeOH/HCl |
| 7 | 672 | 678 | TE |

Example 7. Near Infrared-Emitting SiR Phosphoramidites and Labeled Polynucleotides Silyl substitution generally gives rhodamine dyes a 75 nm spectral shift toward red. For synthesis of labeled nucleotides and polynucleotides (e.g., primers and probes) that emit above 650 nm, the silyl substitution is incorporated into dichloro-rhodamine phosphoramidites to create Compounds 51-54. The calculated emission maxima are shown below in Table 5.

TABLE 5

Calculated emission maxima of SiR phosphoramidites

| Compound | Calc. Emission Max (nm) |
|---|---|
| Compound 51 | 656 |
| Compound 52 | 678 |
| Compound 53 | 693 |
| Compound 54 | 711 |

Generation of a FAM- and SiR-labeled primer using Compound 54-Phosphoramidite and FAM Phosphoramidite is illustrated in FIG. 8. Compound 54 (and similar compounds) can be used to automate synthesis of multi-chromophore structures for use in FRET assays. Generation of a primer labeled with FAM and an SiR moiety from an NHS ester of Compound 59 is illustrated in FIG. 9.

Example 8. Fixed Cell Stains; Antibody Conjugation

SiR compounds exist in equilibrium between the zwitterionic (open) form and the spiro (closed) form as noted elsewhere herein. Binding of a target-binding moiety to its probe to the target of the ligand such as fixed cells or antibody, may favor the more fluorescent open form, whereas free, unbound SiR probes may exist mainly in the closed form, e.g., stabilized by reversible hydrophobic aggregation.

Pathways that give SiR compounds that can be used for different applications are shown in FIGS. 10A-10B. Preparation of an SiR compound capable of staining fixed cells is shown in FIG. 10A.

As some SiR dyes may not be sufficiently water-soluble for some uses without solubilizing functionalities, a water-soluble linker can be attached to an SiR to facilitate conjugation such as antibody labeling. An exemplary solubilizing substituent is one comprising a polyethylene oxide linker, reactive ligand, and phenyl substituted with 2 sulfonates, e.g.,

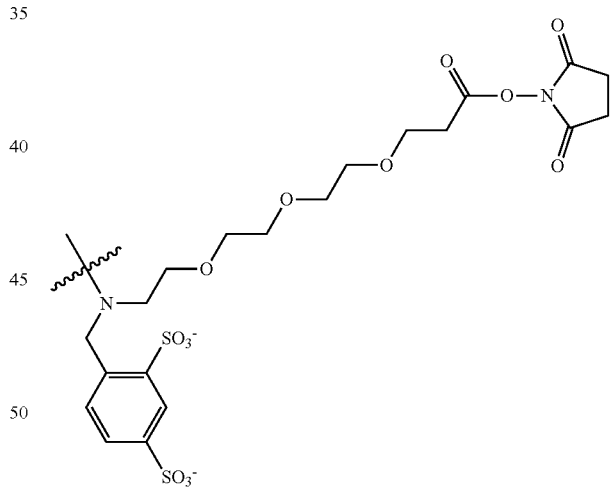

where the wavy line indicates the connection to the SiR moiety. See, e.g., Compounds 10A-14. An exemplary synthetic pathway for a water-soluble SiR for antibody labeling is shown in FIG. 10B.

The water-solubility of the SiR compounds provided herein can also be increased by the addition of one or more sulfonate groups. See, e.g., Compound 8.

Example 9. Effect of Substitutions and Conjugation on Fluorescence Characteristics of SiR Compounds Experiments were performed to examine the effect of different SiR substitution patterns on absorption maxima using Compounds 10A, 11, 12, and 13. One or both of the vinyl groups of Compound 11 are replaced with methyl in Compounds 10A and 12, respectively. In Compound 13, one methyl group on each of the two exocyclic amines was eliminated relative to Compound 12. It was found that the absorption maxima shifted about 5 nm to blue when each vinyl group was changed to a methyl. A 30 nm shift was observed when one methyl group on each of the two exocyclic amines was eliminated (Table 6). Therefore, modification of SiR dyes using groups linked to the SiR moiety through the Si have a smaller effect than the removal of methyl groups.

TABLE 6

Excitation and emission maxima of compounds dissolved in water only or as IgG conjugates dissolved in PBS

|  | Si,Si-Divinyl-N,N-tetramethyl-SiR (11) | Si-vinyl-Si-methyl-N,N-tetramethyl-SiR (10A) | Si,Si-dimethyl-N,N-tetramethyl-SiR (12) | Si,Si-dimethyl-N,N-dimethyl-SiR (13) | AF647 |
|---|---|---|---|---|---|
| absorption in water ($\lambda$abs) | 670 nm | 666 nm | 661 nm | 630 nm | 650 nm |
| Emission in water ($\lambda$em) | 683 nm | 678 nm | 673 nm | 642 nm | 670 nm |
| Quantum Yield | 38% | 41% | 45% | 50% | 32% |
| Absorption of IgG conjugates | 671 nm | 668 nm | 664 nm | 635 nm | 650 nm |
| Emission of IgG conjugates | 692 nm | 688 nm | 683 nm | 655 nm |  |

Figure 11A:
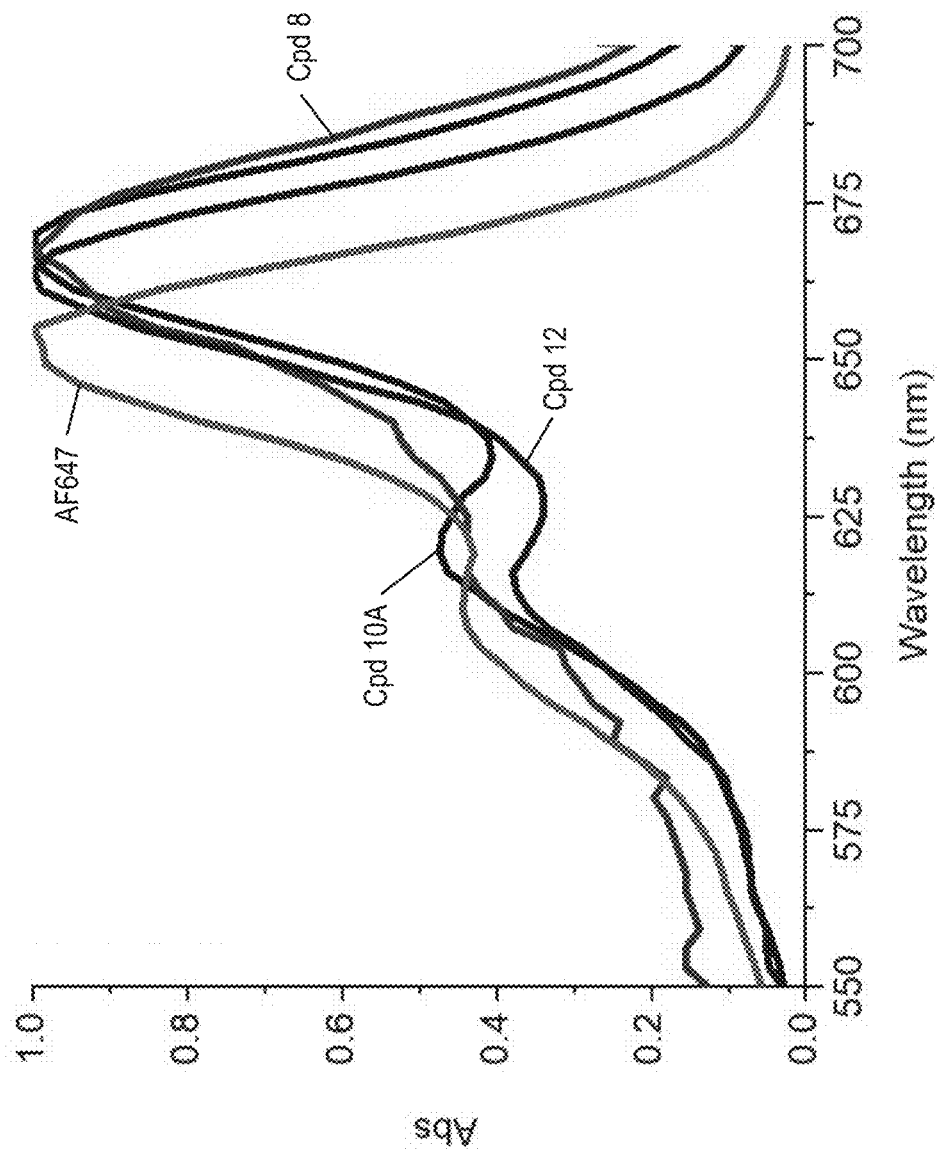
FIGS. 11A-11B compare the absorbance and emission spectra of various compounds with ALEXA FLUOR™ 647 dye ("AF647", Thermo Fisher Scientific, Waltham, MA).
Figure 11B:
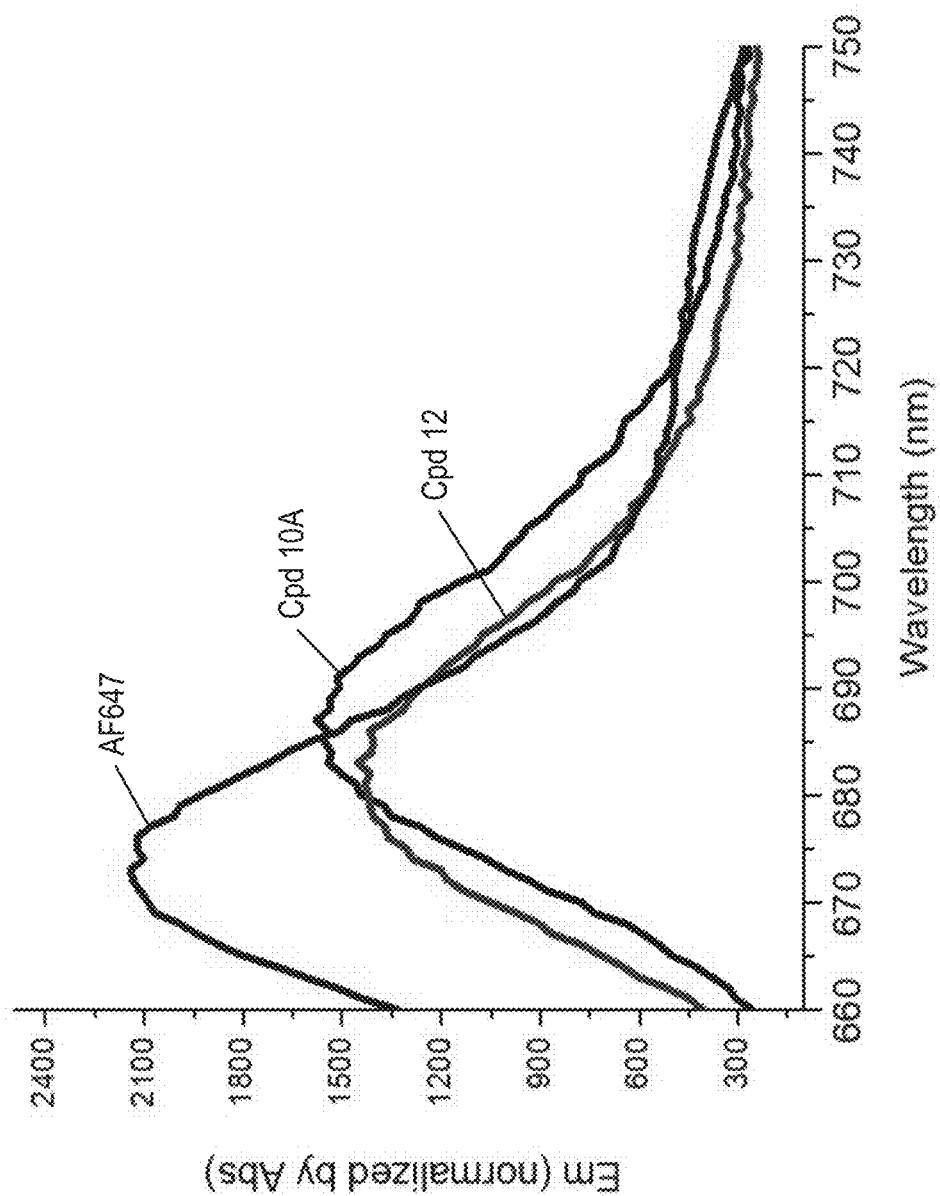

The effect of conjugation of an SiR, in this example Compounds 8, 10A, and 12, to IgG on absorbance (shown in FIG. 11A) and on emission (shown in FIG. 11B) maxima were compared with IgG-AF647. The absorption and emission maxima of the SiR-conjugates (665 nm/690 nm) are approximately 20 nm red-shifted compared with AF647 conjugate. The emission maximum shifted 15 nm to red. This shift resulted in less signal than AF647 when using a Cy5 filter.

HeLa cells were plated at a density of 7.5 k/well in a 96-well plate and left over night in $CO_2$ incubator. Cells were treated with etoposide at 50 µM. The cells were then washed 3× with PBS and cells fixed in 4% formaldehyde for 15 mins. The cells were washed 3× with PBS and then permeabilized with 0.25% Triton X-100 in PBS for 15 mins. The cells were washed 3× with PBS and then blocked in 1% BSA in PBS for 1 hour. The cells were washed IX with PBS and then incubated with primary antibody diluted 1 to 1000 (Enzo, ADI-KAM-CC255-F). The cells were washed 3× with PBS and then incubated with secondary antibody label with AF647 (DOL 4.9) or Compound 10A (DOL 5.4) conjugated to at 5 µg/mL for 1 hr. The cells were washed 3× with PBS and counterstained with DAPI. Imaged on Thermo Fisher Scientific Cellomics ArrayScan VTI instrument. Data analysis/graphing was carried out in Prism.

Figure 12A:
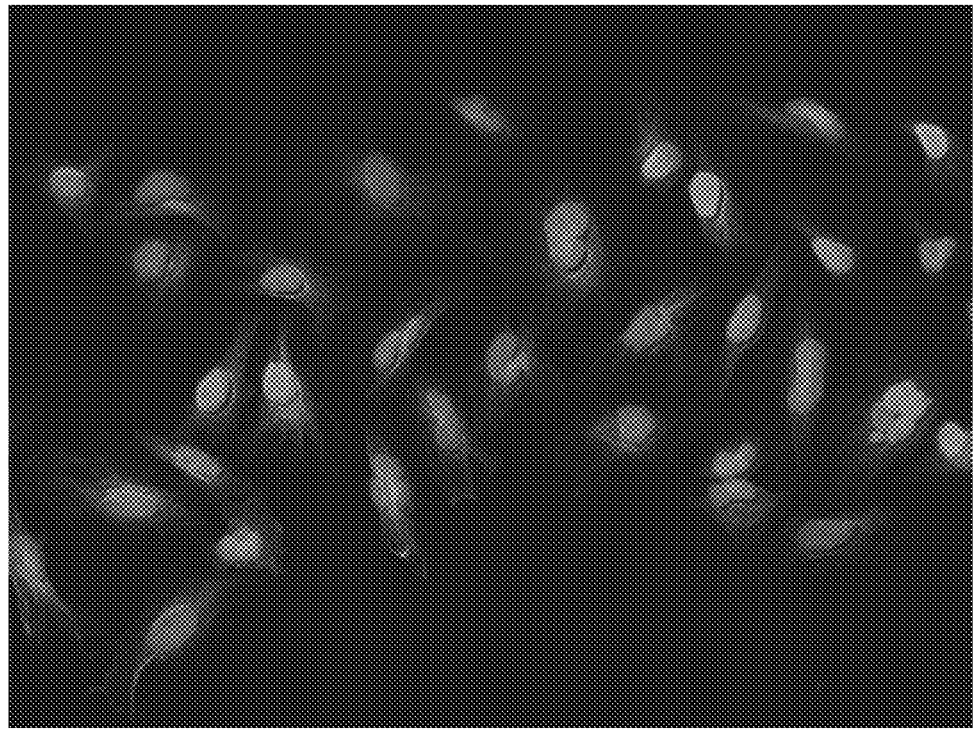
FIGS. 12A-12C shows examples of cells stained with an anti-tubulin antibody and ALEXA FLUOR™ 647 dye ("AF647", Thermo Fisher Scientific, Waltham, MA) or Compound 10A conjugated to a secondary antibody at a degree of labeling ("DOL") of 15. Cells staining positive for tubulin appear gray to white on the black background. Nuclei were stained with DAPI.
Figure 12B:
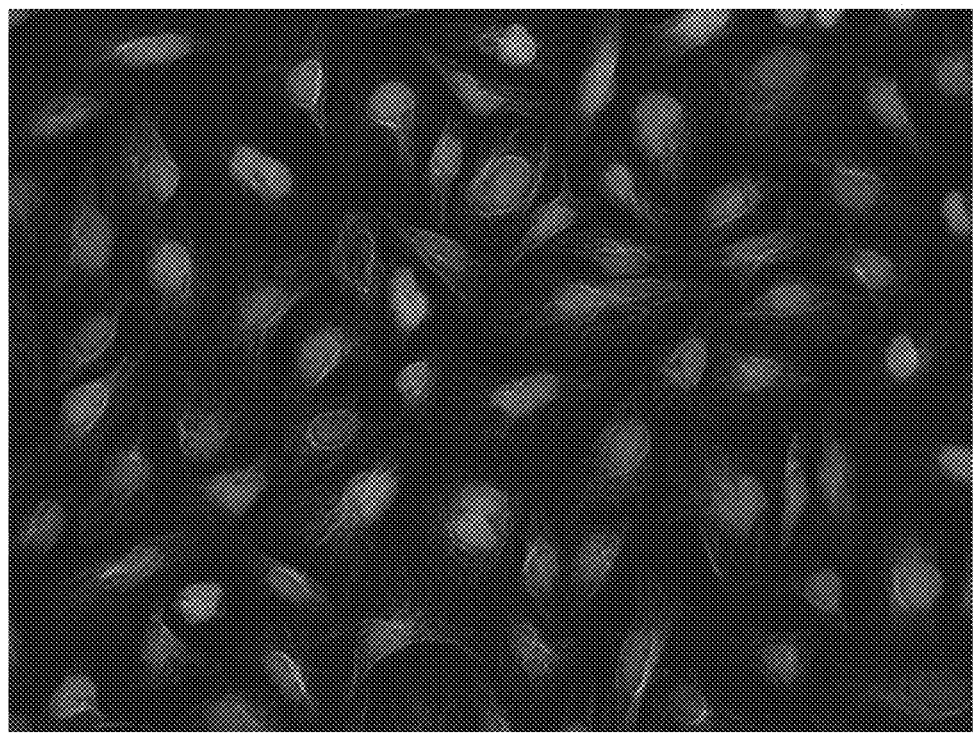
Figure 12C:
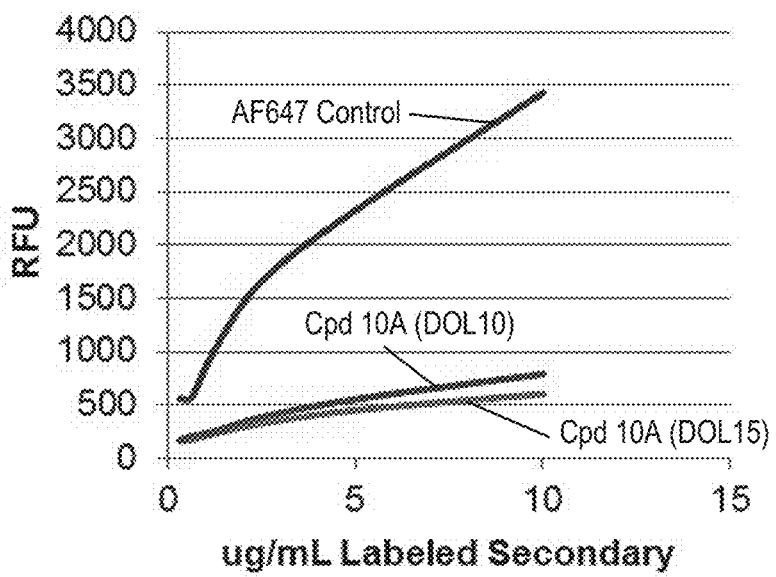

The fluorescence intensity of SiR conjugates, Compound 10A (DOL=15) and Compound 10A (DOL=10), where DOL is the degree of labeling, were compared to an AF647 conjugate using fluorescence microscopy. Live mouse cells were stained with mouse anti-tubulin conjugated to AF647 (shown in FIG. 12A), or mouse anti-tubulin conjugated with Compound 10A (DOL=15 shown in FIG. 12B) at increasing concentrations for 60 minutes at 25° C. After washing with PBS buffer to remove excess dye, images were collected using the Cy5 channel of a fluorescence microscope and analyzed using integrated software. Images of cells are shown in FIGS. 12A-12B. FIG. 12C shows a graph comparing the fluorescence versus the concentration of the labeled secondary reagent. The SiR dyes gave images 6-8 fold dimmer that AF647 in the Cy5 channel, consistent with the shifted maxima discussed above. The SiR dye-conjugates showed good target specificity, and no off-target or background fluorescence was observed. Little to no photobleaching was observed during imaging.

The fluorescence intensity and photostability of SiR-Goat anti-mouse (GAM) conjugates made from Compounds 13 and 14 (structures shown in FIG. 1G) were compared with AF647.

A549 cells were plated at a density of 5,000 cells per well on Greiner 96 well plates and allowed to adhere overnight. The following day, they were treated for two hours at 37° C. with 50 µM etoposide to induce phosphorylation of pH2AX for antibody probing, then fixed for 20 minutes at room temperature in 4% PFA, prepared in PBS. After fixation, cells were rinsed 3× in PBS and permeabilized for 20 minutes with 0.1% Triton X-100, prepared in PBS. Following Triton treatment, cells were washed 3× in PBS and placed in blocking solution, made with 3% BSA in PBS. Each plate was treated with primary antibody, prepared in blocking solution at 5 µg/mL, either at room temperature for one hour at 4° C. Following incubation with primary antibody, cells were washed 3× in PBS and stored in blocking solution before probing with secondary antibody. Secondary antibody labeled with Compound 13 (DOL 4.7); Compound 14 (DOL 4.0) or AF647 (DOL 4.9) was prepared from 5 µg/mL in blocking solution and cells were incubated for one hour at room temperature before washing 3× in PBS and moving plates to the CX-5 CellInsight for quantification of signal. The fluorescent signal data was collected every second for over 700 seconds' period. Data analysis/graphing were carried out in Prism.

Figure 13:
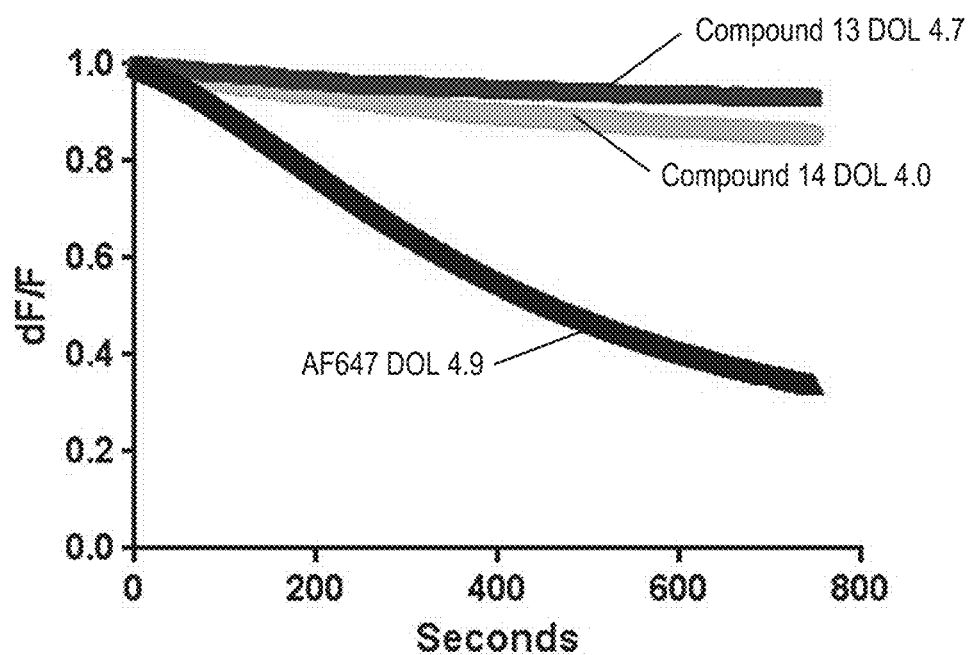
FIG. 13 shows a comparison of antibody conjugates of Compound 13, Compound 14 or AF647 in their ability to resist photobleaching. Both of Compounds 13 and 14 were substantially resistant to photobleaching for over 700 seconds exposure whereas AF647 was not resistant. DOL indicates degree of labeling (e.g., SiR dye moieties per antibody).

Fluorescence intensity was monitored in samples mounted without anti-fade medium over a period of about 12 minutes of exposure to excitatory light. As shown in FIG. 13, both Compounds 13 and 14 were much more resistant to photobleaching throughout the time course compared to AF647.

Example 10. Near Infrared-Fluorescing SiR Dyes

Near infrared-fluorescing SiR dyes including Compounds 18, 20, 22, 24, and 26 (shown in FIG. 1I), Compounds 28, 29, 30, 31, and 32 (shown in FIG. 1J), Compounds 45 and 46 (shown in FIG. 1M), and Compounds 47, 48, 49, and 50 (shown in FIG. 1N) are synthesized and tested for emission maxima. The Emission maxima are found to be shifted toward the red wavelengths relative to compounds such as Compound 1.

Example 11. Nucleic Acid Analysis

SiR-phosphoramidite compounds such as Compounds 51-54 are used in polynucleotide synthesis reactions to provide fluorescendy labeled primers and probes. The primers and probes are used in amplification and sequencing reactions to provide labeling and/or detection of reaction products.

Compounds 51-54 can be used in chemically automatable synthesis of polynucleotides using solid-support synthesis to provide fluorescendy labeled primers and probes Sequencing reaction products can be resolved by capillary electrophoresis and detected.

Amplification reaction products can be detected in real time using dual-labeled probes (e.g., comprising an energy transfer partner, e.g., quencher, such as TaqMan™ or molecular beacon probes) that result in product-dependent fluorescence through hybridization-dependent cleavage or conformational changes.

Example 12. Nuclear Staining with ESP-SiR Isomers

To demonstrate the applicability of different diastereomers of Compound 2 (ethylsulfopropyl-siliconrhodamine, ESP-SiR)-based fluorescent materials, a live cell nuclear dye was synthesized by incorporating a Hoechst moiety at the ESP-SiR dye linker site. Unexpectedly, a probe prepared using one of the two isomers (Compound 4B) greatly improved fluorophore brightness without sacrificing other desired properties.

The fluorescence intensity of each isomer of Compound 4 (Compound 4B and Compound 4C) was compared using fluorescence microscopy. A DMSO stock solution (1 mM) was used to prepare solutions of each isomer to a final concentration of 5, 2.5, 1.25 and 0.6 µM in PBS containing probenecid.

Figure 14:
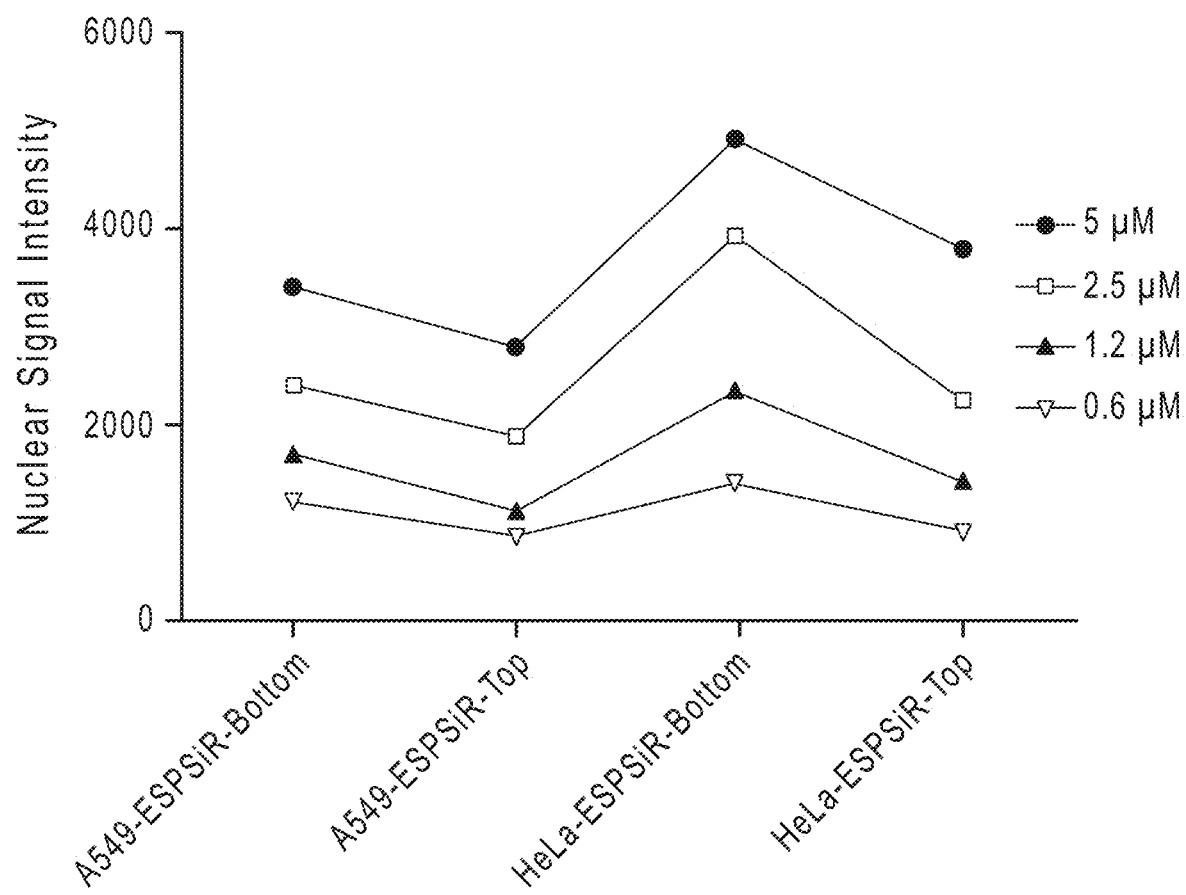
FIG. 14 shows the nuclear signal intensity of cells stained with Compound 4B (Bottom PDT) and Compound 4C (Top PDT) for cell types A549 and HeLa.

Live HeLa or A549 cells were stained with each concentration of isomer for 30 minutes at 37° C. After washing with LCIS buffer to remove excess dye, images from 5 replicates were collected using the Cy5 channel of a fluorescence microscope and analyzed using HCS Studio software. FIG. 14 shows the nuclear signal intensity of cells stained with Compound 4B and 4C. The mean nuclear signal intensity was almost 2-fold higher in both cell types stained with Compound 4B than in the cells stained with Compound 4C at each of the concentrations tested.

Figure 15A:
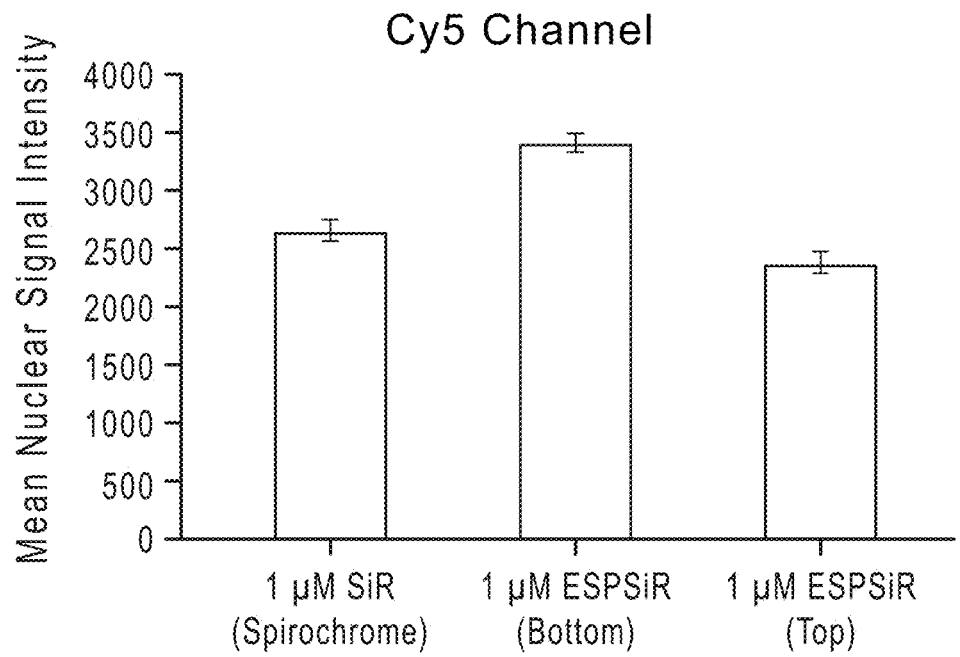
FIG. 15 shows a bar plots comparing the nuclear signal intensity of cells stained with SiR-Hoechst and Compound 4B and 4C on Cy5 and DAPI channels.
Figure 15B:
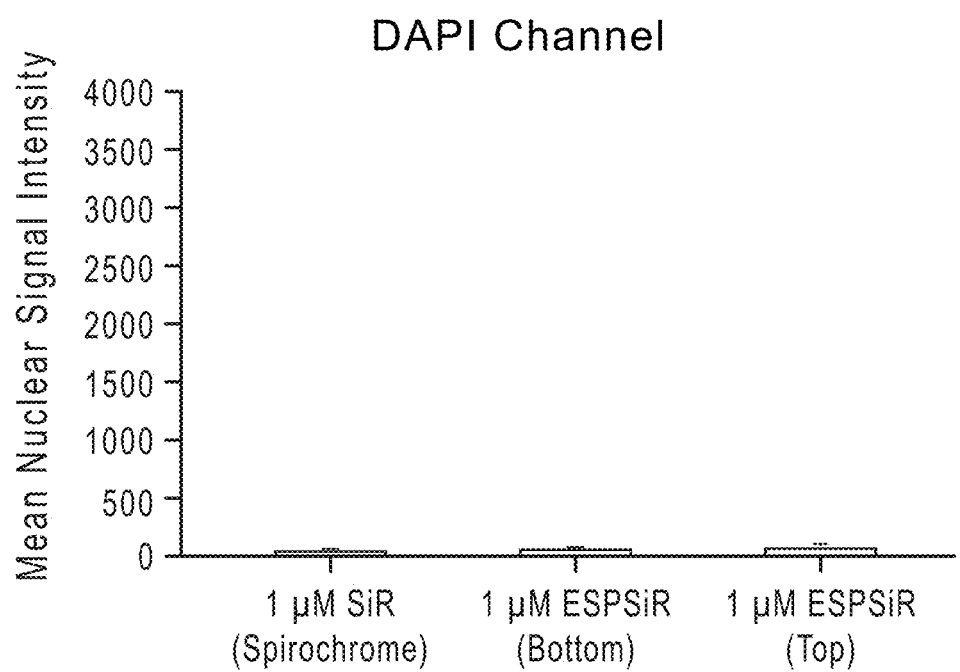

The fluorescence intensity of Compound 4B and 4C was compared to SiR-Hoechst (Spirochrome, Switzerland) using fluorescence microscopy. Live HeLa cells were stained with SiR-Hoechst or Compound 4B or 4C at 1 µM for 30 minutes at 37° C. After washing with LCIS buffer to remove excess dye, images from 5 replicates were collected using the Cy5 and D API channels of a fluorescence microscope and analyzed using HCS Studio software. FIG. 15 shows a bar plots comparing the nuclear signal intensity of cells stained with SiR-Hoechst and Compound 4B and 4C. Compound 4B exhibited higher signal intensity compared to SiR dye from Spirochrome (Switzerland) on Cy5 channel, whereas almost no signals were observed on the DAPI channel for all three compounds.

Example 13. Tubulin Staining with ESP-SiR Isomers

Figure 16:
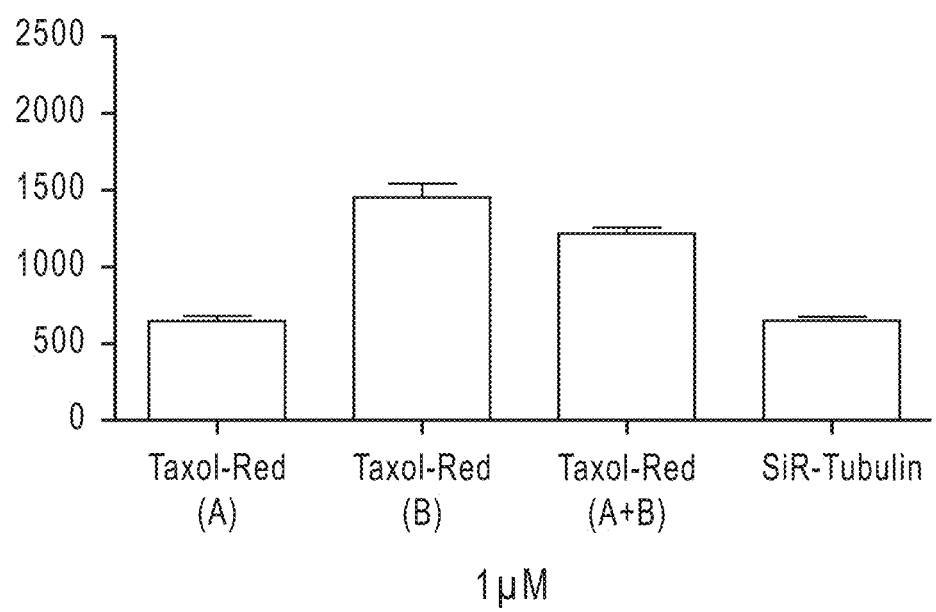
FIG. 16 shows a bar graph comparing the signal intensities of diasteromers A and B for Compound 5 as compared to a mixture of diasteromers and a commercial SiR-Taxol compound.

To further demonstrate the applicability of Compound 2-based fluorescent materials, a tubulin probe (Compound 5) also was made using a targeting ligand, docetaxel. Unexpectedly, a probe (Compound 5A) prepared using one of the diastereomers of Compound 2 greatly improved fluorophore brightness without sacrificing other desired properties. The fluorescence intensity of two diasteromers of Compound 5 and a mixture of two isomers was compared to SiR-Taxol (Spirochrome, Switzerland). Live HeLa cells were stained with 0.5 µM of each compound for 30 minutes at 37° C. and prepared for imaging. FIG. 16 shows a bar graph comparing the signal intensities of each compound tested and a mixture of diasteromers. Compound 5A (Taxol-Red (B)); bottom spot on TLC) has much better binding to tubulin as compared to Compound 5B (Taxol-Red (A) top spot on TLC), a mixture of A and B, and the SiR-Taxol compound from Spirochrome.

Example 14. Effect of Linkers on Cell Staining of ESP-SiR Isomers

To further demonstrate the performance of Compound 2-based fluorescent materials, an actin probe was synthesized using a cyclic peptide as the target-binding moiety. Unexpectedly, Compound 2-based probes (Compound 6) greatly improved fluorophore brightness without sacrificing other desired properties. The fluorescence intensity of Compound 6 was compared to SiR-Actin (Spirochrome, Switzerland).

Figure 17A:
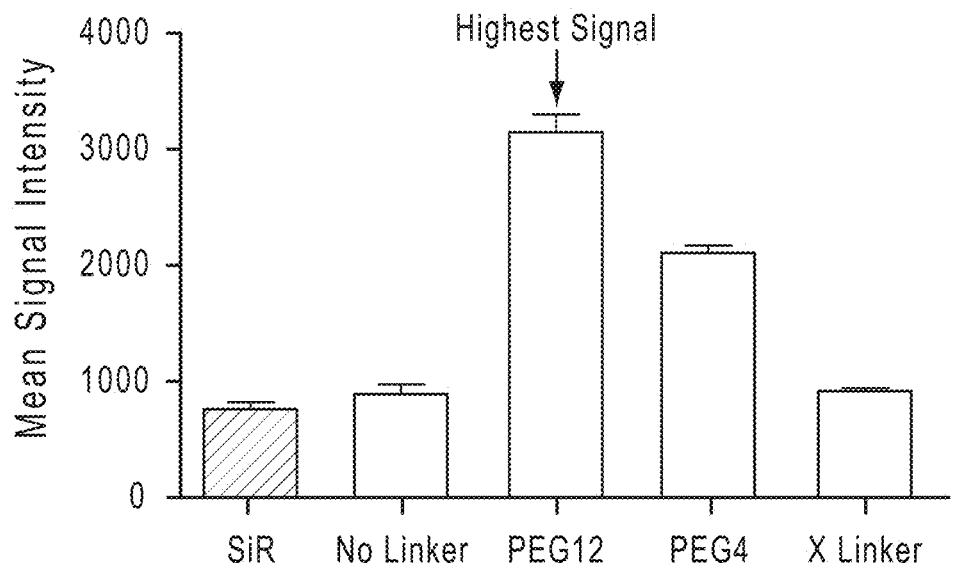
FIG. 17A shows a bar graph comparing the mean signal intensity for Compound 6 actin probes prepared with different types of linkers.
Figure 17B:
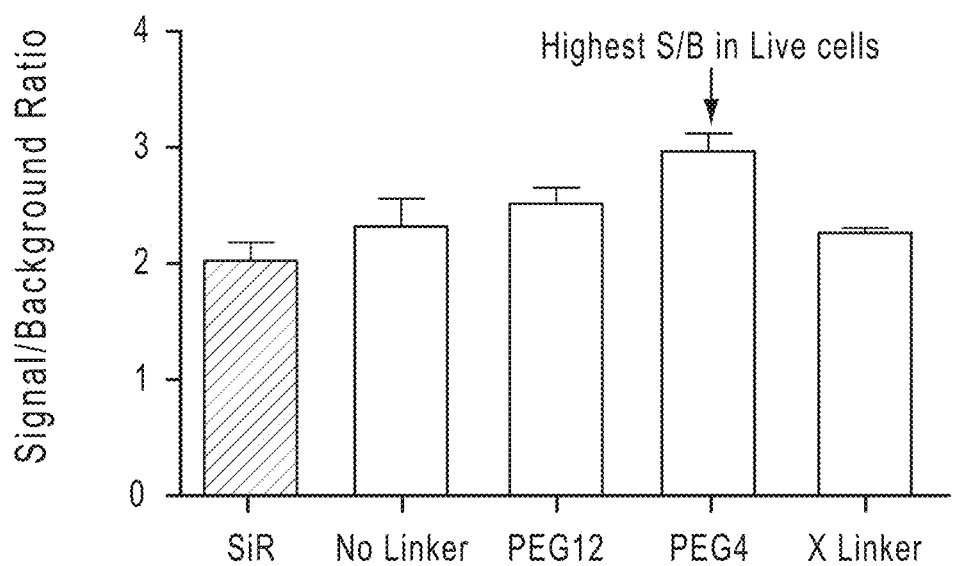
FIG. 17B shows a bar graph comparing the signal-to-background (S/B) ratio for Compound 6 actin probes prepared with different types of linkers.

Derivatives of Compound 6 were tested to compare the effect of linker type on cell staining efficacy. Derivatives including a $PEG_4$ or $PEG_{12}$ linker were compared against Compound 6 including a $C_6$ linker (X-Linker); an actin probe conjugate having no linker; and SiR-Actin (Spirochrome, Switzerland). Live HeLa cells were stained with 1 µM of each compound for 30 minutes at 37° C. and prepared for imaging as described herein. Live HeLa cells were stained with each concentration of isomer for 30 minutes at 37° C. After washing with LCIS buffer to remove excess dye, images from 5 replicates were collected using the Cy5 channel of a fluorescence microscope and analyzed using HCS Studio software. FIG. 17A and FIG. 17B show bar graphs comparing the mean signal intensity and signal intensity to background (S/B) for each compound tested, respectively. Overall, the derivative of Compound 6 with $PEG_4$ linker exhibited the lowest background (highest S/B) and most uniform staining in both live and fixed cells, whereas $PEG_{12}$ exhibited visibly higher background and uneven staining.

Figure 18A:
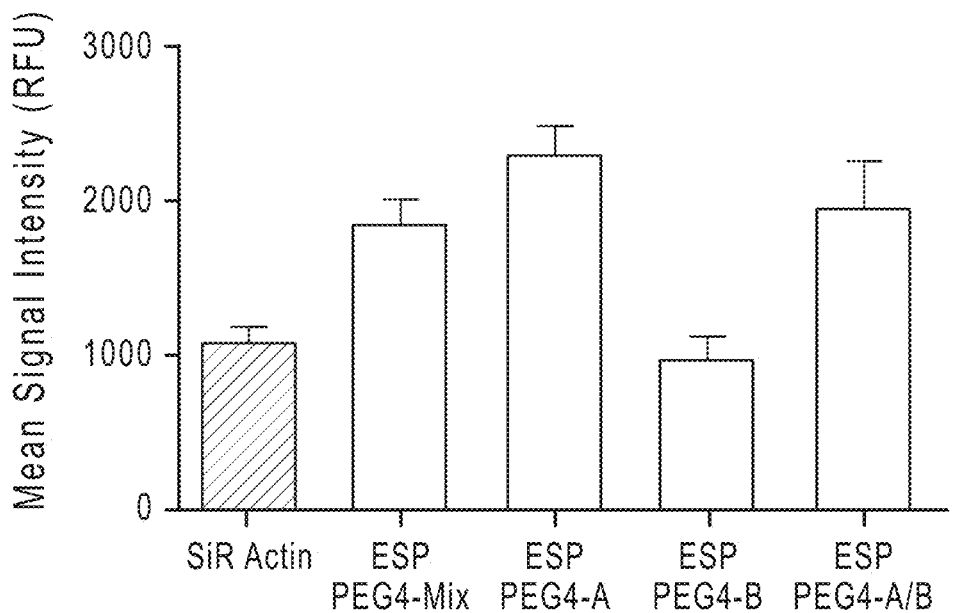
FIG. 18A shows a bar graph that compares the mean signal intensity Compound 6A, Compound 6B, a mixture of isolated Compound 6A and 6B (prior to isomer separation), a combination of the two separated isomers of Compound 6 (A/B), and cells labeled with SiR-Actin (Spirochrome).
Figure 18B:
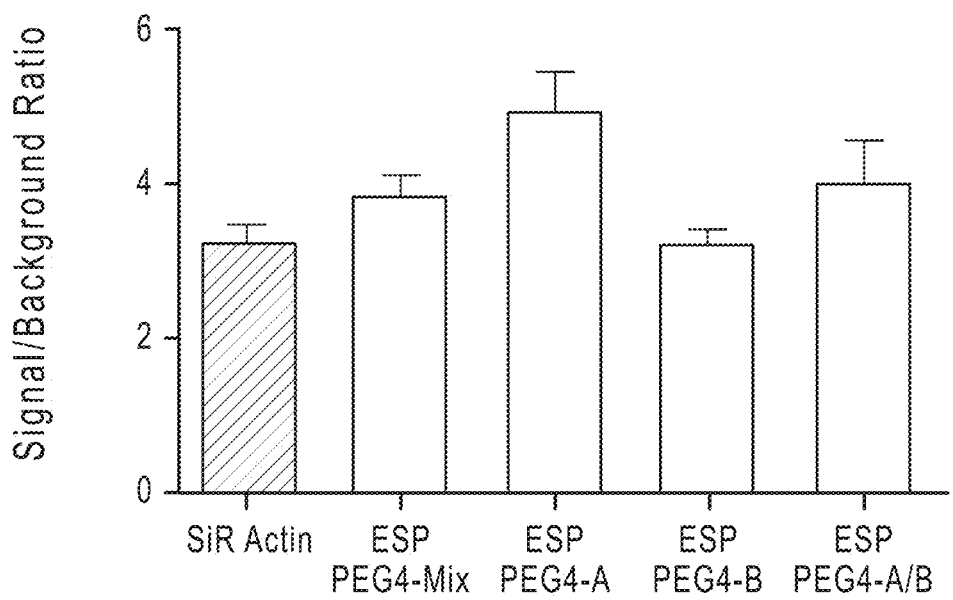
FIG. 18B shows a bar graph that compares the signal to background ratio for each of the compounds tested in FIG. 18A.

The effect of different isomers of Compound 6-PEG$_4$ on actin staining also was tested. Live HeLa cells were stained with 1 μM of each compound for 30 minutes at 37° C. and prepared for imaging as described above. FIG. 18A shows a bar graph that compares the mean signal intensity Compound 6A-A (ESP-PEG4-A), Compound 6A-B (ESP-PEG4-B), a mixture of isolated Compound 6A-A and 6A-B (prior to isomer separation) and a combination of the two separated isomers of Compound 6A-A and 6A-B. The signal intensity was compared against cells labeled with SiR-Actin (Spirochrome). FIG. 18B shows a bar graph that compares the signal to background ratio for each of the compounds tested. Compound 6A-A is about three times brighter than Compound 6A-B, although both share the same localization specificity.

What is claimed is:

1. A compound of formula (I), or a spirolactone form and/or salt thereof:

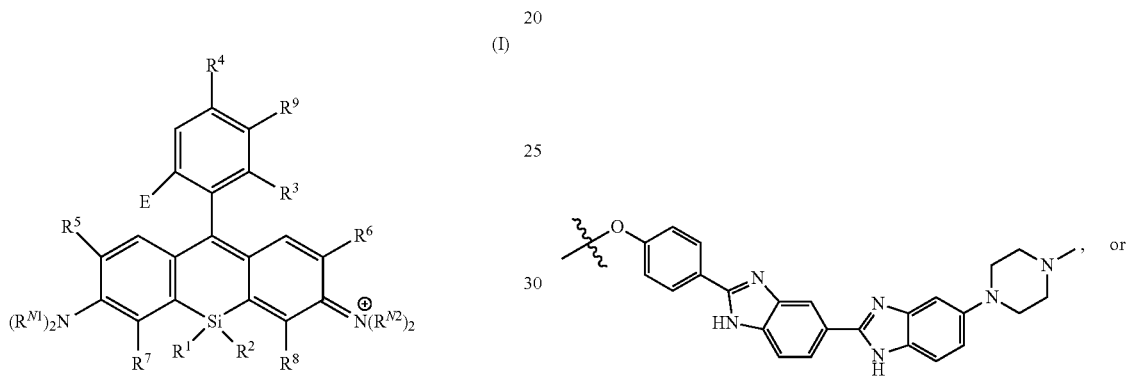

wherein:
$R^1$ is methyl or $C_{2-6}$ alkyl or -$L^1$-$R^{B1}$;
$R^2$ is methyl, $C_{2-6}$ alkyl, or -$L^1$-$R^{B1}$;
$L^1$ is a linker comprising a combination of two or more groups selected from alkyl, —C(O)NH—, —S—, —O—, and/or —S(O)—;
$R^3$ is —COOH, $CO_2^-$, or $SO_3^-$;
each of E, $R^4$, $R^5$, $R^6$, $R^7$, $R^8$, and $R^9$ is H;
each $R^{N1}$ is independently H, methyl, or $C_{2-4}$ alkyl;
each $R^{N2}$ is independently H, methyl, or $C_{2-4}$ alkyl;
provided that
(i) at least one of $R^1$ or $R^2$ is -$L^1$-$R^{B1}$, and the $R^{B1}$ group comprises a nucleic acid-binding moiety or a cytoskeleton-binding moiety,
wherein the nucleic acid-binding moiety or the cytoskeleton-binding moiety is selected from

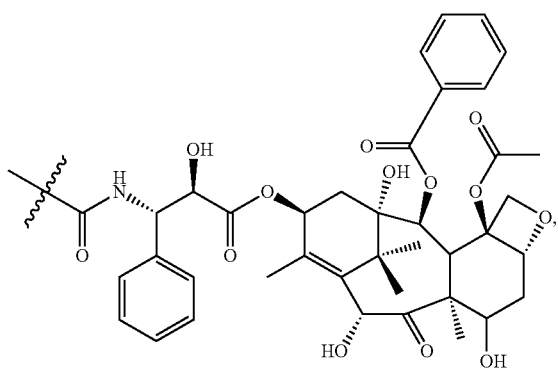

where the wavy line indicates a connection to $L^1$.

2. The compound of claim 1, wherein $R^1$ or $R^2$ is the -$L^1$-$R^{B1}$ group wherein the $R^{B1}$ group comprises the nucleic acid-binding moiety or the cytoskeleton-binding moiety.

3. The compound of claim 2, wherein the $L^1$ group comprises —(CH$_2$)$_s$—X-$L^{3a}$-, where s is independently 2, 3, 4, 5, or 6; each X is independently CH$_2$, S, S(O), or S(O)$_2$; and each $L^{3a}$ is independently —(CH$_2$)$_p$ where p is 0, 1, 2, 3, 4, 5, or 6.

4. The compound of claim 1, wherein the compound is any one of compounds
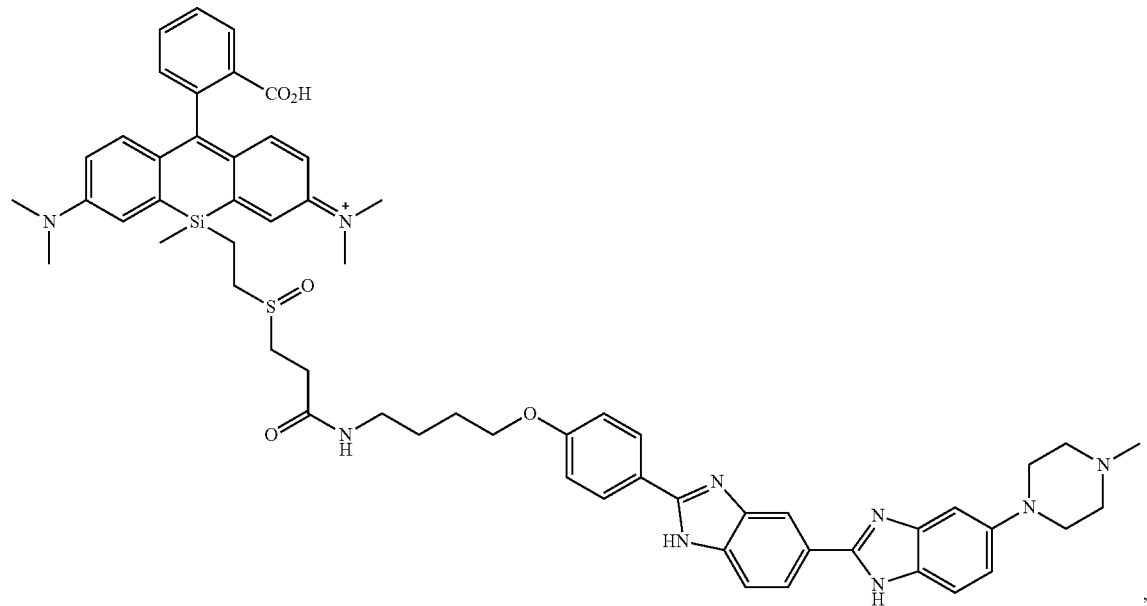
Compound 4A
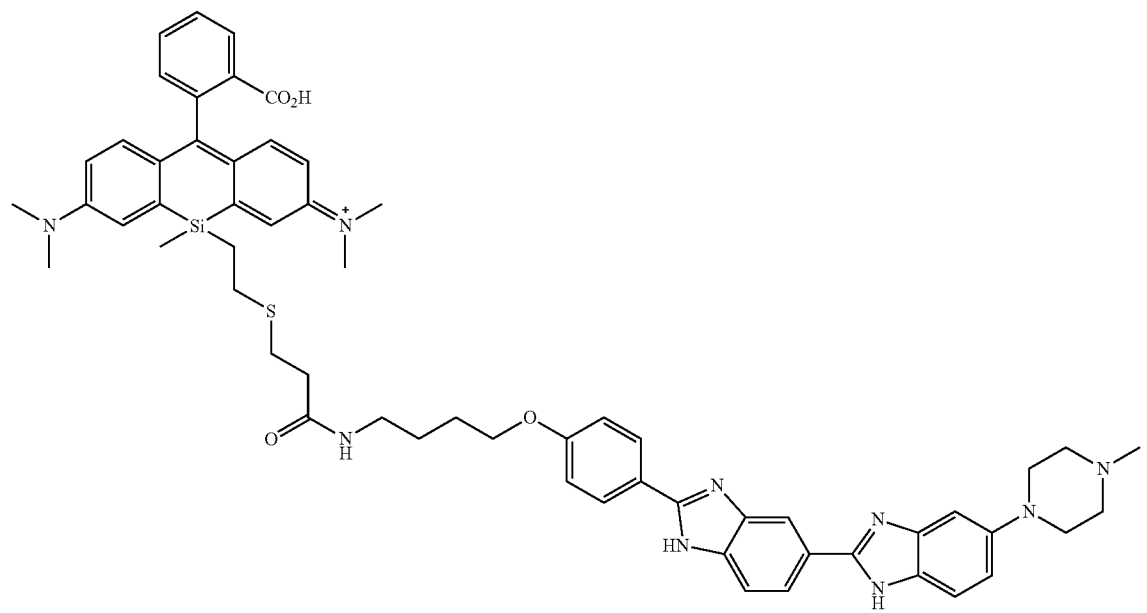
Compound 4

Compound 5
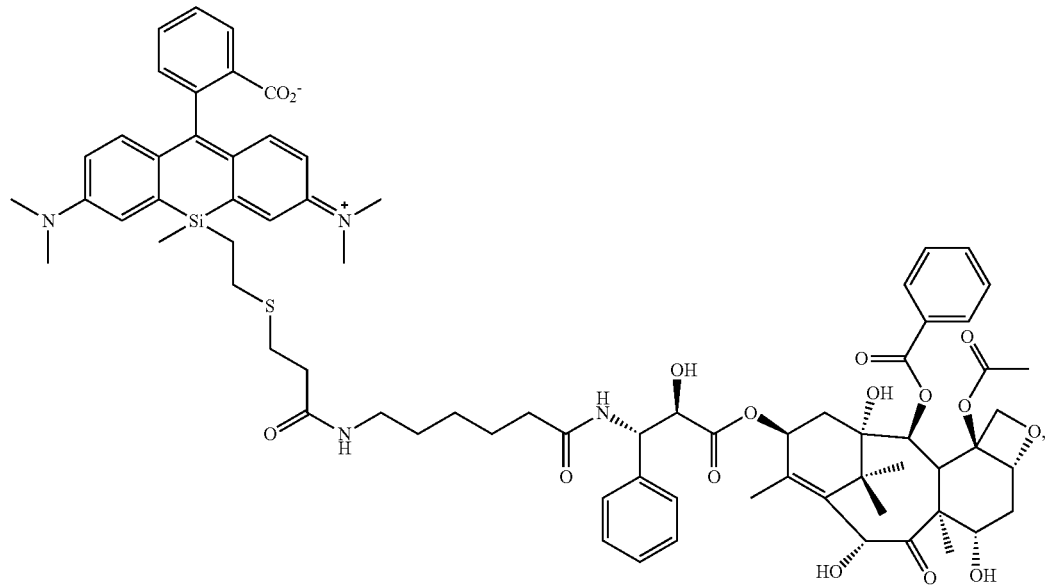
Compound 6
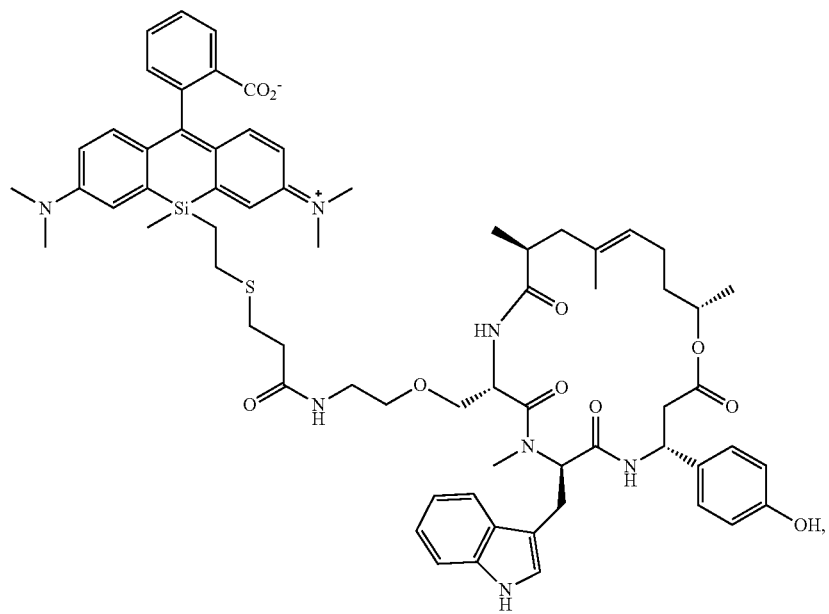

-continued
Compound 6
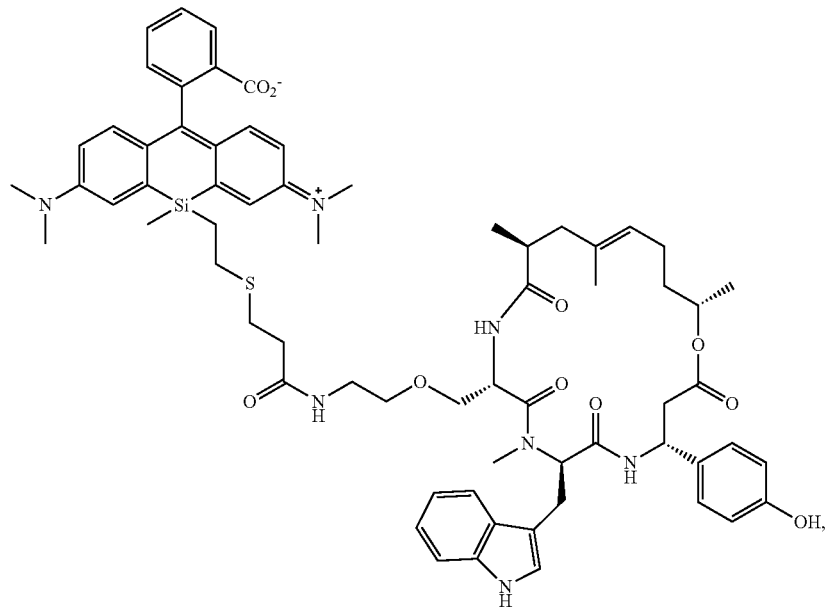
Compound 6A
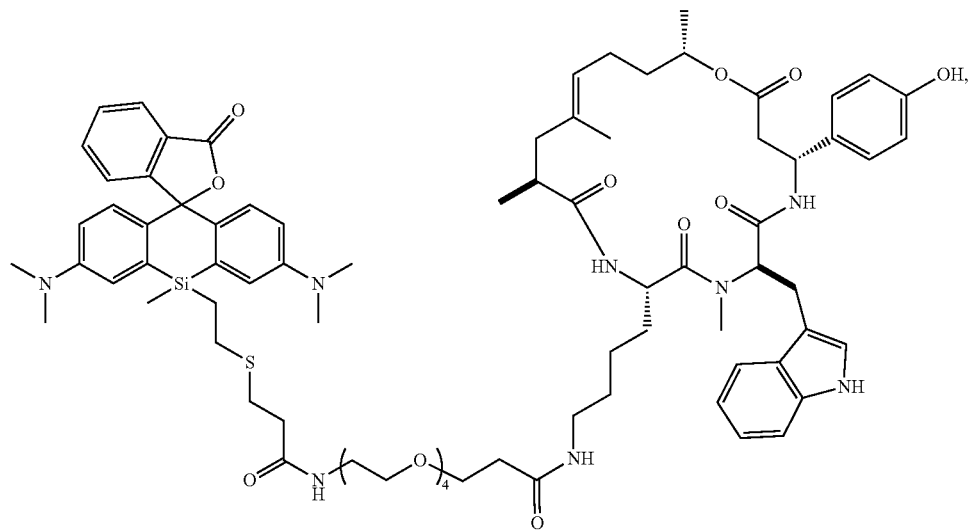
Compound 6B
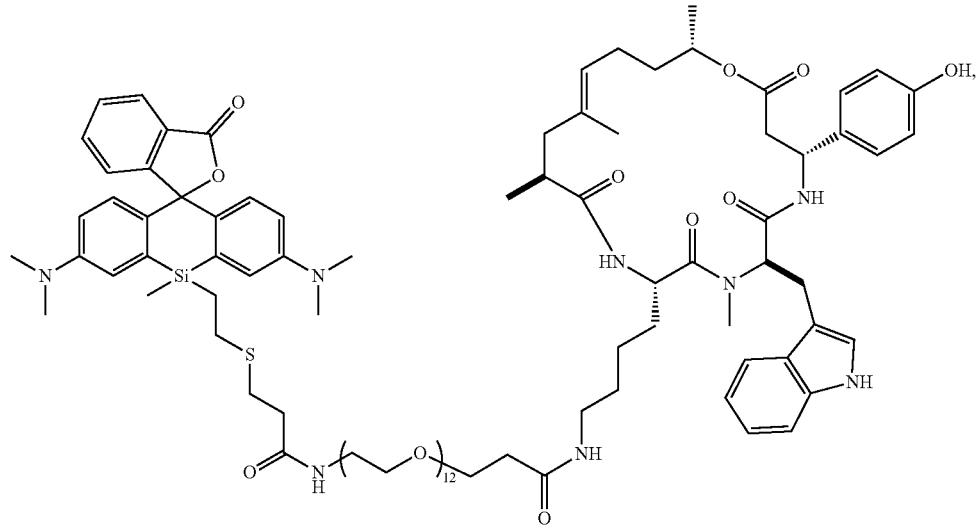

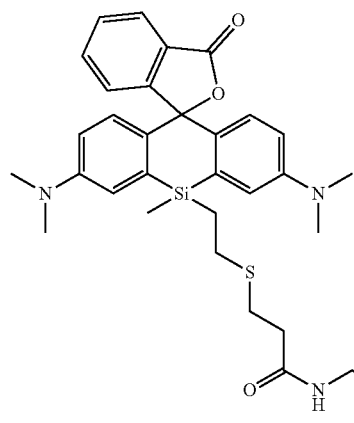
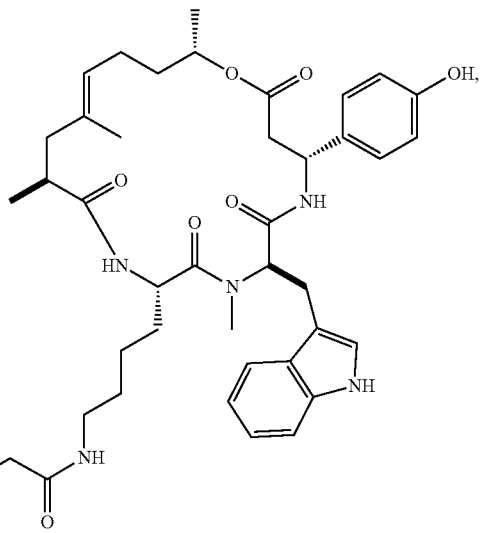

Compound 6C or an open or spirolactone form and/or salt or free acid thereof.

5. A fluorescent complex comprising a compound of claim 1 that comprises the nucleic acid-binding moiety or the cytoskeleton binding moiety non-covalently associated with an intracellular component.

6. A kit for detecting a target, comprising a compound of claim 1 that comprises the nucleic acid-binding moiety or the cytoskeleton-binding moiety configured to specifically bind the target.

7. A compound selected from:

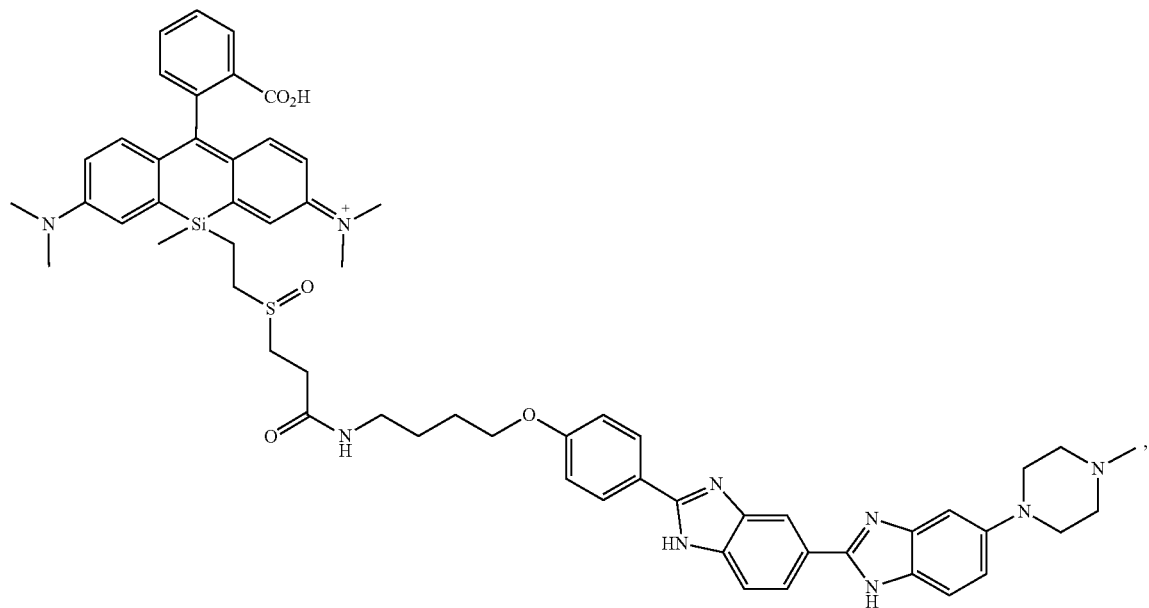

Compound 4A

Compound 4
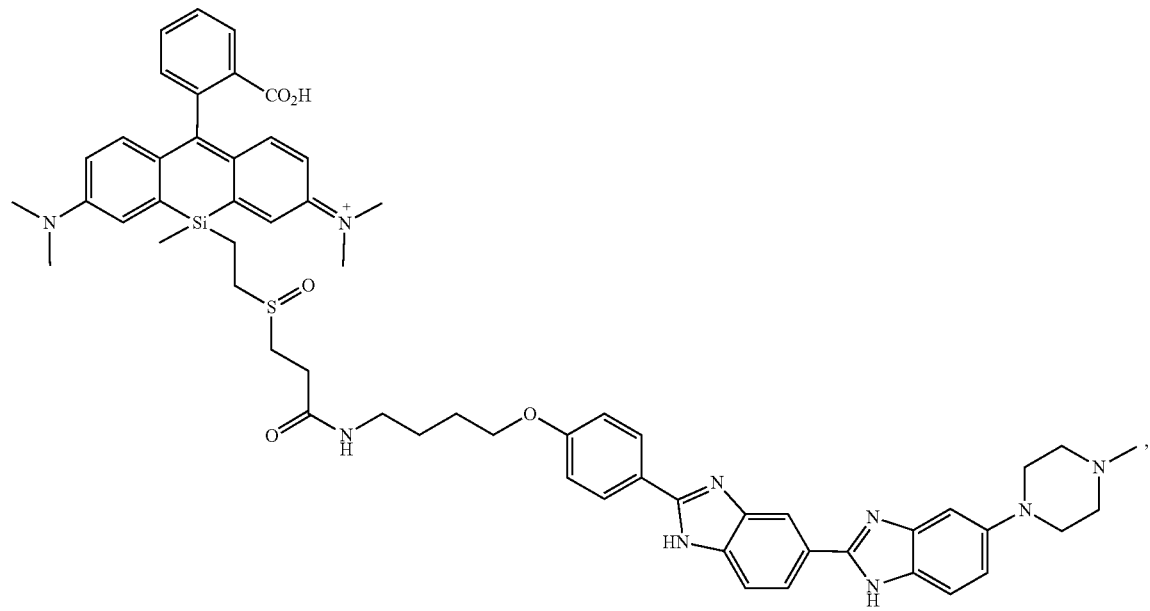
Compound 5
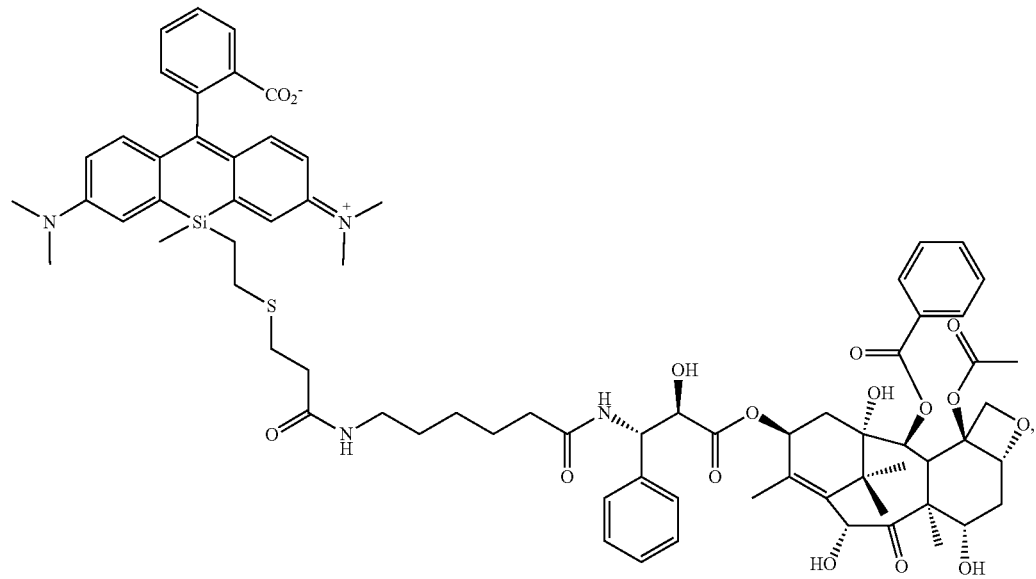

-continued
Compound 6
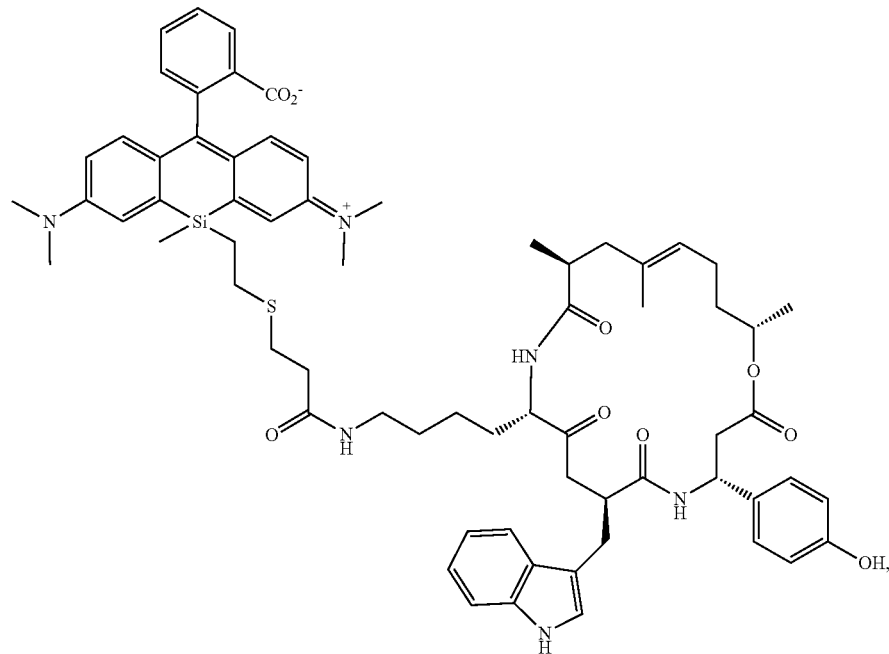
Compound 6A
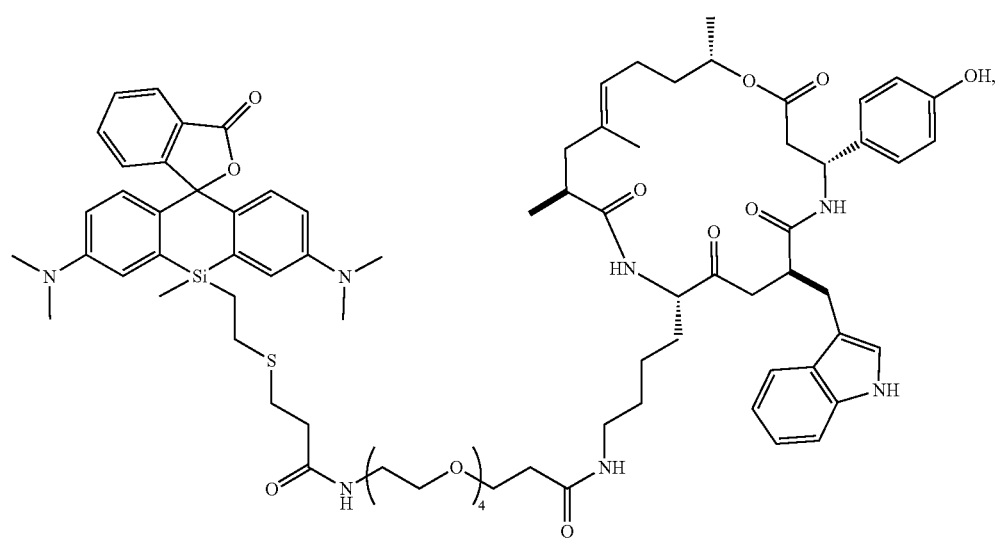

Compound 6B
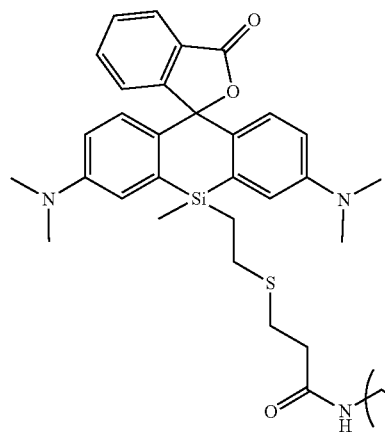 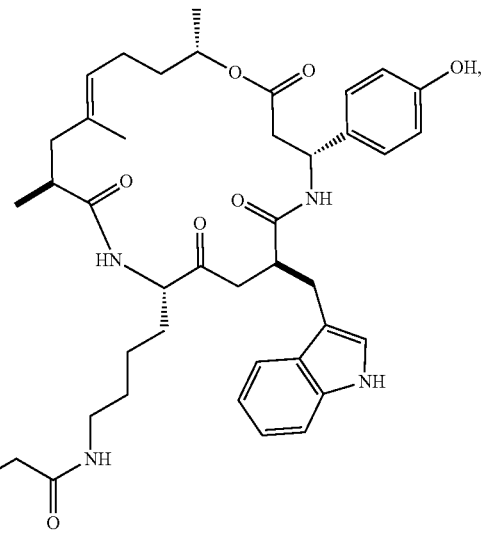
Compound 6C
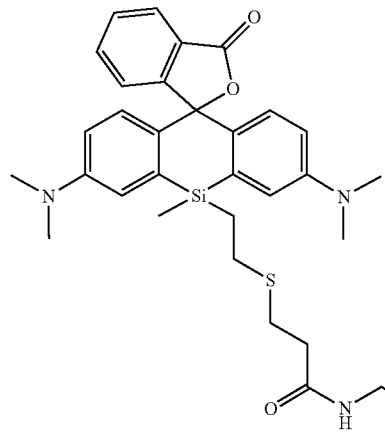 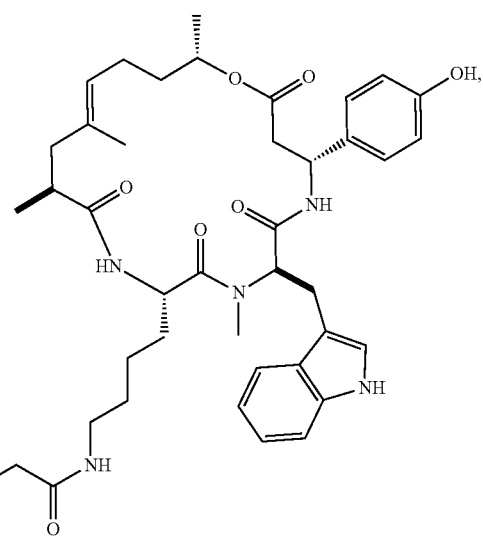
Compound 7
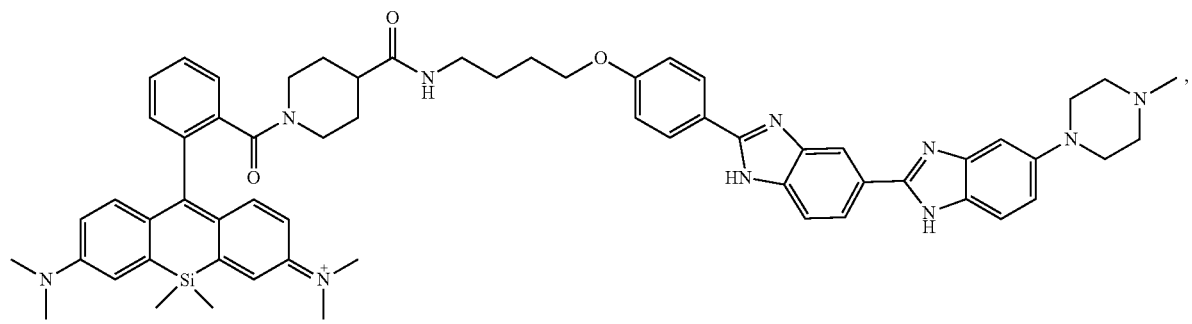

-continued
Compound 7B
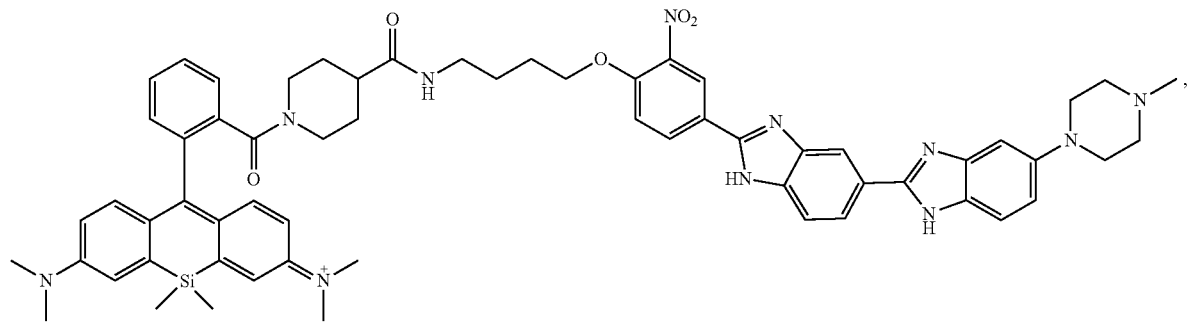
or an open or spirolactone form and/or a salt or free acid thereof.
* * * * *

UNITED STATES PATENT AND TRADEMARK OFFICE
CERTIFICATE OF CORRECTION

PATENT NO. : 12,258,477 B2
APPLICATION NO. : 17/150247
DATED : March 25, 2025
INVENTOR(S) : Yang et al.

Page 1 of 6

It is certified that error appears in the above-identified patent and that said Letters Patent is hereby corrected as shown below:

In the Claims

In Column 94, Claim 3, Line 65, "—(CH$_2$)$_p$" should read "—CH$_2$)$_p$—".

In Columns 97-98, Claim 4, the structure for Compound 6,

"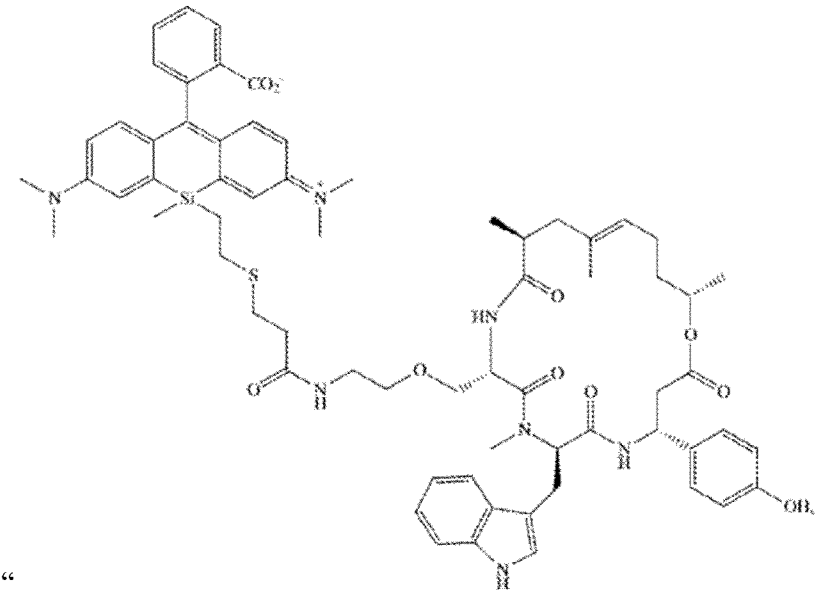" should read

Signed and Sealed this
Twenty-second Day of July, 2025

Coke Morgan Stewart
*Acting Director of the United States Patent and Trademark Office*

CERTIFICATE OF CORRECTION (continued)
U.S. Pat. No. 12,258,477 B2

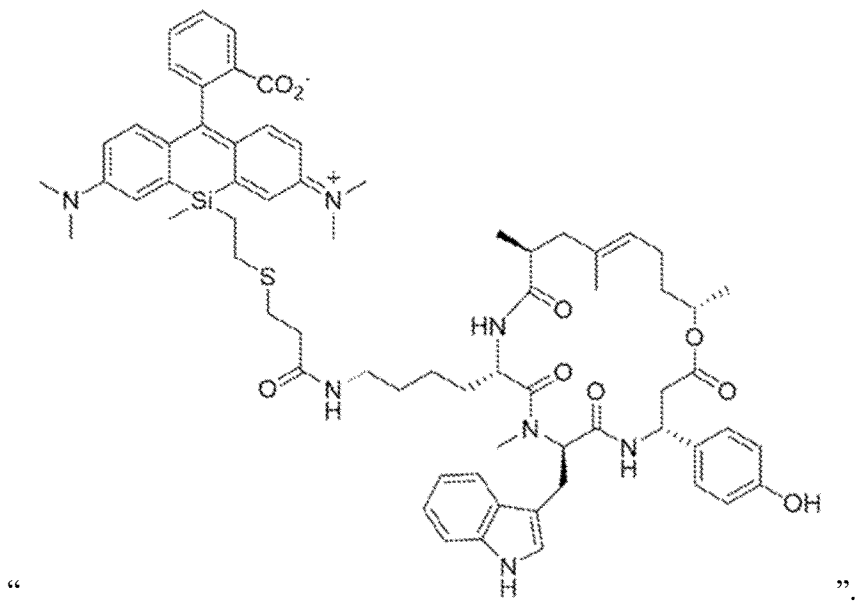

" ".

In Columns 99-100, Claim 3, delete the structure for Compound 6 and delete "Compound 6".

In Columns 103-104, Claim 7, the structure for Compound 4,

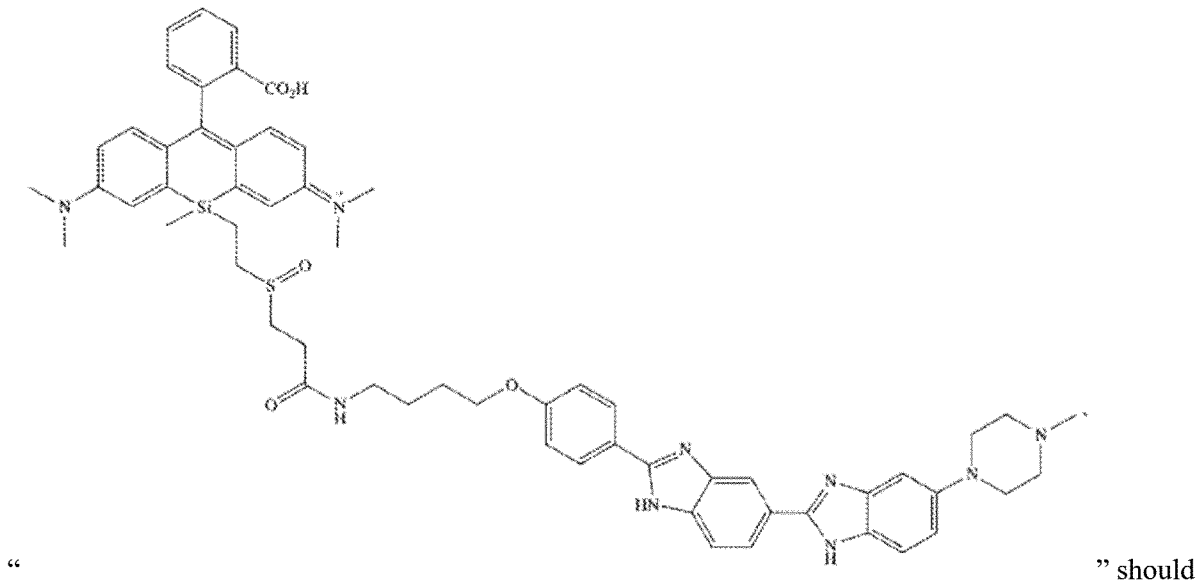

" should

CERTIFICATE OF CORRECTION (continued)
U.S. Pat. No. 12,258,477 B2 read " 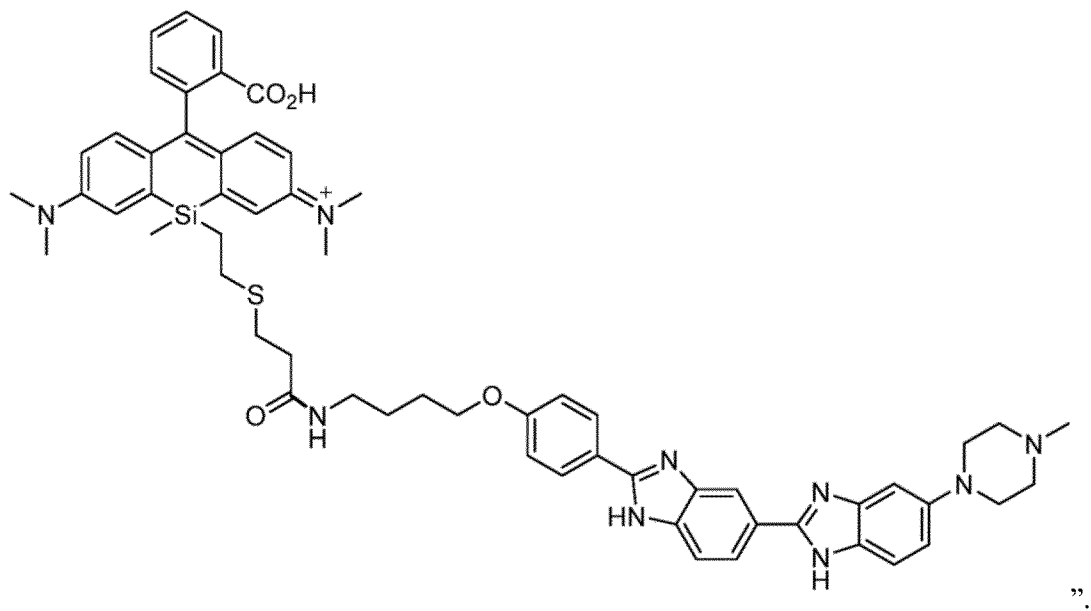 ".

In Columns 105-106, Claim 7, the structure for Compound 6,

" 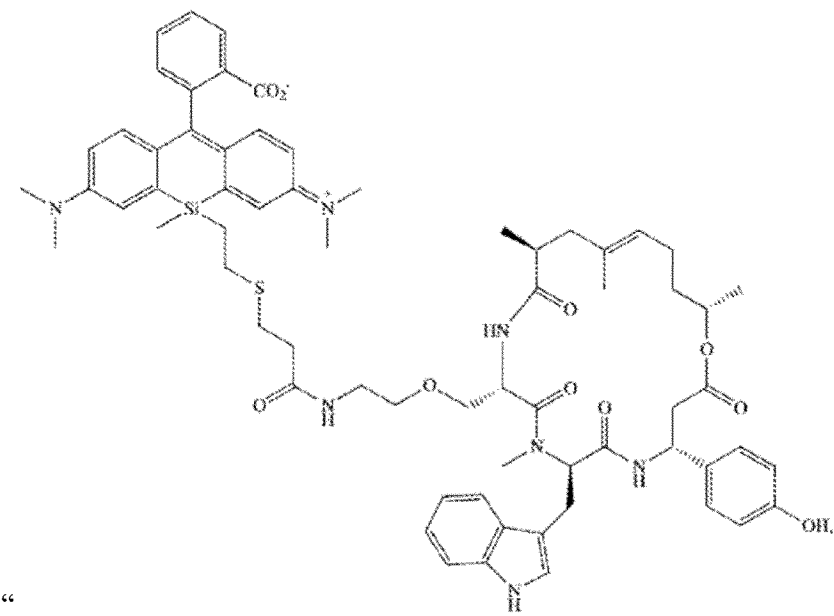 " should read

CERTIFICATE OF CORRECTION (continued)
U.S. Pat. No. 12,258,477 B2

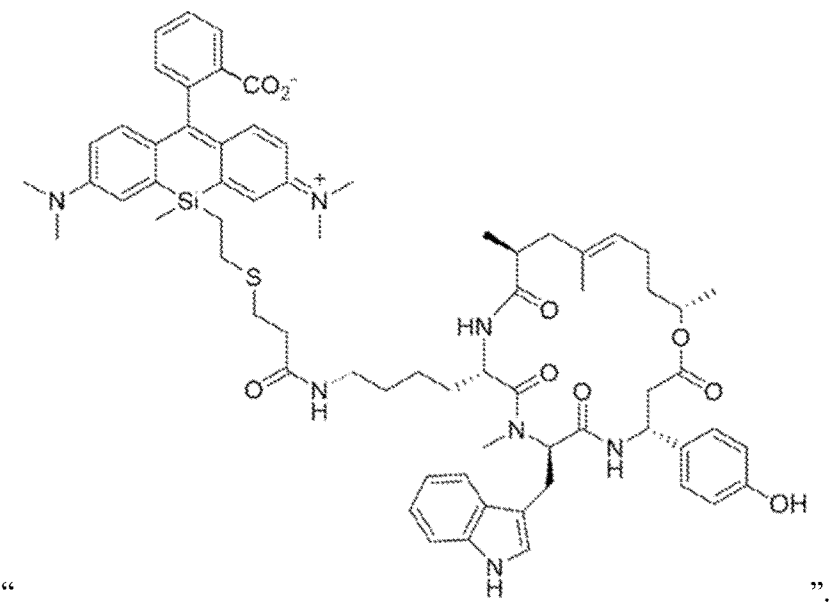

" ".

In Columns 105-106, Claim 7, the structure for Compound 6A,

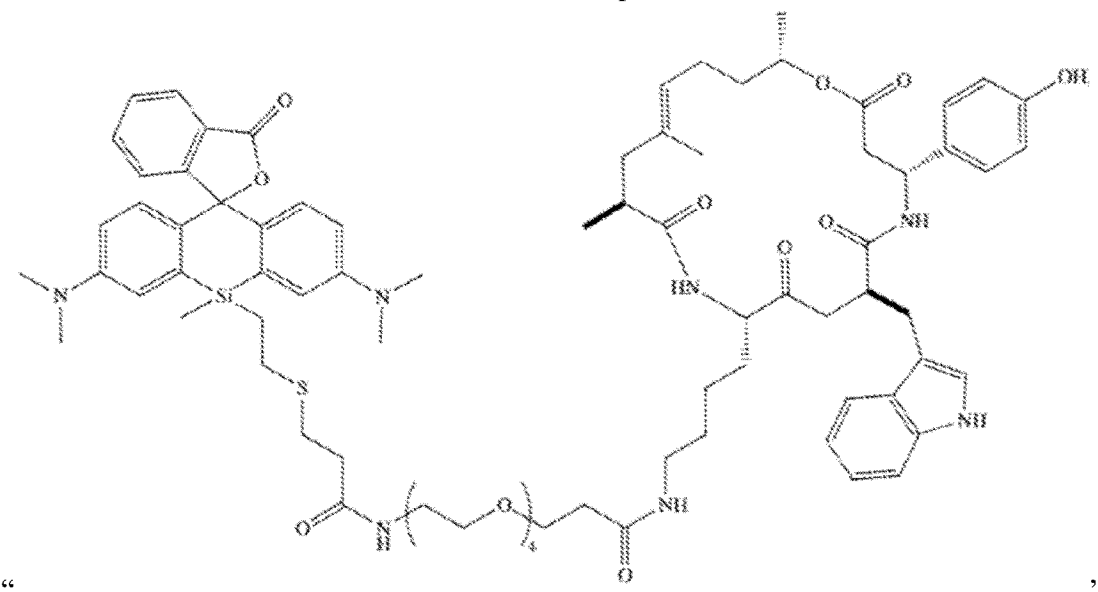

" " should

CERTIFICATE OF CORRECTION (continued)
U.S. Pat. No. 12,258,477 B2

Page 5 of 6

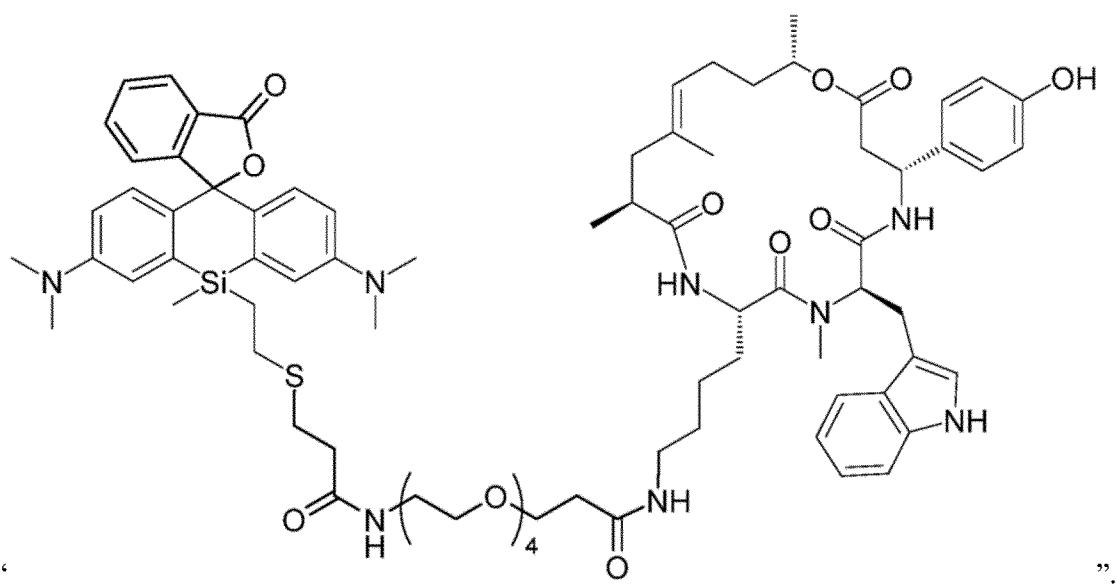

read "                                                                                                                    ".

In Columns 107-108, Claim 7, the structure for Compound 6B,

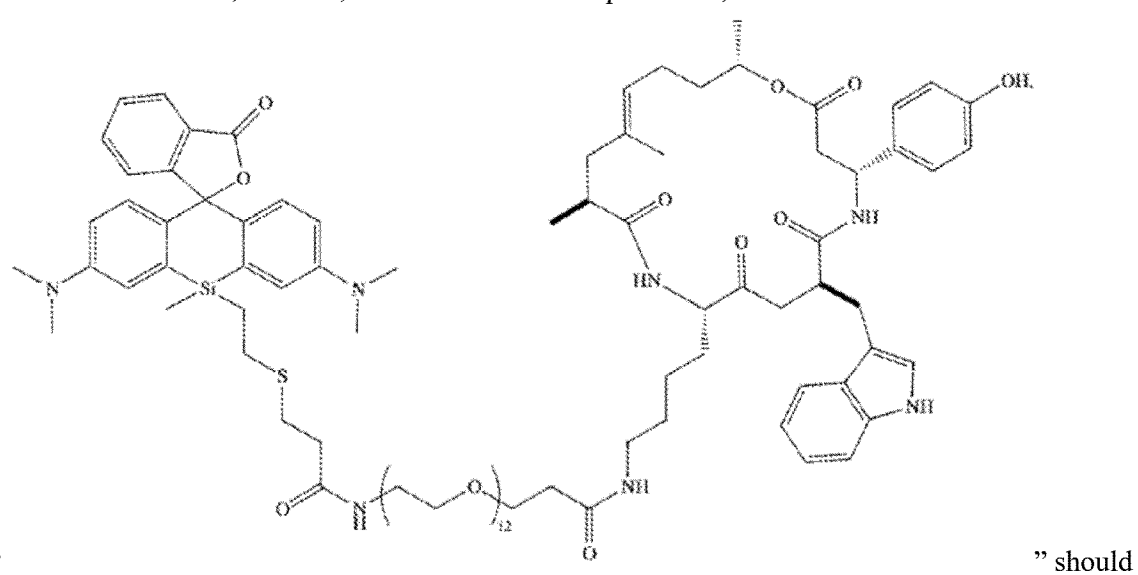

"                                                                                                                    " should

CERTIFICATE OF CORRECTION (continued)

read " 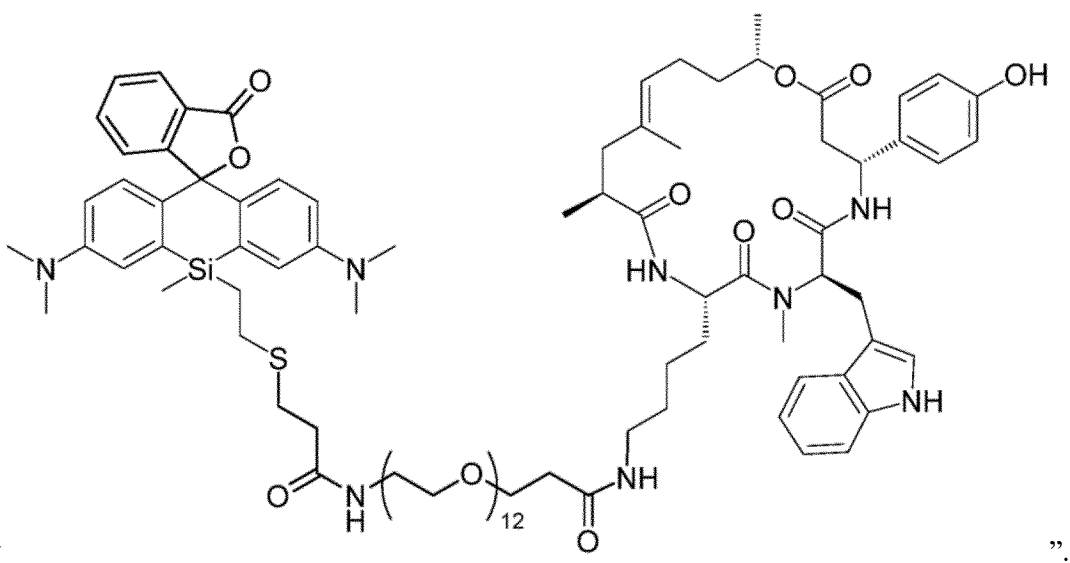 ".